United States Patent
Li et al.

(10) Patent No.: US 12,104,204 B2
(45) Date of Patent: Oct. 1, 2024

(54) USE OF HIGH-TEMPERATURE-RESISTANT CAS PROTEIN, AND METHOD AND REAGENT KIT FOR DETECTING TARGET NUCLEIC ACID MOLECULE

(71) Applicant: SHANGHAI TOLO BIOTECHNOLOGY COMPANY LIMITED, Shanghai (CN)

(72) Inventors: Shiyuan Li, Shanghai (CN); Jin Wang, Shanghai (CN)

(73) Assignee: SHANGHAI TOLO BIOTECHNOLOGY COMPANY LIMITED, Shanghai (CN)

( * ) Notice: Subject to any disclaimer, the term of this patent is extended or adjusted under 35 U.S.C. 154(b) by 0 days.

(21) Appl. No.: 15/734,760

(22) PCT Filed: Jun. 3, 2019

(86) PCT No.: PCT/CN2019/089856
§ 371 (c)(1),
(2) Date: Dec. 3, 2020

(87) PCT Pub. No.: WO2019/233385
PCT Pub. Date: Dec. 12, 2019

(65) Prior Publication Data
US 2021/0238666 A1    Aug. 5, 2021

(30) Foreign Application Priority Data

Jun. 3, 2018  (CN) .......................... 201810560284.8

(51) Int. Cl.
*C12Q 1/6858*    (2018.01)
(52) U.S. Cl.
CPC ..... *C12Q 1/6858* (2013.01); *C12Q 2600/158* (2013.01)
(58) Field of Classification Search
CPC .............................. C12N 2310/20; C12N 9/22; C12Q 2521/301; C12Q 2563/107; C12Q 2565/1015; C12Q 1/6816; C12Q 2521/337
See application file for complete search history.

(56) References Cited

U.S. PATENT DOCUMENTS

2019/0241954 A1*  8/2019  Doudna ............... C12Q 1/6876
2021/0388437 A1* 12/2021  Doudna ............... C12Q 1/6876

FOREIGN PATENT DOCUMENTS

CN     107488710 A    12/2017
CN     107849546 A     3/2018

OTHER PUBLICATIONS

Gootenberg et al., "Nucleic acid detection with CRISPR-Cas13a/C2c2", Science, vol. 356, pp. 438-442. (Year: 2017).*
Hille et al., "The Biology of CRISPR-Cas: Backward and Forward," Cell, March, vol. 172, pp. 1239-1259. (Year: 2018).*
Chen et al., "CRISPR-Cas12a target binding unleashes indiscriminate single-stranded DNase activity," April, vol. 360, pp. 436-439. (Year: 2018).*
Strecker et al., Engineering of CRISPR-Cas12b for human genome editing, Nature Communications, vol. 10, pp. 1-8. (Year: 2019).*
Shmakov et al., "Discovery and Functional Characterization of Diverse Class 2 CRISPR-Cas Systems," Molecular Cell, vol. 60, pp. 385-397. (Year: 2015).*
Araki et al., "Usefulness of Peptide Nucleic Acid (PNA)-Clamp Smart Amplification Process Version 2 (SmartAmp2) for Clinical Diagnosis of KRAS Codon 12 Mutations in Lung Adenocarcinoma," Journal of Molecular Diagnostics, January, vol. 12, No. 1, pp. 118-124. (Year: 2010).*
Nishimoto et al., "Identification of a novel smooth muscle associated protein, smap2, upregulated during neointima formation in a rat carotid endarterectomy model," Biochimica et Biophysica Acta, vol. 1576, pp. 225-230. (Year: 2002).*

* cited by examiner

*Primary Examiner* — Young J Kim
(74) *Attorney, Agent, or Firm* — NKL Law; Allen Xue

(57) ABSTRACT

The present invention provides a use of a high-temperature-resistant Cas protein, and a system and reagent kit for detecting a target nucleic acid molecule; specifically, the present invention provides a reaction system used for detecting a target nucleic acid molecule, said reaction system comprising: a guide RNA, Cas12b (formerly known as C2c1), and a nucleic acid probe; after a reaction is completed, detection of the nucleic acid is performed. In addition, by means of combining with nucleic acid amplification techniques (such as LAMP and the like), the sensitivity of the described detection method can be significantly improved. The detection system provided by the present invention can be used for rapidly detecting pathogenic microorganisms, gene mutations, single nucleotide polymorphisms, specific target DNA, and the like, and for quantifying nucleic acid samples.

10 Claims, 32 Drawing Sheets
Specification includes a Sequence Listing.

SEQUENCE LISTING

<160> NUMBER OF SEQ ID NOS: 217

<210> SEQ ID NO 1
<211> LENGTH: 66
<212> TYPE: DNA
<213> ORGANISM: artificial sequence
<220> FEATURE:
<223> OTHER INFORMATION: synthesized

<400> SEQUENCE: 1
tttctgtttg ttatcgcaac tttctactga attcaagctt tactctagaa agaggagaaa    60
ggatcc    66

<210> SEQ ID NO 2
<211> LENGTH: 66
<212> TYPE: DNA
<213> ORGANISM: artificial sequence
<220> FEATURE:
<223> OTHER INFORMATION: synthesized

<400> SEQUENCE: 2
ggatcctttc tcctctttct agagtaaagc ttgaattcag tagaaagttg cgataacaaa    60
cagaaa    66

<210> SEQ ID NO 3
<211> LENGTH: 66
<212> TYPE: DNA
<213> ORGANISM: artificial sequence
<220> FEATURE:
<223> OTHER INFORMATION: synthesized

<400> SEQUENCE: 3
ggatcctttc tcctctttct agagtaaagc ttgaattcag tagaaagttg cgataacaaa    60
cagaaa    66

<210> SEQ ID NO 4
<211> LENGTH: 66
<212> TYPE: DNA
<213> ORGANISM: artificial sequence
<220> FEATURE:
<223> OTHER INFORMATION: synthesized

<400> SEQUENCE: 4

```
ggatcctttc tcctctttct agagtaaagc ttgaattcag tagaaagttg cgataacaaa      60
cagaaa                                                                 66

<210> SEQ ID NO 5
<211> LENGTH: 50
<212> TYPE: DNA
<213> ORGANISM: artificial sequence
<220> FEATURE:
<223> OTHER INFORMATION: synthesized

<400> SEQUENCE: 5
aatgttccct gatggtccat gtctgttact cgcctgtcaa gtggcgtgac                 50

<210> SEQ ID NO 6
<211> LENGTH: 50
<212> TYPE: DNA
<213> ORGANISM: artificial sequence
<220> FEATURE:
<223> OTHER INFORMATION: synthesized

<400> SEQUENCE: 6
gtcacgccac ttgacaggcg agtaacagac atggaccatc agggaacatt                 50

<210> SEQ ID NO 7
<211> LENGTH: 50
<212> TYPE: DNA
<213> ORGANISM: artificial sequence
<220> FEATURE:
<223> OTHER INFORMATION: synthesized

<400> SEQUENCE: 7
aatgaaccct gatggtccat gtctgttact cgcctgtcaa gtggcgtgac                 50

<210> SEQ ID NO 8
<211> LENGTH: 50
<212> TYPE: DNA
<213> ORGANISM: artificial sequence
<220> FEATURE:
<223> OTHER INFORMATION: synthesized

<400> SEQUENCE: 8
gtcacgccac ttgacaggcg agtaacagac atggaccatc agggttcatt                 50

<210> SEQ ID NO 9
<211> LENGTH: 50
<212> TYPE: DNA
<213> ORGANISM: artificial sequence
<220> FEATURE:
<223> OTHER INFORMATION: synthesized

<400> SEQUENCE: 9
aatgatccct gatggtccat gtctgttact cgcctgtcaa gtggcgtgac                 50

<210> SEQ ID NO 10
<211> LENGTH: 50
<212> TYPE: DNA
<213> ORGANISM: artificial sequence
<220> FEATURE:
<223> OTHER INFORMATION: synthesized

<400> SEQUENCE: 10
gtcacgccac ttgacaggcg agtaacagac atggaccatc agggatcatt                 50

<210> SEQ ID NO 11
<211> LENGTH: 50
```

```
<212> TYPE: DNA
<213> ORGANISM: artificial sequence
<220> FEATURE:
<223> OTHER INFORMATION: synthesized

<400> SEQUENCE: 11
aatgtaccct gatggtccat gtctgttact cgcctgtcaa gtggcgtgac          50

<210> SEQ ID NO 12
<211> LENGTH: 50
<212> TYPE: DNA
<213> ORGANISM: artificial sequence
<220> FEATURE:
<223> OTHER INFORMATION: synthesized

<400> SEQUENCE: 12
gtcacgccac ttgacaggcg agtaacagac atggaccatc agggtacatt          50

<210> SEQ ID NO 13
<211> LENGTH: 50
<212> TYPE: DNA
<213> ORGANISM: artificial sequence
<220> FEATURE:
<223> OTHER INFORMATION: synthesized

<400> SEQUENCE: 13
gtcacgccac ttgacaggcg agtaacagac atggaccatc agggcccatt          50

<210> SEQ ID NO 14
<211> LENGTH: 50
<212> TYPE: DNA
<213> ORGANISM: artificial sequence
<220> FEATURE:
<223> OTHER INFORMATION: synthesized

<400> SEQUENCE: 14
gtcacgccac ttgacaggcg agtaacagac atggaccatc aggggggcatt         50

<210> SEQ ID NO 15
<211> LENGTH: 50
<212> TYPE: DNA
<213> ORGANISM: artificial sequence
<220> FEATURE:
<223> OTHER INFORMATION: synthesized

<400> SEQUENCE: 15
aatgttcgct gatggtccat gtctgttact cgcctgtcaa gtggcgtgac          50

<210> SEQ ID NO 16
<211> LENGTH: 50
<212> TYPE: DNA
<213> ORGANISM: artificial sequence
<220> FEATURE:
<223> OTHER INFORMATION: synthesized

<400> SEQUENCE: 16
gtcacgccac ttgacaggcg agtaacagac atggaccatc agcgaacatt          50

<210> SEQ ID NO 17
<211> LENGTH: 50
<212> TYPE: DNA
<213> ORGANISM: artificial sequence
<220> FEATURE:
<223> OTHER INFORMATION: synthesized

<400> SEQUENCE: 17
```
aatgttccgt gatggtccat gtctgttact cgcctgtcaa gtggcgtgac    50

<210> SEQ ID NO 18
<211> LENGTH: 50
<212> TYPE: DNA
<213> ORGANISM: artificial sequence
<220> FEATURE:
<223> OTHER INFORMATION: synthesized

<400> SEQUENCE: 18
gtcacgccac ttgacaggcg agtaacagac atggaccatc acggaacatt    50

<210> SEQ ID NO 19
<211> LENGTH: 50
<212> TYPE: DNA
<213> ORGANISM: artificial sequence
<220> FEATURE:
<223> OTHER INFORMATION: synthesized

<400> SEQUENCE: 19
aatgttccca gatggtccat gtctgttact cgcctgtcaa gtggcgtgac    50

<210> SEQ ID NO 20
<211> LENGTH: 50
<212> TYPE: DNA
<213> ORGANISM: artificial sequence
<220> FEATURE:
<223> OTHER INFORMATION: synthesized

<400> SEQUENCE: 20
gtcacgccac ttgacaggcg agtaacagac atggaccatc tgggaacatt    50

<210> SEQ ID NO 21
<211> LENGTH: 50
<212> TYPE: DNA
<213> ORGANISM: artificial sequence
<220> FEATURE:
<223> OTHER INFORMATION: synthesized

<400> SEQUENCE: 21
aatgttccct catggtccat gtctgttact cgcctgtcaa gtggcgtgac    50

<210> SEQ ID NO 22
<211> LENGTH: 50
<212> TYPE: DNA
<213> ORGANISM: artificial sequence
<220> FEATURE:
<223> OTHER INFORMATION: synthesized

<400> SEQUENCE: 22
gtcacgccac ttgacaggcg agtaacagac atggaccatg agggaacatt    50

<210> SEQ ID NO 23
<211> LENGTH: 50
<212> TYPE: DNA
<213> ORGANISM: artificial sequence
<220> FEATURE:
<223> OTHER INFORMATION: synthesized

<400> SEQUENCE: 23
aatgttccct gttggtccat gtctgttact cgcctgtcaa gtggcgtgac    50

<210> SEQ ID NO 24
<211> LENGTH: 50
<212> TYPE: DNA
<213> ORGANISM: artificial sequence -continued
<220> FEATURE:
<223> OTHER INFORMATION: synthesized

<400> SEQUENCE: 24
gtcacgccac ttgacaggcg agtaacagac atggaccaac agggaacatt           50

<210> SEQ ID NO 25
<211> LENGTH: 50
<212> TYPE: DNA
<213> ORGANISM: artificial sequence
<220> FEATURE:
<223> OTHER INFORMATION: synthesized

<400> SEQUENCE: 25
aatgttccct gaaggtccat gtctgttact cgcctgtcaa gtggcgtgac           50

<210> SEQ ID NO 26
<211> LENGTH: 50
<212> TYPE: DNA
<213> ORGANISM: artificial sequence
<220> FEATURE:
<223> OTHER INFORMATION: synthesized

<400> SEQUENCE: 26
gtcacgccac ttgacaggcg agtaacagac atggaccttc agggaacatt           50

<210> SEQ ID NO 27
<211> LENGTH: 50
<212> TYPE: DNA
<213> ORGANISM: artificial sequence
<220> FEATURE:
<223> OTHER INFORMATION: synthesized

<400> SEQUENCE: 27
aatgttccct gatcgtccat gtctgttact cgcctgtcaa gtggcgtgac           50

<210> SEQ ID NO 28
<211> LENGTH: 50
<212> TYPE: DNA
<213> ORGANISM: artificial sequence
<220> FEATURE:
<223> OTHER INFORMATION: synthesized

<400> SEQUENCE: 28
gtcacgccac ttgacaggcg agtaacagac atggacgatc agggaacatt           50

<210> SEQ ID NO 29
<211> LENGTH: 50
<212> TYPE: DNA
<213> ORGANISM: artificial sequence
<220> FEATURE:
<223> OTHER INFORMATION: synthesized

<400> SEQUENCE: 29
aatgttccct gatgctccat gtctgttact cgcctgtcaa gtggcgtgac           50

<210> SEQ ID NO 30
<211> LENGTH: 50
<212> TYPE: DNA
<213> ORGANISM: artificial sequence
<220> FEATURE:
<223> OTHER INFORMATION: synthesized

<400> SEQUENCE: 30
gtcacgccac ttgacaggcg agtaacagac atggagcatc agggaacatt           50

```
<210> SEQ ID NO 31
<211> LENGTH: 50
<212> TYPE: DNA
<213> ORGANISM: artificial sequence
<220> FEATURE:
<223> OTHER INFORMATION: synthesized

<400> SEQUENCE: 31
aatgttccct gatggaccat gtctgttact cgcctgtcaa gtggcgtgac         50

<210> SEQ ID NO 32
<211> LENGTH: 50
<212> TYPE: DNA
<213> ORGANISM: artificial sequence
<220> FEATURE:
<223> OTHER INFORMATION: synthesized

<400> SEQUENCE: 32
gtcacgccac ttgacaggcg agtaacagac atggtccatc agggaacatt         50

<210> SEQ ID NO 33
<211> LENGTH: 50
<212> TYPE: DNA
<213> ORGANISM: artificial sequence
<220> FEATURE:
<223> OTHER INFORMATION: synthesized

<400> SEQUENCE: 33
aatgttccct gatggtgcat gtctgttact cgcctgtcaa gtggcgtgac         50

<210> SEQ ID NO 34
<211> LENGTH: 50
<212> TYPE: DNA
<213> ORGANISM: artificial sequence
<220> FEATURE:
<223> OTHER INFORMATION: synthesized

<400> SEQUENCE: 34
gtcacgccac ttgacaggcg agtaacagac atgcaccatc agggaacatt         50

<210> SEQ ID NO 35
<211> LENGTH: 50
<212> TYPE: DNA
<213> ORGANISM: artificial sequence
<220> FEATURE:
<223> OTHER INFORMATION: synthesized

<400> SEQUENCE: 35
aatgttccct gatggtcgat gtctgttact cgcctgtcaa gtggcgtgac         50

<210> SEQ ID NO 36
<211> LENGTH: 50
<212> TYPE: DNA
<213> ORGANISM: artificial sequence
<220> FEATURE:
<223> OTHER INFORMATION: synthesized

<400> SEQUENCE: 36
gtcacgccac ttgacaggcg agtaacagac atcgaccatc agggaacatt         50

<210> SEQ ID NO 37
<211> LENGTH: 50
<212> TYPE: DNA
<213> ORGANISM: artificial sequence
<220> FEATURE:
<223> OTHER INFORMATION: synthesized
```

<400> SEQUENCE: 37
aatgttccct gatggtcctt gtctgttact cgcctgtcaa gtggcgtgac            50

<210> SEQ ID NO 38
<211> LENGTH: 50
<212> TYPE: DNA
<213> ORGANISM: artificial sequence
<220> FEATURE:
<223> OTHER INFORMATION: synthesized

<400> SEQUENCE: 38
gtcacgccac ttgacaggcg agtaacagac aaggaccatc agggaacatt            50

<210> SEQ ID NO 39
<211> LENGTH: 50
<212> TYPE: DNA
<213> ORGANISM: artificial sequence
<220> FEATURE:
<223> OTHER INFORMATION: synthesized

<400> SEQUENCE: 39
aatgttccct gatggtccaa gtctgttact cgcctgtcaa gtggcgtgac            50

<210> SEQ ID NO 40
<211> LENGTH: 50
<212> TYPE: DNA
<213> ORGANISM: artificial sequence
<220> FEATURE:
<223> OTHER INFORMATION: synthesized

<400> SEQUENCE: 40
gtcacgccac ttgacaggcg agtaacagac ttggaccatc agggaacatt            50

<210> SEQ ID NO 41
<211> LENGTH: 50
<212> TYPE: DNA
<213> ORGANISM: artificial sequence
<220> FEATURE:
<223> OTHER INFORMATION: synthesized

<400> SEQUENCE: 41
aatgttccct gatggtccat ctctgttact cgcctgtcaa gtggcgtgac            50

<210> SEQ ID NO 42
<211> LENGTH: 50
<212> TYPE: DNA
<213> ORGANISM: artificial sequence
<220> FEATURE:
<223> OTHER INFORMATION: synthesized

<400> SEQUENCE: 42
gtcacgccac ttgacaggcg agtaacagag atggaccatc agggaacatt            50

<210> SEQ ID NO 43
<211> LENGTH: 50
<212> TYPE: DNA
<213> ORGANISM: artificial sequence
<220> FEATURE:
<223> OTHER INFORMATION: synthesized

<400> SEQUENCE: 43
aatgttccct gatggtccat gactgttact cgcctgtcaa gtggcgtgac            50

<210> SEQ ID NO 44

```
<211> LENGTH: 50
<212> TYPE: DNA
<213> ORGANISM: artificial sequence
<220> FEATURE:
<223> OTHER INFORMATION: synthesized

<400> SEQUENCE: 44
gtcacgccac ttgacaggcg agtaacagtc atggaccatc agggaacatt          50

<210> SEQ ID NO 45
<211> LENGTH: 50
<212> TYPE: DNA
<213> ORGANISM: artificial sequence
<220> FEATURE:
<223> OTHER INFORMATION: synthesized

<400> SEQUENCE: 45
aatgttccct gatggtccat gtgtgttact cgcctgtcaa gtggcgtgac          50

<210> SEQ ID NO 46
<211> LENGTH: 50
<212> TYPE: DNA
<213> ORGANISM: artificial sequence
<220> FEATURE:
<223> OTHER INFORMATION: synthesized

<400> SEQUENCE: 46
gtcacgccac ttgacaggcg agtaacacac atggaccatc agggaacatt          50

<210> SEQ ID NO 47
<211> LENGTH: 50
<212> TYPE: DNA
<213> ORGANISM: artificial sequence
<220> FEATURE:
<223> OTHER INFORMATION: synthesized

<400> SEQUENCE: 47
aatgttccct gatggtccat gtcagttact cgcctgtcaa gtggcgtgac          50

<210> SEQ ID NO 48
<211> LENGTH: 50
<212> TYPE: DNA
<213> ORGANISM: artificial sequence
<220> FEATURE:
<223> OTHER INFORMATION: synthesized

<400> SEQUENCE: 48
gtcacgccac ttgacaggcg agtaactgac atggaccatc agggaacatt          50

<210> SEQ ID NO 49
<211> LENGTH: 50
<212> TYPE: DNA
<213> ORGANISM: artificial sequence
<220> FEATURE:
<223> OTHER INFORMATION: synthesized

<400> SEQUENCE: 49
agacttagat ctgagccctc cctcttccca gcacaggcag gggtagaagc          50

<210> SEQ ID NO 50
<211> LENGTH: 50
<212> TYPE: DNA
<213> ORGANISM: artificial sequence
<220> FEATURE:
<223> OTHER INFORMATION: synthesized

<400> SEQUENCE: 50
```
agacttagat ctgagccctc cctcttccca gaacaggcag gggtagaagc        50

<210> SEQ ID NO 51
<211> LENGTH: 50
<212> TYPE: DNA
<213> ORGANISM: artificial sequence
<220> FEATURE:
<223> OTHER INFORMATION: synthesized

<400> SEQUENCE: 51
tgtgtttgga tttgcagtag gctgaagcgt tatactatga ctggagtcca        50

<210> SEQ ID NO 52
<211> LENGTH: 50
<212> TYPE: DNA
<213> ORGANISM: artificial sequence
<220> FEATURE:
<223> OTHER INFORMATION: synthesized

<400> SEQUENCE: 52
tgtgtttgga tttgcagtag gctgaagcgt tgtactatga ctggagtcca        50

<210> SEQ ID NO 53
<211> LENGTH: 50
<212> TYPE: DNA
<213> ORGANISM: artificial sequence
<220> FEATURE:
<223> OTHER INFORMATION: synthesized

<400> SEQUENCE: 53
aaaatagtgc tttttacttt tatctgaatg attgaaatgt ccttttccca        50

<210> SEQ ID NO 54
<211> LENGTH: 50
<212> TYPE: DNA
<213> ORGANISM: artificial sequence
<220> FEATURE:
<223> OTHER INFORMATION: synthesized

<400> SEQUENCE: 54
aaaatagtgc tttttacttt tatctgaatg actgaaatgt ccttttccca        50

<210> SEQ ID NO 55
<211> LENGTH: 50
<212> TYPE: DNA
<213> ORGANISM: artificial sequence
<220> FEATURE:
<223> OTHER INFORMATION: synthesized

<400> SEQUENCE: 55
gtcacgccac ttgacaggcg agtaacagac atggaccatc agtgaacatt        50

<210> SEQ ID NO 56
<211> LENGTH: 50
<212> TYPE: DNA
<213> ORGANISM: artificial sequence
<220> FEATURE:
<223> OTHER INFORMATION: synthesized

<400> SEQUENCE: 56
gtcacgccac ttgacaggcg agtaacagac atggaccatc agagaacatt        50

<210> SEQ ID NO 57
<211> LENGTH: 50
<212> TYPE: DNA

```
<213> ORGANISM: artificial sequence
<220> FEATURE:
<223> OTHER INFORMATION: synthesized

<400> SEQUENCE: 57
gtcacgccac ttgacaggcg agtaacagac atggaccatc aaggaacatt          50

<210> SEQ ID NO 58
<211> LENGTH: 50
<212> TYPE: DNA
<213> ORGANISM: artificial sequence
<220> FEATURE:
<223> OTHER INFORMATION: synthesized

<400> SEQUENCE: 58
gtcacgccac ttgacaggcg agtaacagac atggaccatc atggaacatt          50

<210> SEQ ID NO 59
<211> LENGTH: 50
<212> TYPE: DNA
<213> ORGANISM: artificial sequence
<220> FEATURE:
<223> OTHER INFORMATION: synthesized

<400> SEQUENCE: 59
gtcacgccac ttgacaggcg agtaacagac atggaccatc cgggaacatt          50

<210> SEQ ID NO 60
<211> LENGTH: 50
<212> TYPE: DNA
<213> ORGANISM: artificial sequence
<220> FEATURE:
<223> OTHER INFORMATION: synthesized

<400> SEQUENCE: 60
gtcacgccac ttgacaggcg agtaacagac atggaccatc ggggaacatt          50

<210> SEQ ID NO 61
<211> LENGTH: 50
<212> TYPE: DNA
<213> ORGANISM: artificial sequence
<220> FEATURE:
<223> OTHER INFORMATION: synthesized

<400> SEQUENCE: 61
gtcacgccac ttgacaggcg agtaacagac atggaccata agggaacatt          50

<210> SEQ ID NO 62
<211> LENGTH: 50
<212> TYPE: DNA
<213> ORGANISM: artificial sequence
<220> FEATURE:
<223> OTHER INFORMATION: synthesized

<400> SEQUENCE: 62
gtcacgccac ttgacaggcg agtaacagac atggaccatt agggaacatt          50

<210> SEQ ID NO 63
<211> LENGTH: 50
<212> TYPE: DNA
<213> ORGANISM: artificial sequence
<220> FEATURE:
<223> OTHER INFORMATION: synthesized

<400> SEQUENCE: 63
gtcacgccac ttgacaggcg agtaacagac atggaccacc agggaacatt          50
```

<210> SEQ ID NO 64
<211> LENGTH: 50
<212> TYPE: DNA
<213> ORGANISM: artificial sequence
<220> FEATURE:
<223> OTHER INFORMATION: synthesized

<400> SEQUENCE: 64
gtcacgccac ttgacaggcg agtaacagac atggaccagc agggaacatt         50

<210> SEQ ID NO 65
<211> LENGTH: 50
<212> TYPE: DNA
<213> ORGANISM: artificial sequence
<220> FEATURE:
<223> OTHER INFORMATION: synthesized

<400> SEQUENCE: 65
gtcacgccac ttgacaggcg agtaacagac atggaccctc agggaacatt         50

<210> SEQ ID NO 66
<211> LENGTH: 50
<212> TYPE: DNA
<213> ORGANISM: artificial sequence
<220> FEATURE:
<223> OTHER INFORMATION: synthesized

<400> SEQUENCE: 66
gtcacgccac ttgacaggcg agtaacagac atggaccgtc agggaacatt         50

<210> SEQ ID NO 67
<211> LENGTH: 50
<212> TYPE: DNA
<213> ORGANISM: artificial sequence
<220> FEATURE:
<223> OTHER INFORMATION: synthesized

<400> SEQUENCE: 67
gtcacgccac ttgacaggcg agtaacagac atggacaatc agggaacatt         50

<210> SEQ ID NO 68
<211> LENGTH: 50
<212> TYPE: DNA
<213> ORGANISM: artificial sequence
<220> FEATURE:
<223> OTHER INFORMATION: synthesized

<400> SEQUENCE: 68
gtcacgccac ttgacaggcg agtaacagac atggactatc agggaacatt         50

<210> SEQ ID NO 69
<211> LENGTH: 50
<212> TYPE: DNA
<213> ORGANISM: artificial sequence
<220> FEATURE:
<223> OTHER INFORMATION: synthesized

<400> SEQUENCE: 69
gtcacgccac ttgacaggcg agtaacagac atggaacatc agggaacatt         50

<210> SEQ ID NO 70
<211> LENGTH: 50
<212> TYPE: DNA
<213> ORGANISM: artificial sequence
<220> FEATURE:

<223> OTHER INFORMATION: synthesized

<400> SEQUENCE: 70
gtcacgccac ttgacaggcg agtaacagac atggatcatc agggaacatt          50

<210> SEQ ID NO 71
<211> LENGTH: 50
<212> TYPE: DNA
<213> ORGANISM: artificial sequence
<220> FEATURE:
<223> OTHER INFORMATION: synthesized

<400> SEQUENCE: 71
gtcacgccac ttgacaggcg agtaacagac atggcccatc agggaacatt          50

<210> SEQ ID NO 72
<211> LENGTH: 50
<212> TYPE: DNA
<213> ORGANISM: artificial sequence
<220> FEATURE:
<223> OTHER INFORMATION: synthesized

<400> SEQUENCE: 72
gtcacgccac ttgacaggcg agtaacagac atgggccatc agggaacatt          50

<210> SEQ ID NO 73
<211> LENGTH: 50
<212> TYPE: DNA
<213> ORGANISM: artificial sequence
<220> FEATURE:
<223> OTHER INFORMATION: synthesized

<400> SEQUENCE: 73
gtcacgccac ttgacaggcg agtaacagac atgaaccatc agggaacatt          50

<210> SEQ ID NO 74
<211> LENGTH: 50
<212> TYPE: DNA
<213> ORGANISM: artificial sequence
<220> FEATURE:
<223> OTHER INFORMATION: synthesized

<400> SEQUENCE: 74
gtcacgccac ttgacaggcg agtaacagac atgtaccatc agggaacatt          50

<210> SEQ ID NO 75
<211> LENGTH: 50
<212> TYPE: DNA
<213> ORGANISM: artificial sequence
<220> FEATURE:
<223> OTHER INFORMATION: synthesized

<400> SEQUENCE: 75
gtcacgccac ttgacaggcg agtaacagac atagaccatc agggaacatt          50

<210> SEQ ID NO 76
<211> LENGTH: 50
<212> TYPE: DNA
<213> ORGANISM: artificial sequence
<220> FEATURE:
<223> OTHER INFORMATION: synthesized

<400> SEQUENCE: 76
gtcacgccac ttgacaggcg agtaacagac attgaccatc agggaacatt          50

-continued

<210> SEQ ID NO 77
<211> LENGTH: 50
<212> TYPE: DNA
<213> ORGANISM: artificial sequence
<220> FEATURE:
<223> OTHER INFORMATION: synthesized

<400> SEQUENCE: 77
gtcacgccac ttgacaggcg agtaacagac acggaccatc agggaacatt           50

<210> SEQ ID NO 78
<211> LENGTH: 50
<212> TYPE: DNA
<213> ORGANISM: artificial sequence
<220> FEATURE:
<223> OTHER INFORMATION: synthesized

<400> SEQUENCE: 78
gtcacgccac ttgacaggcg agtaacagac agggaccatc agggaacatt           50

<210> SEQ ID NO 79
<211> LENGTH: 50
<212> TYPE: DNA
<213> ORGANISM: artificial sequence
<220> FEATURE:
<223> OTHER INFORMATION: synthesized

<400> SEQUENCE: 79
gtcacgccac ttgacaggcg agtaacagac ctggaccatc agggaacatt           50

<210> SEQ ID NO 80
<211> LENGTH: 50
<212> TYPE: DNA
<213> ORGANISM: artificial sequence
<220> FEATURE:
<223> OTHER INFORMATION: synthesized

<400> SEQUENCE: 80
gtcacgccac ttgacaggcg agtaacagac gtggaccatc agggaacatt           50

<210> SEQ ID NO 81
<211> LENGTH: 50
<212> TYPE: DNA
<213> ORGANISM: artificial sequence
<220> FEATURE:
<223> OTHER INFORMATION: synthesized

<400> SEQUENCE: 81
gtcacgccac ttgacaggcg agtaacagaa atggaccatc agggaacatt           50

<210> SEQ ID NO 82
<211> LENGTH: 50
<212> TYPE: DNA
<213> ORGANISM: artificial sequence
<220> FEATURE:
<223> OTHER INFORMATION: synthesized

<400> SEQUENCE: 82
gtcacgccac ttgacaggcg agtaacagat atggaccatc agggaacatt           50

<210> SEQ ID NO 83
<211> LENGTH: 50
<212> TYPE: DNA
<213> ORGANISM: artificial sequence
<220> FEATURE:
<223> OTHER INFORMATION: synthesized

<400> SEQUENCE: 83
gtcacgccac ttgacaggcg agtaacagcc atggaccatc agggaacatt            50

<210> SEQ ID NO 84
<211> LENGTH: 50
<212> TYPE: DNA
<213> ORGANISM: artificial sequence
<220> FEATURE:
<223> OTHER INFORMATION: synthesized

<400> SEQUENCE: 84
gtcacgccac ttgacaggcg agtaacaggc atggaccatc agggaacatt            50

<210> SEQ ID NO 85
<211> LENGTH: 50
<212> TYPE: DNA
<213> ORGANISM: artificial sequence
<220> FEATURE:
<223> OTHER INFORMATION: synthesized

<400> SEQUENCE: 85
gtcacgccac ttgacaggcg agtaacaaac atggaccatc agggaacatt            50

<210> SEQ ID NO 86
<211> LENGTH: 50
<212> TYPE: DNA
<213> ORGANISM: artificial sequence
<220> FEATURE:
<223> OTHER INFORMATION: synthesized

<400> SEQUENCE: 86
gtcacgccac ttgacaggcg agtaacatac atggaccatc agggaacatt            50

<210> SEQ ID NO 87
<211> LENGTH: 50
<212> TYPE: DNA
<213> ORGANISM: artificial sequence
<220> FEATURE:
<223> OTHER INFORMATION: synthesized

<400> SEQUENCE: 87
agacttagat ctgagccctc cctcttccca gcacacgcag gggtagaagc            50

<210> SEQ ID NO 88
<211> LENGTH: 50
<212> TYPE: DNA
<213> ORGANISM: artificial sequence
<220> FEATURE:
<223> OTHER INFORMATION: synthesized

<400> SEQUENCE: 88
agacttagat ctgagccctc cctcttccca gcactggcag gggtagaagc            50

<210> SEQ ID NO 89
<211> LENGTH: 50
<212> TYPE: DNA
<213> ORGANISM: artificial sequence
<220> FEATURE:
<223> OTHER INFORMATION: synthesized

<400> SEQUENCE: 89
agacttagat ctgagccctc cctcttccca gcagaggcag gggtagaagc            50

<210> SEQ ID NO 90
<211> LENGTH: 50

<212> TYPE: DNA
<213> ORGANISM: artificial sequence
<220> FEATURE:
<223> OTHER INFORMATION: synthesized

<400> SEQUENCE: 90
agacttagat ctgagccctc cctcttccca gctcaggcag gggtagaagc                50

<210> SEQ ID NO 91
<211> LENGTH: 50
<212> TYPE: DNA
<213> ORGANISM: artificial sequence
<220> FEATURE:
<223> OTHER INFORMATION: synthesized

<400> SEQUENCE: 91
agacttagat ctgagccctc cctcttccca ggacaggcag gggtagaagc                50

<210> SEQ ID NO 92
<211> LENGTH: 50
<212> TYPE: DNA
<213> ORGANISM: artificial sequence
<220> FEATURE:
<223> OTHER INFORMATION: synthesized

<400> SEQUENCE: 92
agacttagat ctgagccctc cctcttccca ccacaggcag gggtagaagc                50

<210> SEQ ID NO 93
<211> LENGTH: 50
<212> TYPE: DNA
<213> ORGANISM: artificial sequence
<220> FEATURE:
<223> OTHER INFORMATION: synthesized

<400> SEQUENCE: 93
agacttagat ctgagccctc cctcttccct gcacaggcag gggtagaagc                50

<210> SEQ ID NO 94
<211> LENGTH: 50
<212> TYPE: DNA
<213> ORGANISM: artificial sequence
<220> FEATURE:
<223> OTHER INFORMATION: synthesized

<400> SEQUENCE: 94
agacttagat ctgagccctc cctcttccga gcacaggcag gggtagaagc                50

<210> SEQ ID NO 95
<211> LENGTH: 50
<212> TYPE: DNA
<213> ORGANISM: artificial sequence
<220> FEATURE:
<223> OTHER INFORMATION: synthesized

<400> SEQUENCE: 95
agacttagat ctgagccctc cctcttcgca gcacaggcag gggtagaagc                50

<210> SEQ ID NO 96
<211> LENGTH: 50
<212> TYPE: DNA
<213> ORGANISM: artificial sequence
<220> FEATURE:
<223> OTHER INFORMATION: synthesized

<400> SEQUENCE: 96
tgtgtttgga tttgcagtag gctgaagcgt tatacaatga ctggagtcca            50

<210> SEQ ID NO 97
<211> LENGTH: 50
<212> TYPE: DNA
<213> ORGANISM: artificial sequence
<220> FEATURE:
<223> OTHER INFORMATION: synthesized

<400> SEQUENCE: 97
tgtgtttgga tttgcagtag gctgaagcgt tatagtatga ctggagtcca            50

<210> SEQ ID NO 98
<211> LENGTH: 50
<212> TYPE: DNA
<213> ORGANISM: artificial sequence
<220> FEATURE:
<223> OTHER INFORMATION: synthesized

<400> SEQUENCE: 98
tgtgtttgga tttgcagtag gctgaagcgt tattctatga ctggagtcca            50

<210> SEQ ID NO 99
<211> LENGTH: 50
<212> TYPE: DNA
<213> ORGANISM: artificial sequence
<220> FEATURE:
<223> OTHER INFORMATION: synthesized

<400> SEQUENCE: 99
tgtgtttgga tttgcagtag gctgaagcgt taaactatga ctggagtcca            50

<210> SEQ ID NO 100
<211> LENGTH: 50
<212> TYPE: DNA
<213> ORGANISM: artificial sequence
<220> FEATURE:
<223> OTHER INFORMATION: synthesized

<400> SEQUENCE: 100
tgtgtttgga tttgcagtag gctgaagcgt tttactatga ctggagtcca            50

<210> SEQ ID NO 101
<211> LENGTH: 50
<212> TYPE: DNA
<213> ORGANISM: artificial sequence
<220> FEATURE:
<223> OTHER INFORMATION: synthesized

<400> SEQUENCE: 101
tgtgtttgga tttgcagtag gctgaagcgt aatactatga ctggagtcca            50

<210> SEQ ID NO 102
<211> LENGTH: 50
<212> TYPE: DNA
<213> ORGANISM: artificial sequence
<220> FEATURE:
<223> OTHER INFORMATION: synthesized

<400> SEQUENCE: 102
tgtgtttgga tttgcagtag gctgaagcga tatactatga ctggagtcca            50

<210> SEQ ID NO 103
<211> LENGTH: 50
<212> TYPE: DNA
<213> ORGANISM: artificial sequence

```
<220> FEATURE:
<223> OTHER INFORMATION: synthesized

<400> SEQUENCE: 103
tgtgtttgga tttgcagtag gctgaagcct tatactatga ctggagtcca          50

<210> SEQ ID NO 104
<211> LENGTH: 50
<212> TYPE: DNA
<213> ORGANISM: artificial sequence
<220> FEATURE:
<223> OTHER INFORMATION: synthesized

<400> SEQUENCE: 104
tgtgtttgga tttgcagtag gctgaagggt tatactatga ctggagtcca          50

<210> SEQ ID NO 105
<211> LENGTH: 50
<212> TYPE: DNA
<213> ORGANISM: artificial sequence
<220> FEATURE:
<223> OTHER INFORMATION: synthesized

<400> SEQUENCE: 105
aaaatagtgc ttttactttt tatctgaatg attgatatgt cctttcccca          50

<210> SEQ ID NO 106
<211> LENGTH: 50
<212> TYPE: DNA
<213> ORGANISM: artificial sequence
<220> FEATURE:
<223> OTHER INFORMATION: synthesized

<400> SEQUENCE: 106
aaaatagtgc ttttactttt tatctgaatg attgtaatgt cctttcccca          50

<210> SEQ ID NO 107
<211> LENGTH: 50
<212> TYPE: DNA
<213> ORGANISM: artificial sequence
<220> FEATURE:
<223> OTHER INFORMATION: synthesized

<400> SEQUENCE: 107
aaaatagtgc ttttactttt tatctgaatg attcaaatgt cctttcccca          50

<210> SEQ ID NO 108
<211> LENGTH: 50
<212> TYPE: DNA
<213> ORGANISM: artificial sequence
<220> FEATURE:
<223> OTHER INFORMATION: synthesized

<400> SEQUENCE: 108
aaaatagtgc ttttactttt tatctgaatg atagaaatgt cctttcccca          50

<210> SEQ ID NO 109
<211> LENGTH: 50
<212> TYPE: DNA
<213> ORGANISM: artificial sequence
<220> FEATURE:
<223> OTHER INFORMATION: synthesized

<400> SEQUENCE: 109
aaaatagtgc ttttactttt tatctgaatg aatgaaatgt cctttcccca          50
```

<210> SEQ ID NO 110
<211> LENGTH: 50
<212> TYPE: DNA
<213> ORGANISM: artificial sequence
<220> FEATURE:
<223> OTHER INFORMATION: synthesized

<400> SEQUENCE: 110
aaaatagtgc ttttactttt tatctgaatg tttgaaatgt cctttccca          50

<210> SEQ ID NO 111
<211> LENGTH: 50
<212> TYPE: DNA
<213> ORGANISM: artificial sequence
<220> FEATURE:
<223> OTHER INFORMATION: synthesized

<400> SEQUENCE: 111
aaaatagtgc ttttactttt tatctgaatc attgaaatgt cctttccca          50

<210> SEQ ID NO 112
<211> LENGTH: 50
<212> TYPE: DNA
<213> ORGANISM: artificial sequence
<220> FEATURE:
<223> OTHER INFORMATION: synthesized

<400> SEQUENCE: 112
aaaatagtgc ttttactttt tatctgaaag attgaaatgt cctttccca          50

<210> SEQ ID NO 113
<211> LENGTH: 50
<212> TYPE: DNA
<213> ORGANISM: artificial sequence
<220> FEATURE:
<223> OTHER INFORMATION: synthesized

<400> SEQUENCE: 113
aaaatagtgc ttttactttt tatctgattg attgaaatgt cctttccca          50

<210> SEQ ID NO 114
<211> LENGTH: 50
<212> TYPE: DNA
<213> ORGANISM: artificial sequence
<220> FEATURE:
<223> OTHER INFORMATION: synthesized

<400> SEQUENCE: 114
ggatctcctg gcggaggtgg tggtagaagg tccaggagca ggggtagccg          50

<210> SEQ ID NO 115
<211> LENGTH: 50
<212> TYPE: DNA
<213> ORGANISM: artificial sequence
<220> FEATURE:
<223> OTHER INFORMATION: synthesized

<400> SEQUENCE: 115
ggatctcctg gcggaggtgg tggtagaagg tctaggagca ggggtagccg          50

<210> SEQ ID NO 116
<211> LENGTH: 50
<212> TYPE: DNA
<213> ORGANISM: artificial sequence
<220> FEATURE:
<223> OTHER INFORMATION: synthesized

```
<400> SEQUENCE: 116
agcacatgtt tgttgaatga gtcagtggat gacgtagatc agtatcttgt           50

<210> SEQ ID NO 117
<211> LENGTH: 50
<212> TYPE: DNA
<213> ORGANISM: artificial sequence
<220> FEATURE:
<223> OTHER INFORMATION: synthesized

<400> SEQUENCE: 117
agcacatgtt tgttgaatga gtcagtggat gatgtagatc agtatcttgt           50

<210> SEQ ID NO 118
<211> LENGTH: 50
<212> TYPE: DNA
<213> ORGANISM: artificial sequence
<220> FEATURE:
<223> OTHER INFORMATION: synthesized

<400> SEQUENCE: 118
gcttctttcc ctgcctgtgc tgggaagagg gagggctcag atctaagtct           50

<210> SEQ ID NO 119
<211> LENGTH: 50
<212> TYPE: DNA
<213> ORGANISM: artificial sequence
<220> FEATURE:
<223> OTHER INFORMATION: synthesized

<400> SEQUENCE: 119
agacttagat ctgagccctc cctcttccca gcacaggcag ggaaagaagc           50

<210> SEQ ID NO 120
<211> LENGTH: 50
<212> TYPE: DNA
<213> ORGANISM: artificial sequence
<220> FEATURE:
<223> OTHER INFORMATION: synthesized

<400> SEQUENCE: 120
gcttctttcc ctgcctgttc tgggaagagg gagggctcag atctaagtct           50

<210> SEQ ID NO 121
<211> LENGTH: 50
<212> TYPE: DNA
<213> ORGANISM: artificial sequence
<220> FEATURE:
<223> OTHER INFORMATION: synthesized

<400> SEQUENCE: 121
agacttagat ctgagccctc cctcttccca gaacaggcag ggaaagaagc           50

<210> SEQ ID NO 122
<211> LENGTH: 50
<212> TYPE: DNA
<213> ORGANISM: artificial sequence
<220> FEATURE:
<223> OTHER INFORMATION: synthesized

<400> SEQUENCE: 122
gcttttaccc ctgcctgtgc tgggaagagg gagggctcag atctaagtct           50

<210> SEQ ID NO 123
```

```
<211> LENGTH: 50
<212> TYPE: DNA
<213> ORGANISM: artificial sequence
<220> FEATURE:
<223> OTHER INFORMATION: synthesized

<400> SEQUENCE: 123
agacttagat ctgagccctc cctcttccca gcacaggcag gggtaaaagc         50

<210> SEQ ID NO 124
<211> LENGTH: 50
<212> TYPE: DNA
<213> ORGANISM: artificial sequence
<220> FEATURE:
<223> OTHER INFORMATION: synthesized

<400> SEQUENCE: 124
gcttttaccc ctgcctgttc tgggaagagg gagggctcag atctaagtct         50

<210> SEQ ID NO 125
<211> LENGTH: 50
<212> TYPE: DNA
<213> ORGANISM: artificial sequence
<220> FEATURE:
<223> OTHER INFORMATION: synthesized

<400> SEQUENCE: 125
agacttagat ctgagccctc cctcttccca gaacaggcag gggtaaaagc         50

<210> SEQ ID NO 126
<211> LENGTH: 12
<212> TYPE: DNA
<213> ORGANISM: artificial sequence
<220> FEATURE:
<223> OTHER INFORMATION: synthesized
<220> FEATURE:
<221> NAME/KEY: misc_feature
<222> LOCATION: (1)..(12)
<223> OTHER INFORMATION: n is a, c, g, or t

<400> SEQUENCE: 126
nnnnnnnnnn nn                                                  12

<210> SEQ ID NO 127
<211> LENGTH: 41
<212> TYPE: DNA
<213> ORGANISM: artificial sequence
<220> FEATURE:
<223> OTHER INFORMATION: synthesized

<400> SEQUENCE: 127
ctaccgtaat actaaaagtg ccacttctca gatttgagaa g                  41

<210> SEQ ID NO 128
<211> LENGTH: 25
<212> TYPE: DNA
<213> ORGANISM: artificial sequence
<220> FEATURE:
<223> OTHER INFORMATION: synthesized

<400> SEQUENCE: 128
gaaattaata cgactcacta taggg                                    25

<210> SEQ ID NO 129
<211> LENGTH: 68
<212> TYPE: DNA
<213> ORGANISM: artificial sequence
```

```
<220> FEATURE:
<223> OTHER INFORMATION: synthesized

<400> SEQUENCE: 129
tcgcgcttgt cgcgcagacg aatgatctac aacagtagaa attccctata gtgagtcgta    60
ttaatttc                                                             68

<210> SEQ ID NO 130
<211> LENGTH: 23
<212> TYPE: DNA
<213> ORGANISM: artificial sequence
<220> FEATURE:
<223> OTHER INFORMATION: synthesized

<400> SEQUENCE: 130
aacagacatg gaccatcagg gtg                                            23

<210> SEQ ID NO 131
<211> LENGTH: 21
<212> TYPE: DNA
<213> ORGANISM: artificial sequence
<220> FEATURE:
<223> OTHER INFORMATION: synthesized

<400> SEQUENCE: 131
catggaccat cagggtgcca c                                              21

<210> SEQ ID NO 132
<211> LENGTH: 22
<212> TYPE: DNA
<213> ORGANISM: artificial sequence
<220> FEATURE:
<223> OTHER INFORMATION: synthesized

<400> SEQUENCE: 132
acatggacca tcagggtgcc ac                                             22

<210> SEQ ID NO 133
<211> LENGTH: 21
<212> TYPE: DNA
<213> ORGANISM: artificial sequence
<220> FEATURE:
<223> OTHER INFORMATION: synthesized

<400> SEQUENCE: 133
gacatggacc atcagggtgc c                                              21

<210> SEQ ID NO 134
<211> LENGTH: 21
<212> TYPE: DNA
<213> ORGANISM: artificial sequence
<220> FEATURE:
<223> OTHER INFORMATION: synthesized

<400> SEQUENCE: 134
agacatggac catcagggtg c                                              21

<210> SEQ ID NO 135
<211> LENGTH: 21
<212> TYPE: DNA
<213> ORGANISM: artificial sequence
<220> FEATURE:
<223> OTHER INFORMATION: synthesized

<400> SEQUENCE: 135
```
cagacatgga ccatcagggt g         21

<210> SEQ ID NO 136
<211> LENGTH: 22
<212> TYPE: DNA
<213> ORGANISM: artificial sequence
<220> FEATURE:
<223> OTHER INFORMATION: synthesized

<400> SEQUENCE: 136
acagacatgg accatcaggg tg        22

<210> SEQ ID NO 137
<211> LENGTH: 40
<212> TYPE: DNA
<213> ORGANISM: artificial sequence
<220> FEATURE:
<223> OTHER INFORMATION: synthesized

<400> SEQUENCE: 137
ccagcacagg caggggtgc cacttctcag atttgagaag         40

<210> SEQ ID NO 138
<211> LENGTH: 40
<212> TYPE: DNA
<213> ORGANISM: artificial sequence
<220> FEATURE:
<223> OTHER INFORMATION: synthesized

<400> SEQUENCE: 138
cgttatacta tgactggtgc cacttctcag atttgagaag         40

<210> SEQ ID NO 139
<211> LENGTH: 40
<212> TYPE: DNA
<213> ORGANISM: artificial sequence
<220> FEATURE:
<223> OTHER INFORMATION: synthesized

<400> SEQUENCE: 139
atgattgaaa tgtcctgtgc cacttctcag atttgagaag         40

<210> SEQ ID NO 140
<211> LENGTH: 40
<212> TYPE: DNA
<213> ORGANISM: artificial sequence
<220> FEATURE:
<223> OTHER INFORMATION: synthesized

<400> SEQUENCE: 140
ccagaacagg caggggtgc cacttctcag atttgagaag         40

<210> SEQ ID NO 141
<211> LENGTH: 40
<212> TYPE: DNA
<213> ORGANISM: artificial sequence
<220> FEATURE:
<223> OTHER INFORMATION: synthesized

<400> SEQUENCE: 141
cgttgtacta tgactggtgc cacttctcag atttgagaag         40

<210> SEQ ID NO 142
<211> LENGTH: 40
<212> TYPE: DNA
<213> ORGANISM: artificial sequence

```
<220> FEATURE:
<223> OTHER INFORMATION: synthesized

<400> SEQUENCE: 142
atgactgaaa tgtcctgtgc cacttctcag atttgagaag                    40

<210> SEQ ID NO 143
<211> LENGTH: 40
<212> TYPE: DNA
<213> ORGANISM: artificial sequence
<220> FEATURE:
<223> OTHER INFORMATION: synthesized

<400> SEQUENCE: 143
aggtccagga gcagggttgc cacttctcag atttgagaag                    40

<210> SEQ ID NO 144
<211> LENGTH: 40
<212> TYPE: DNA
<213> ORGANISM: artificial sequence
<220> FEATURE:
<223> OTHER INFORMATION: synthesized

<400> SEQUENCE: 144
aggtctagga gcagggttgc cacttctcag atttgagaag                    40

<210> SEQ ID NO 145
<211> LENGTH: 40
<212> TYPE: DNA
<213> ORGANISM: artificial sequence
<220> FEATURE:
<223> OTHER INFORMATION: synthesized

<400> SEQUENCE: 145
gatgacgtag atcagtgtgc cacttctcag atttgagaag                    40

<210> SEQ ID NO 146
<211> LENGTH: 40
<212> TYPE: DNA
<213> ORGANISM: artificial sequence
<220> FEATURE:
<223> OTHER INFORMATION: synthesized

<400> SEQUENCE: 146
gatgatgtag atcagtgtgc cacttctcag atttgagaag                    40

<210> SEQ ID NO 147
<211> LENGTH: 44
<212> TYPE: DNA
<213> ORGANISM: artificial sequence
<220> FEATURE:
<223> OTHER INFORMATION: synthesized

<400> SEQUENCE: 147
atatcttcta cttctccact gtgccacttc tcagatttga gaag               44

<210> SEQ ID NO 148
<211> LENGTH: 44
<212> TYPE: DNA
<213> ORGANISM: artificial sequence
<220> FEATURE:
<223> OTHER INFORMATION: synthesized

<400> SEQUENCE: 148
tctagagaat cccagaatgc gtgccacttc tcagatttga gaag               44
```

<210> SEQ ID NO 149
<211> LENGTH: 40
<212> TYPE: DNA
<213> ORGANISM: artificial sequence
<220> FEATURE:
<223> OTHER INFORMATION: synthesized

<400> SEQUENCE: 149
gcgttatact atgactgtgc cacttctcag atttgagaag                              40

<210> SEQ ID NO 150
<211> LENGTH: 40
<212> TYPE: DNA
<213> ORGANISM: artificial sequence
<220> FEATURE:
<223> OTHER INFORMATION: synthesized

<400> SEQUENCE: 150
gcgttgtact atgactgtgc cacttctcag atttgagaag                              40

<210> SEQ ID NO 151
<211> LENGTH: 42
<212> TYPE: DNA
<213> ORGANISM: artificial sequence
<220> FEATURE:
<223> OTHER INFORMATION: synthesized

<400> SEQUENCE: 151
cttcccagca caggcagggt gccacttctc agatttgaga ag                           42

<210> SEQ ID NO 152
<211> LENGTH: 42
<212> TYPE: DNA
<213> ORGANISM: artificial sequence
<220> FEATURE:
<223> OTHER INFORMATION: synthesized

<400> SEQUENCE: 152
cttcccagaa caggcagggt gccacttctc agatttgaga ag                           42

<210> SEQ ID NO 153
<211> LENGTH: 42
<212> TYPE: DNA
<213> ORGANISM: artificial sequence
<220> FEATURE:
<223> OTHER INFORMATION: synthesized

<400> SEQUENCE: 153
tcccagcaca ggcaggggt gccacttctc agatttgaga ag                            42

<210> SEQ ID NO 154
<211> LENGTH: 42
<212> TYPE: DNA
<213> ORGANISM: artificial sequence
<220> FEATURE:
<223> OTHER INFORMATION: synthesized

<400> SEQUENCE: 154
tcccagaaca ggcaggggt gccacttctc agatttgaga ag                            42

<210> SEQ ID NO 155
<211> LENGTH: 44
<212> TYPE: DNA
<213> ORGANISM: artificial sequence
<220> FEATURE:
<223> OTHER INFORMATION: synthesized

```
<400> SEQUENCE: 155
tgtgatccaa gacattcccc gtgccacttc tcagatttga gaag          44

<210> SEQ ID NO 156
<211> LENGTH: 44
<212> TYPE: DNA
<213> ORGANISM: artificial sequence
<220> FEATURE:
<223> OTHER INFORMATION: synthesized

<400> SEQUENCE: 156
ctcgtcagtg ctctcctctc gtgccacttc tcagatttga gaag          44

<210> SEQ ID NO 157
<211> LENGTH: 43
<212> TYPE: DNA
<213> ORGANISM: artificial sequence
<220> FEATURE:
<223> OTHER INFORMATION: synthesized

<400> SEQUENCE: 157
tcttcccagc acaggcaggg tgccacttct cagatttgag aag           43

<210> SEQ ID NO 158
<211> LENGTH: 43
<212> TYPE: DNA
<213> ORGANISM: artificial sequence
<220> FEATURE:
<223> OTHER INFORMATION: synthesized

<400> SEQUENCE: 158
tcttcccaga acaggcaggg tgccacttct cagatttgag aag           43

<210> SEQ ID NO 159
<211> LENGTH: 43
<212> TYPE: DNA
<213> ORGANISM: artificial sequence
<220> FEATURE:
<223> OTHER INFORMATION: synthesized

<400> SEQUENCE: 159
ttcccagcac aggcaggggg tgccacttct cagatttgag aag           43

<210> SEQ ID NO 160
<211> LENGTH: 43
<212> TYPE: DNA
<213> ORGANISM: artificial sequence
<220> FEATURE:
<223> OTHER INFORMATION: synthesized

<400> SEQUENCE: 160
ttcccagaac aggcaggggg tgccacttct cagatttgag aag           43

<210> SEQ ID NO 161
<211> LENGTH: 20
<212> TYPE: DNA
<213> ORGANISM: artificial sequence
<220> FEATURE:
<223> OTHER INFORMATION: synthesized

<400> SEQUENCE: 161
gtgaacgttc ccttagcact                                     20

<210> SEQ ID NO 162
```

```
<211> LENGTH: 19
<212> TYPE: DNA
<213> ORGANISM: artificial sequence
<220> FEATURE:
<223> OTHER INFORMATION: synthesized

<400> SEQUENCE: 162
gggagggcag aactagtcc                                                      19

<210> SEQ ID NO 163
<211> LENGTH: 41
<212> TYPE: DNA
<213> ORGANISM: artificial sequence
<220> FEATURE:
<223> OTHER INFORMATION: synthesized

<400> SEQUENCE: 163
cgccacttga caggcgagta actgccactt attgggtcag c                             41

<210> SEQ ID NO 164
<211> LENGTH: 39
<212> TYPE: DNA
<213> ORGANISM: artificial sequence
<220> FEATURE:
<223> OTHER INFORMATION: synthesized

<400> SEQUENCE: 164
gcgtgttccc cagagtgact tagcagcttc ctcctcctt                                39

<210> SEQ ID NO 165
<211> LENGTH: 22
<212> TYPE: DNA
<213> ORGANISM: artificial sequence
<220> FEATURE:
<223> OTHER INFORMATION: synthesized

<400> SEQUENCE: 165
aggaaacatt aacgtactga tg                                                  22

<210> SEQ ID NO 166
<211> LENGTH: 21
<212> TYPE: DNA
<213> ORGANISM: artificial sequence
<220> FEATURE:
<223> OTHER INFORMATION: synthesized

<400> SEQUENCE: 166
ttccttttat ttcccttcag c                                                   21

<210> SEQ ID NO 167
<211> LENGTH: 18
<212> TYPE: DNA
<213> ORGANISM: artificial sequence
<220> FEATURE:
<223> OTHER INFORMATION: synthesized

<400> SEQUENCE: 167
cgacggcaaa gaagacca                                                       18

<210> SEQ ID NO 168
<211> LENGTH: 18
<212> TYPE: DNA
<213> ORGANISM: artificial sequence
<220> FEATURE:
<223> OTHER INFORMATION: synthesized

<400> SEQUENCE: 168
```
agcctgccag gtgagtac                                         18

<210> SEQ ID NO 169
<211> LENGTH: 40
<212> TYPE: DNA
<213> ORGANISM: artificial sequence
<220> FEATURE:
<223> OTHER INFORMATION: synthesized

<400> SEQUENCE: 169
cgggtggatc ggcgttttgt tcactatgaa ggcggcatca                 40

<210> SEQ ID NO 170
<211> LENGTH: 40
<212> TYPE: DNA
<213> ORGANISM: artificial sequence
<220> FEATURE:
<223> OTHER INFORMATION: synthesized

<400> SEQUENCE: 170
gtattggcgt cgaagtggcg ttcgctgcgg aatgttgttg                 40

<210> SEQ ID NO 171
<211> LENGTH: 22
<212> TYPE: DNA
<213> ORGANISM: artificial sequence
<220> FEATURE:
<223> OTHER INFORMATION: synthesized

<400> SEQUENCE: 171
ttgttcagat attcaacgaa cg                                    22

<210> SEQ ID NO 172
<211> LENGTH: 20
<212> TYPE: DNA
<213> ORGANISM: artificial sequence
<220> FEATURE:
<223> OTHER INFORMATION: synthesized

<400> SEQUENCE: 172
gtggaacgat ggcttccagg                                       20

<210> SEQ ID NO 173
<211> LENGTH: 19
<212> TYPE: DNA
<213> ORGANISM: artificial sequence
<220> FEATURE:
<223> OTHER INFORMATION: synthesized

<400> SEQUENCE: 173
tctctgtgca tggcctgta                                        19

<210> SEQ ID NO 174
<211> LENGTH: 20
<212> TYPE: DNA
<213> ORGANISM: artificial sequence
<220> FEATURE:
<223> OTHER INFORMATION: synthesized

<400> SEQUENCE: 174
aacagtaaag gcaacgtcca                                       20

<210> SEQ ID NO 175
<211> LENGTH: 40
<212> TYPE: DNA

<213> ORGANISM: artificial sequence
<220> FEATURE:
<223> OTHER INFORMATION: synthesized

<400> SEQUENCE: 175
gcagctggga taccagtgga agtgcctcct ggaagaatgg                          40

<210> SEQ ID NO 176
<211> LENGTH: 40
<212> TYPE: DNA
<213> ORGANISM: artificial sequence
<220> FEATURE:
<223> OTHER INFORMATION: synthesized

<400> SEQUENCE: 176
tctctagagc catcttgcgc ctgaagcgac ccatgaacgc                          40

<210> SEQ ID NO 177
<211> LENGTH: 22
<212> TYPE: DNA
<213> ORGANISM: artificial sequence
<220> FEATURE:
<223> OTHER INFORMATION: synthesized

<400> SEQUENCE: 177
tgcttactga agccgaaaaa tg                                             22

<210> SEQ ID NO 178
<211> LENGTH: 21
<212> TYPE: DNA
<213> ORGANISM: artificial sequence
<220> FEATURE:
<223> OTHER INFORMATION: synthesized

<400> SEQUENCE: 178
tgatcgcgag accacacgat g                                              21

<210> SEQ ID NO 179
<211> LENGTH: 20
<212> TYPE: DNA
<213> ORGANISM: artificial sequence
<220> FEATURE:
<223> OTHER INFORMATION: synthesized

<400> SEQUENCE: 179
ggtttcggat gttacagcgt                                                20

<210> SEQ ID NO 180
<211> LENGTH: 35
<212> TYPE: DNA
<213> ORGANISM: artificial sequence
<220> FEATURE:
<223> OTHER INFORMATION: synthesized

<400> SEQUENCE: 180
caagcacccc acccgctcac ccacctcctc ctttg                               35

<210> SEQ ID NO 181
<211> LENGTH: 43
<212> TYPE: DNA
<213> ORGANISM: artificial sequence
<220> FEATURE:
<223> OTHER INFORMATION: synthesized

<400> SEQUENCE: 181
ggtttcggat gttacagcgt gtgctggaag acttagatct gag                      43

<210> SEQ ID NO 182
<211> LENGTH: 19
<212> TYPE: DNA
<213> ORGANISM: artificial sequence
<220> FEATURE:
<223> OTHER INFORMATION: synthesized

<400> SEQUENCE: 182
gctggaaagg tcaagggac                                                19

<210> SEQ ID NO 183
<211> LENGTH: 19
<212> TYPE: DNA
<213> ORGANISM: artificial sequence
<220> FEATURE:
<223> OTHER INFORMATION: synthesized

<400> SEQUENCE: 183
ggggtttgtt gcacagtcc                                                19

<210> SEQ ID NO 184
<211> LENGTH: 40
<212> TYPE: DNA
<213> ORGANISM: artificial sequence
<220> FEATURE:
<223> OTHER INFORMATION: synthesized

<400> SEQUENCE: 184
ggtagaagca aaggcaggag gtttgcccaa ggtcacacag                         40

<210> SEQ ID NO 185
<211> LENGTH: 40
<212> TYPE: DNA
<213> ORGANISM: artificial sequence
<220> FEATURE:
<223> OTHER INFORMATION: synthesized

<400> SEQUENCE: 185
gaaagaagca aaggcaggag gtttgcccaa ggtcacacag                         40

<210> SEQ ID NO 186
<211> LENGTH: 41
<212> TYPE: DNA
<213> ORGANISM: artificial sequence
<220> FEATURE:
<223> OTHER INFORMATION: synthesized

<400> SEQUENCE: 186
ctgggaagag ggagggctca gtgttgccac actttcactg g                       41

<210> SEQ ID NO 187
<211> LENGTH: 18
<212> TYPE: DNA
<213> ORGANISM: artificial sequence
<220> FEATURE:
<223> OTHER INFORMATION: synthesized

<400> SEQUENCE: 187
gtgagcgggt ggggtgct                                                 18

<210> SEQ ID NO 188
<211> LENGTH: 23
<212> TYPE: DNA
<213> ORGANISM: artificial sequence
<220> FEATURE:

<223> OTHER INFORMATION: synthesized

<400> SEQUENCE: 188
tctaagtctt ccagcacggg atc                                           23

<210> SEQ ID NO 189
<211> LENGTH: 18
<212> TYPE: DNA
<213> ORGANISM: artificial sequence
<220> FEATURE:
<223> OTHER INFORMATION: synthesized

<400> SEQUENCE: 189
tgacacagcc tgggactt                                                 18

<210> SEQ ID NO 190
<211> LENGTH: 19
<212> TYPE: DNA
<213> ORGANISM: artificial sequence
<220> FEATURE:
<223> OTHER INFORMATION: synthesized

<400> SEQUENCE: 190
cacacctcct gtggctaag                                                19

<210> SEQ ID NO 191
<211> LENGTH: 40
<212> TYPE: DNA
<213> ORGANISM: artificial sequence
<220> FEATURE:
<223> OTHER INFORMATION: synthesized

<400> SEQUENCE: 191
gagtgttctg aaggcaccac cagctccatt ggagggtct                          40

<210> SEQ ID NO 192
<211> LENGTH: 41
<212> TYPE: DNA
<213> ORGANISM: artificial sequence
<220> FEATURE:
<223> OTHER INFORMATION: synthesized

<400> SEQUENCE: 192
acacaagggc taatgggtgc cgccaaagca attgatcggt c                       41

<210> SEQ ID NO 193
<211> LENGTH: 22
<212> TYPE: DNA
<213> ORGANISM: artificial sequence
<220> FEATURE:
<223> OTHER INFORMATION: synthesized

<400> SEQUENCE: 193
ttggtgaacg gcttttccta tg                                            22

<210> SEQ ID NO 194
<211> LENGTH: 21
<212> TYPE: DNA
<213> ORGANISM: artificial sequence
<220> FEATURE:
<223> OTHER INFORMATION: synthesized

<400> SEQUENCE: 194
tgctctggat gggcgtcaac g                                             21

```
<210> SEQ ID NO 195
<211> LENGTH: 20
<212> TYPE: DNA
<213> ORGANISM: artificial sequence
<220> FEATURE:
<223> OTHER INFORMATION: synthesized

<400> SEQUENCE: 195
gagacaaagg aatgccctga                                                 20

<210> SEQ ID NO 196
<211> LENGTH: 20
<212> TYPE: DNA
<213> ORGANISM: artificial sequence
<220> FEATURE:
<223> OTHER INFORMATION: synthesized

<400> SEQUENCE: 196
gccctctcaa gtttccatgt                                                 20

<210> SEQ ID NO 197
<211> LENGTH: 41
<212> TYPE: DNA
<213> ORGANISM: artificial sequence
<220> FEATURE:
<223> OTHER INFORMATION: synthesized

<400> SEQUENCE: 197
cgggttgatg tgatgccaaa gcgagcacag agcttggaac a                         41

<210> SEQ ID NO 198
<211> LENGTH: 42
<212> TYPE: DNA
<213> ORGANISM: artificial sequence
<220> FEATURE:
<223> OTHER INFORMATION: synthesized

<400> SEQUENCE: 198
ggagcgatca taggtacggc tggcgactct caatccagta cg                        42

<210> SEQ ID NO 199
<211> LENGTH: 19
<212> TYPE: DNA
<213> ORGANISM: artificial sequence
<220> FEATURE:
<223> OTHER INFORMATION: synthesized

<400> SEQUENCE: 199
gaagtcttcg atttgcatg                                                  19

<210> SEQ ID NO 200
<211> LENGTH: 22
<212> TYPE: DNA
<213> ORGANISM: artificial sequence
<220> FEATURE:
<223> OTHER INFORMATION: synthesized

<400> SEQUENCE: 200
acatgtggca gtccatagtg ac                                              22

<210> SEQ ID NO 201
<211> LENGTH: 41
<212> TYPE: DNA
<213> ORGANISM: artificial sequence
<220> FEATURE:
<223> OTHER INFORMATION: synthesized
```

```
<400> SEQUENCE: 201
agggatctcg ctcctggaag atcaccgtca aggctgagaa c                    41

<210> SEQ ID NO 202
<211> LENGTH: 38
<212> TYPE: DNA
<213> ORGANISM: artificial sequence
<220> FEATURE:
<223> OTHER INFORMATION: synthesized

<400> SEQUENCE: 202
cgatgctggc gctgagtacg aatgagcccc agccttct                        38

<210> SEQ ID NO 203
<211> LENGTH: 19
<212> TYPE: DNA
<213> ORGANISM: artificial sequence
<220> FEATURE:
<223> OTHER INFORMATION: synthesized

<400> SEQUENCE: 203
tccacccatg gcaaattcc                                             19

<210> SEQ ID NO 204
<211> LENGTH: 19
<212> TYPE: DNA
<213> ORGANISM: artificial sequence
<220> FEATURE:
<223> OTHER INFORMATION: synthesized

<400> SEQUENCE: 204 aggggggcaga gatgatgac                                            19

<210> SEQ ID NO 205
<211> LENGTH: 21
<212> TYPE: DNA
<213> ORGANISM: artificial sequence
<220> FEATURE:
<223> OTHER INFORMATION: synthesized

<400> SEQUENCE: 205
tccattgatg acaagcttcc c                                          21

<210> SEQ ID NO 206
<211> LENGTH: 20
<212> TYPE: DNA
<213> ORGANISM: artificial sequence
<220> FEATURE:
<223> OTHER INFORMATION: synthesized

<400> SEQUENCE: 206
tcgtggagtc cactggcgtc                                            20

<210> SEQ ID NO 207
<211> LENGTH: 46
<212> TYPE: DNA
<213> ORGANISM: artificial sequence
<220> FEATURE:
<223> OTHER INFORMATION: synthesized

<400> SEQUENCE: 207
ccagatcttc caggaaaatc cacatctgta tttgatggaa gacctt                46

<210> SEQ ID NO 208
<211> LENGTH: 41
```

```
<212> TYPE: DNA
<213> ORGANISM: artificial sequence
<220> FEATURE:
<223> OTHER INFORMATION: synthesized

<400> SEQUENCE: 208
agaccagtaa ttgctggaag acttgtcttc caagaagctc c                      41

<210> SEQ ID NO 209
<211> LENGTH: 21
<212> TYPE: DNA
<213> ORGANISM: artificial sequence
<220> FEATURE:
<223> OTHER INFORMATION: synthesized

<400> SEQUENCE: 209
agatttttct ggaagacatg g                                            21

<210> SEQ ID NO 210
<211> LENGTH: 18
<212> TYPE: DNA
<213> ORGANISM: artificial sequence
<220> FEATURE:
<223> OTHER INFORMATION: synthesized

<400> SEQUENCE: 210
atgtcttccg gacaatcc                                                18

<210> SEQ ID NO 211
<211> LENGTH: 23
<212> TYPE: DNA
<213> ORGANISM: artificial sequence
<220> FEATURE:
<223> OTHER INFORMATION: synthesized

<400> SEQUENCE: 211
tgctggaaga cttgatttac tgg                                          23

<210> SEQ ID NO 212
<211> LENGTH: 24
<212> TYPE: DNA
<213> ORGANISM: artificial sequence
<220> FEATURE:
<223> OTHER INFORMATION: synthesized

<400> SEQUENCE: 212
ggaggcaccc tagggccagg gaaa                                         24

<210> SEQ ID NO 213
<211> LENGTH: 25
<212> TYPE: DNA
<213> ORGANISM: artificial sequence
<220> FEATURE:
<223> OTHER INFORMATION: synthesized

<400> SEQUENCE: 213
gttactgcaa gcagcaacaa agtcc                                        25

<210> SEQ ID NO 214
<211> LENGTH: 24
<212> TYPE: DNA
<213> ORGANISM: artificial sequence
<220> FEATURE:
<223> OTHER INFORMATION: synthesized

<400> SEQUENCE: 214
```

```
ggaggtattt tagggttagg gaaa                                                 24

<210> SEQ ID NO 215
<211> LENGTH: 25
<212> TYPE: DNA
<213> ORGANISM: artificial sequence
<220> FEATURE:
<223> OTHER INFORMATION: synthesized

<400> SEQUENCE: 215
attactacaa acaacaacaa aatcc                                                25

<210> SEQ ID NO 216
<211> LENGTH: 44
<212> TYPE: DNA
<213> ORGANISM: artificial sequence
<220> FEATURE:
<223> OTHER INFORMATION: synthesized

<400> SEQUENCE: 216
ggcgtcttca ccaccatgga gtgccacttc tcagatttga gaag                           44

<210> SEQ ID NO 217
<211> LENGTH: 44
<212> TYPE: DNA
<213> ORGANISM: artificial sequence
<220> FEATURE:
<223> OTHER INFORMATION: synthesized

<400> SEQUENCE: 217
ctccaagtct tccagtaaat gtgccacttc tcagatttga gaag                           44
```

USE OF HIGH-TEMPERATURE-RESISTANT CAS PROTEIN, AND METHOD AND REAGENT KIT FOR DETECTING TARGET NUCLEIC ACID MOLECULE

INCORPORATION OF SEQUENCE LISTING

This application contains a sequence listing in Computer Readable Form (CRF). The CFR file containing the sequence listing entitled "PB4084310-SequenceListing.txt", which was created on Dec. 3, 2020, and is 40,963 bytes in size. The information in the sequence listing is incorporated herein by reference in entirety.

TECHNICAL FIELD

The present invention is in the field of biotechnology. Specifically, the present invention relates to a use of high-temperature-resistant Cas protein, and a method and a reagent kit for detecting target nucleic acid molecule.

BACKGROUND

Rapid nucleic acid molecular detection is a very critical technology in public health, environmental monitoring, criminal investigation and other fields. Nucleic acid molecular detection can be used not only to detect whether humans, animals, plants, etc. are infected by pathogens, but also to detect genetic disease or cancer risks, to provide auxiliary reference for personal medications, and to detect microbial contamination in water bodies. At present, many nucleic acid detection methods have been developed, such as Real-time PCR, FISH hybridization technology (Fluorescence in situ hybridization) and so on. However, there is still a need to develop nucleic acid detection technologies that are fast, cheap and sensitive.

In recent years, CRISPR technology has shown great application value in the field of genome editing. This task is mainly accomplished by DNA (or RNA) targeted endonucleases such as Cas9. People can target Cas9 and other proteins to any nucleic acid target sequence containing PAM (e.g., the PAM sequence of Cas9 is NGG) by simply designing a guide RNA, and cause double-stranded DNA break (or RNA cleavage).

In addition to genome editing, CRISPR can also be used for gene regulation, epigenetic editing, functional gene screening, and genome imaging. Recently, CRISPR, a rich toolbox, has begun to appear in the field of nucleic acid detection and has attracted attention.

The first CRISPR-related nucleic acid detection technology was based on dCas9 (dead Cas9) protein. dCas9 is a mutation of Cas9 with the two catalytic cleavage active sites mutated. Therefore, the double-strand cleavage activity is lost, but dCas9 still retains the ability to be guided by the guide RNA and bind to specific DNA. Chen et al. used dCas9 to fuse with EGFP fluorescent protein, which can be guided by a specific guide RNA, and the fluorescence at the target sequence can be observed through a microscope. In 2017, Guk et al. reported a DNA-FISH system based on dCas9/sgRNA-SG I, which can selectively detect methicillin-resistant Staphylococcus aureus.

In 2013, the Collins team established a method to detect Zika virus on a paper piece. This method involves processes of RNA extraction, amplification and Toehold reaction detection. By design, if one virus strain happens to be different from another strain at the PAM site sequence (that is, one is NGG, the other is different), the PAM-containing strains can be targeted and cleavaged by Cas9, thereby affecting the amplification process and Toehold detection.

Recently, the principle of another Cas9-based nucleic acid detection method is the isothermal amplification method triggered by CRISPR/Cas9, which can also be used for site-specific nucleic acid detection. This technology involves the cleavage of CRISPR/Cas9, nickase and DNA polymerase. This method can not only detect a target concentration of 0.82 amol, but also distinguish the difference of single base in the nucleic acid molecules. The target discrimination of this method is more universal than the former method.

Principle of another nucleic acid detection is based on the "trans cleavage" (or "bypass cleavage") effect of some Cas proteins. In 2016, Zhang Feng et al. found that Cas13a (formerly known as C2c2) has bypass cleavage activity. That is, when Cas13a binds to the target RNA sequence, it will show the characteristics of chaotic cutting of other RNAs, which is used for specific nucleic acid detection, called SHERLOCK (Specific High Sensitivity Enzymatic Reporter UnLOCKing) technology.

Although there are many CRISPR-related nucleic acid detection methods, there is still a need to develop faster, simpler, and cheaper nucleic acid detection methods in this field.

SUMMARY OF THE INVENTION

The purpose of the present invention is to develop a faster, simpler and cheaper nucleic acid detection method related to CRISPR.

In a first aspect of the present invention, it provides a detection system for detecting target nucleic acid molecules, wherein the system comprises:
  (a) a Cas12b protein, wherein the Cas12b protein is Cas12b or a Cas protein having an activity similar to the bypass single-strand DNA cleavage activity of Cas12b;
  (b) a guiding RNA, wherein the guiding RNA directs the Cas12b protein to specifically bind to the target nucleic acid molecules; and
  (c) a nucleic acid probe, which is a single-stranded DNA; wherein, the target nucleic acid molecule is a target DNA.

In another preferred embodiment, the detection comprises a qualitative detection or a quantitative detection.

In another preferred embodiment, the detection system further comprises (d) a buffer.

In another preferred embodiment, the detection system further comprises target nucleic acid molecules to be detected.

In another preferred embodiment, the detection system further comprises:
  (e1) a polymerase, which is used for amplifying the target DNA;
  (e2) an optional reverse transcriptase, which is used for reverse transcription;
  (e3) dNTP, which is used for amplification reaction and/or reverse transcription reaction.

In another preferred embodiment, the detection system further comprises reaction agents used for LAMP reaction.

In another preferred embodiment, the concentration of the target nucleic acid molecules to be detected in the detection system is from $1\times10^{-9}$ nM to $1\times10^{3}$ nM; preferably from $1\times10^{-8}$ nM to $1\times10^{2}$ nM.

In another preferred embodiment, the concentration of the target nucleic acid molecules to be detected in the detection system is from 1 to 100 copies/µl or from 1 to $1 \times 10^{15}$ copies/µL, preferably from 1 to 10 copies/µL, more preferably from 1 to 5 copies/µL.

In another preferred embodiment, in the detection system, the molar ratio of the nucleic acid probe to the target nucleic acid molecule is from $10^3$:1 to $10^{14}$:1, preferably from $10^4$:1 to $10^7$:1.

In another preferred embodiment, the length of the guiding RNA is from 16 to 25 nt, preferably from 16 to 22 nt, more preferably from 16 to 20 nt.

In another preferred embodiment, the length of the guiding RNA is from 18 to 25 nt, preferably from 18 to 22 nt, more preferably from 18 to 20 nt.

In another preferred embodiment, when the target nucleic acid molecule is ssDNA, the detection site of the target nucleic acid molecule is located at position 9 or positions 10-16, preferably positions 10-14, more preferably positions 10-12 downstream of the PAM sequence of the guiding RNA.

In another preferred embodiment, when the detection site is located at position 9 downstream of the PAM sequence of the guiding RNA, the detection site is G.

In another preferred embodiment, the detection site is located at positions 9-20, preferably positions 10-18, more preferably positions 10-16 downstream of the PAM sequence of the guiding RNA.

In another preferred embodiment, the detection site of the target nucleic acid molecule is located at positions 1-12, more preferably position 1, 3 or 10 downstream of the PAM sequence of the guiding RNA.

In another preferred embodiment, the length of the guiding RNA is 15-30 nt, preferably 15-18 nt.

In another preferred embodiment, the target DNA comprises DNA formed based on RNA reverse transcription.

In another preferred embodiment, the target DNA comprises cDNA.

In another preferred embodiment, the target DNA is selected from the group consisting of: a single-stranded DNA, a double-stranded DNA, and a combination thereof.

In another preferred embodiment, the nucleic acid probe has a fluorescent group and a quenching group.

In another preferred embodiment, the fluorescent group and the quenching group are each independently located at the 5' end, the 3' end, and the middle of the nucleic acid probe.

In another preferred embodiment, the length of the nucleic acid probe is from 3 to 300 nt, preferably from 5 to 100 nt, more preferably from 6 to 50 nt, most preferably from 8 to 20 nt.

In another preferred embodiment, the target nucleic acid molecules comprise target nucleic acid molecules derived from a species selected from the group consisting of: a plant, an animal, an insect, a microorganism, a virus, and a combination thereof.

In another preferred embodiment, the target DNA is a synthetic or a naturally occurring DNA.

In another preferred embodiment, the target DNA comprises a wild-type or a mutant DNA.

In another preferred embodiment, the target DNA comprises DNA obtained by reverse transcription of RNA or amplification, such as cDNA and the like.

In another preferred embodiment, the Cas12b protein is selected from the group consisting of: AacCas12b (*Alicyclobacillus acidoterrestris*), Aac2Cas12b (*Alicyclobacillus acidiphilus*), AkaCas12b (*Alicyclobacillus kakegawensis*), AmaCas12b (*Alicyclobacillus macrosporangiidus*), AheCas12b (*Alicyclobacillus herbarius*), and AcoCas12b (*Alicyclobacillus contaminans*).

In another preferred embodiment, the nucleic acid probe comprises a single-stranded DNA with a detectable label.

In another preferred embodiment, the single-stranded DNA is a single-stranded DNA labeled with fluorescent and biotin.

In another preferred embodiment, the single-stranded DNA is a single-stranded DNA labeled with fluorescent.

In another preferred embodiment, the single-stranded DNA is a fluorescent probe labeled with a fluorescent group HEX at the 5' end and a quenching group BHQ1 at the 3' end.

In a second aspect of the present invention, it provides a detection system for detecting SNPs (single nucleotide polymorphisms) or nucleotide mutations (comprising single-base or multi-base mutations), wherein the system comprises a first detection system and a second detection system;

wherein, the first detection system comprises:
(a1) a Cas12b protein, wherein the Cas12b protein is Cas12b or a Cas protein having an activity similar to the bypass single-strand DNA cleavage activity of Cas12b;
(b1) a first guiding RNA, wherein the first guiding RNA directs the Cas12b protein to specifically bind to target nucleic acid molecules; and
(c1) a nucleic acid probe, which is a single-stranded DNA;

and the second detection system comprises:
(a2) a Cas12b protein, wherein the Cas12b protein is Cas12b or a Cas protein having an activity similar to the bypass single-strand DNA cleavage activity of Cas12b;
(b2) a second guiding RNA, wherein the second guiding RNA directs the Cas12b protein to specifically bind to target nucleic acid molecules; and
(c2) a nucleic acid probe, which is a single-stranded DNA;

wherein, the target nucleic acid molecule is a target DNA;
in addition, the first guiding RNA and the second guiding RNA target a same nucleic acid sequence region containing the SNP site, and the first guiding RNA targets the wild-type (or unmutated) nucleic acid sequence of the SNP site, and the second guiding RNA targets the mutant nucleic acid sequence of the SNP site.

In another preferred embodiment, the detection system also comprises a blank control system.

In another preferred embodiment, the blank control system comprises:
(a3) a Cas12b protein, wherein the Cas12b protein is Cas12b or a Cas protein having an activity similar to the bypass single-strand DNA cleavage activity of Cas12b;
(c3) a nucleic acid probe, which is a single-stranded DNA.

In another preferred embodiment, the SNP site is located at position 9 or positions 10-16, preferably positions 10-14, more preferably positions 10-12 downstream of the PAM sequence of the guiding RNA.

In another preferred embodiment, the SNP site is located at position 9 downstream of the PAM sequence of the guiding RNA, and the detection site is G.

In another preferred embodiment, the SNP site is located at positions 9-20, preferably positions 10-18, more preferably positions 10-16 downstream of the PAM sequence of the guiding RNA.

In another preferred embodiment, the length of the first or second guiding RNA is from 16 to 25 nt, preferably from 16 to 22 nt, more preferably from 16 to 20 nt.

In another preferred embodiment, the length of the first or second guiding RNA is from 18 to 25 nt, preferably from 18 to 22 nt, more preferably from 18 to 20 nt.

In a third aspect of the invention, it provides a kit for detecting target nucleic acid molecules, comprising:
i) a first container and a Cas12b protein located in the first container, wherein the Cas12b protein is Cas12b or a Cas protein having an activity similar to the bypass single-strand DNA cleavage activity of Cas12b;
ii) an optional second container and a guiding RNA located in the second container, wherein the guiding RNA directs the Cas protein to specifically bind to the target nucleic acid molecules;
iii) a third container and a nucleic acid probe located in the third container;
iv) optionally a fourth container and a buffer located in the fourth container;
wherein, the target nucleic acid molecule is a target DNA.

In another preferred embodiment, any two, three, or four (or all) of the first, second, third, and fourth containers may be the same container or different containers.

In another preferred embodiment, the nucleic acid probe has a fluorescent group and a quenching group.

In another preferred embodiment, the kit further comprises a buffer.

In another preferred embodiment, the kit further comprises:
v) a fifth container and a polymerase for amplifying target DNA located in the fifth container;
vi) an optional sixth container and a reverse transcriptase for reverse transcription located in the sixth container;
vii) a seventh container and dNTP for amplification reaction and/or reverse transcription reaction located in the seventh container.

In another preferred embodiment, the detection system further comprises reaction agents used for LAMP reaction.

In another preferred embodiment, the fifth container, the sixth container and the seventh container may be the same container or different containers.

In another preferred embodiment, two, more than two, or all of the first container to the seventh container may be the same container or different containers.

In a fourth aspect of the invention, it provides a method for detecting whether target nucleic acid molecules are present in a sample, which comprises the steps of:
(i) providing a detection system for detecting target nucleic acid molecules according to the first aspect of the invention, and the detection system further comprises a sample to be detected; and
(ii) detecting whether the nucleic acid probe in the detection system is cleaved by the Cas12b protein, wherein the cleavage is a transcleavage of the bypass single-stranded DNA;
wherein, if the nucleic acid probe is cleaved by the Cas12b protein, it indicates that the target nucleic acid molecule is present in the sample; and if the nucleic acid probe is not cleaved by the Cas12b protein, it indicates that the target nucleic acid molecule is not present in the sample.

In another preferred embodiment, the Cas12b protein is Cas12b or a Cas protein having an activity similar to the bypass single-strand DNA cleavage activity of Cas12b.

In another preferred embodiment, the sample to be detected comprises an unamplified sample and an amplified (or nucleic acid amplified) sample.

In another preferred embodiment, the sample to be detected is a sample obtained by amplification.

In another preferred embodiment, the nucleic acid amplification method is selected from the group consisting of: PCR amplification, LAMP amplification, RPA amplification, ligase chain reaction, branched DNA amplification, NASBA, SDA, transcription-mediated amplification, rolling circle amplification, HDA, SPIA, NEAR, TMA and SMAP2.

In another preferred embodiment, the PCR comprises high temperature PCR, normal temperature PCR, or low temperature PCR.

In another preferred embodiment, the method is used for detecting whether there is an SNP, a point mutation, a deletion, and/or an insertion in nucleic acids at a target site.

In another preferred embodiment, when the PAM sequence is absent at the upstream or downstream of the target site (in the range of from −20 nt to +20 nt, preferably in the range of from −16 nt to +16 nt), nucleic acid amplification was carried out using primers introduced with PAM.

In another preferred embodiment, the primer introduced with PAM has a structure of formula I from 5' to 3':

$$P1\text{-}P2\text{-}P3 \qquad (I)$$

wherein,
P1 is a 5' segment sequence at the 5' end, which is complementary or non-complementary to the sequence of the target nucleic acid molecule;
P2 is a PAM sequence;
P3 is a 3' segment sequence at the 3' end, which is complementary to the sequence of the target nucleic acid molecule.

In another preferred embodiment, the PAM primer specifically binds upstream or downstream of the target nucleic acid molecule.

In another preferred embodiment, P1 has a length of 0-20 nt.

In another preferred embodiment, P3 has a length of 5 to 20 nt.

In another preferred embodiment, the PAM primer has a length of 16 to 50 nt, preferably 20 to 35 nt.

In another preferred embodiment, the complementation comprises full complementation and partial complementation.

In another preferred embodiment, at least one primer with a PAM sequence is used in the nucleic acid amplification.

In another preferred embodiment, when the PAM sequence is present at the upstream or downstream of the target site (in the range of from −20 nt to +20 nt, preferably in the range of from −15 nt to +15 nt, more preferably in the range of from −10 nt to +10 nt), primers with or without a PAM sequence can be used, and the amplified amplification product contains the PAM sequence.

In another preferred embodiment, the detection in step (ii) comprises a fluorescence detection method.

In another preferred embodiment, a microplate reader or a fluorescence spectrophotometer is used in the fluorescence detection method.

In a fifth aspect of the invention, it provides a method for detecting whether target nucleic acid molecules are present in a sample, which comprises the steps of:

(i) providing a detection system, comprising:
- (a) a Cas12b protein, wherein the Cas12b protein is Cas12b or a Cas protein having an activity similar to the bypass single-strand DNA cleavage activity of Cas12b;
- (b) a guiding RNA, wherein the guiding RNA directs the Cas12b protein to specifically bind to the target nucleic acid molecules;
- (c) a nucleic acid probe, which is a single-stranded DNA;
   wherein, the target nucleic acid molecule is a target DNA;
- (d) buffer;
- (e1) a polymerase, which is used for amplifying target DNA;
- (e2) an optional reverse transcriptase, which is used for reverse transcription;
- (e3) dNTP, which is used for amplification reaction and/or reverse transcription reaction; and
- (f) a sample to be tested;

(ii) performing a reverse transcription and/or amplification reaction in the detection system, thereby obtaining a detection system reverse transcripted and/or amplified;

(iii) detecting whether the nucleic acid probe in the detection system obtained in the previous step is cleaved by the Cas12b protein, wherein the cleavage is a trans-cleavage of the bypass single-stranded DNA;

wherein, if the nucleic acid probe is cleaved by the Cas12b protein, it indicates that the target nucleic acid molecule is present in the sample; and if the nucleic acid probe is not cleaved by the Cas12b protein, it indicates that the target nucleic acid molecule is not present in the sample.

In another preferred embodiment, in the step (ii), the temperature of the detection system is maintained at 50-70° C., preferably 50-65° C., more preferably 55-65° C.

In another preferred embodiment, in the step (iii), the temperature of the detection system is maintained at 25-70° C., preferably 48-65° C.

In another preferred embodiment, the nucleic acid amplification method is selected from the group consisting of: PCR amplification, LAMP amplification, RPA amplification, ligase chain reaction, branched DNA amplification, NASBA, SDA, transcription-mediated amplification, rolling circle amplification, HDA, SPIA, NEAR, TMA and SMAP2.

In another preferred embodiment, the nucleic acid amplification comprises LAMP amplification.

In another preferred embodiment, in the detection system, the concentration of the nucleic acid in the sample to be tested is from $1 \times 10^{-11}$ nM to $1 \times 10^{-5}$ nM; preferably from $1 \times 10^{-9}$ nM to $1 \times 10^{-6}$ nM, more preferably from $1 \times 10^{-8}$ nM to $1 \times 10^{-7}$ nM.

In another preferred embodiment, the detection comprises a qualitative detection or a quantitative detection.

In another preferred embodiment, the quantitative detection is absolute quantitative detection (such as quantitative detection combined with digital PCR technology).

In another preferred embodiment, the total time of the steps (ii) and (iii) is ≤2 hours, preferably ≤1.5 hours, more preferably ≤1 hour (such as 30-60 minutes).

In another preferred embodiment, the target nucleic acid molecule is a methylated nucleic acid sequence, or the methylated nucleic acid sequence is a nucleic acid sequence obtained after an conversion of unmethylated C to uracil.

In another preferred embodiment, the methylated nucleic acid sequence is treated with bisulfite to convert unmethylated C to uracil.

In another preferred embodiment, the target nucleic acid molecule is a DNA molecule form by a reverse transcription reaction of a linear or circular RNA molecule, or a DNA molecule formed by RT-PCR.

In another preferred embodiment, the RT-PCR comprises RT-LAMP.

In a sixth aspect of the invention, it provides a use of a Cas12b protein for the preparation of a detection reagent or kit for detecting target nucleic acid molecules based on a bypass single-stranded DNA cleavage, wherein the Cas12b protein is Cas12b or a Cas protein having an activity similar to the bypass single-strand DNA cleavage activity of Cas12b.

In another preferred embodiment, the Cas12b protein is selected from the group consisting of: AacCas12b (*Alicyclobacillus acidoterrestris*), Aac2Cas12b (*Alicyclobacillus acidiphilus*), AkaCas12b (*Alicyclobacillus kakegawensis*), AmaCas12b (*Alicyclobacillus macrosporangiidus*), AheCas12b (*Alicyclobacillus herbarius*), and AcoCas12b (*Alicyclobacillus contaminans*).

In a seventh aspect of the invention, it provides a device for detecting whether target nucleic acid molecules are present in a sample, wherein the device comprises:
- (a) an amplification reaction—bypass cleavage reaction module, which is used for performing nucleic acid amplification reactions and bypass cleavage reactions on the digital reaction system, wherein the bypass cleavage reaction is mediated by Cas12b protein; and
- (b) a signal detection module, which is used for detecting whether Cas12b protein-mediated bypass cleavage occurs in each digital reaction system.

In another preferred embodiment, the nucleic acid amplification reaction and the bypass cleavage reaction are performed simultaneously.

In another preferred embodiment, the amplification reaction—bypass cleavage reaction module further comprises a temperature control unit, for setting the temperature of the digital reaction system in the device at a predetermined temperature.

In another preferred embodiment, the predetermined temperature is 50-70° C., preferably 50-65° C., more preferably 55-65° C.

In another preferred embodiment, the predetermined temperature is 25-70° C., preferably 48-65° C.

In another preferred embodiment, the predetermined temperature is substantially the same during the entire amplification reaction and bypass cleavage reaction.

In another preferred example, the fluctuation range of the predetermined temperature is within ±5° C., preferably within ±3° C., more preferably within ±1° C.

In another preferred embodiment, the nucleic acid amplification is an isothermal amplification, or an amplification wherein the temperature difference in denaturation-renaturation-extension is ≤10° C. (preferably ≤5° C., more preferably ≤3° C.).

In another preferred embodiment, the nucleic acid amplification comprises: LAMP amplification.

In another preferred embodiment, the digital reaction system comprises a droplet digital PCR (ddPCR) reaction system or a chip digital PCR (cdPCR) reaction system.

In another preferred embodiment, the digital reaction system comprises a plurality of independent reaction system units, and each reaction system unit comprises:

(a) a Cas12b protein, wherein the Cas12b protein is Cas12b or a Cas protein having an activity similar to the bypass single-strand DNA cleavage activity of Cas12b;
(b) a guiding RNA, wherein the guiding RNA directs the Cas12b protein to specifically bind to target nucleic acid molecules;
(c) a nucleic acid probe, which is a single-stranded DNA; wherein, the target nucleic acid molecule is a target DNA;
(d) buffer;
(e1) a polymerase, which is used for amplifying target DNA;
(e2) an optional reverse transcriptase, which is used for reverse transcription;
(e3) dNTP, which is used for amplification reaction and/or reverse transcription reaction; and
(f) a sample to be tested;
wherein, due to dilution processing (i.e., digital processing), each independent reaction system contains either 1 copy of nucleic acid from the sample to be tested or 0 copies of nucleic acid from the sample to be tested.

In another preferred embodiment, each reaction system unit is the same, except for the 1 or 0 copies of nucleic acid from the sample to be tested.

In another preferred embodiment, the reaction system unit is a droplet.

In another preferred embodiment, the reaction system unit is a micro reaction system located in the micropores of the chip.

In another preferred embodiment, the device further comprises a sample loading module and/or a control module.

In another preferred embodiment, the signal detection module comprises an imaging module.

In another preferred embodiment, the imaging module comprises a fluorescence detection unit.

In another preferred embodiment, the fluorescence detection unit irradiates the digital reaction system to excite the reaction system to generate a fluorescent signal, and converts the fluorescent signal into a digital signal, which is preferably sent to the control module.

In another preferred embodiment, the control module performs arithmetic analysis based on the quantity of the fluorescent signal (preferably, the digital signal converted from the fluorescent signal) and the total number of the reaction system units, thereby obtaining the quantitative detection result of the target nucleic acid (such as concentration or copy number).

In another preferred embodiment, the device is a digital PCR detection device.

It should be understood that within the scope of the present invention, the various technical features of the present invention above and the various technical features specifically described hereinafter (as in the embodiments) may be combined with each other to constitute a new or preferred technical solution. Due to space limitations, it is not repeated here.

DETAILED DESCRIPTION

Figure 1:
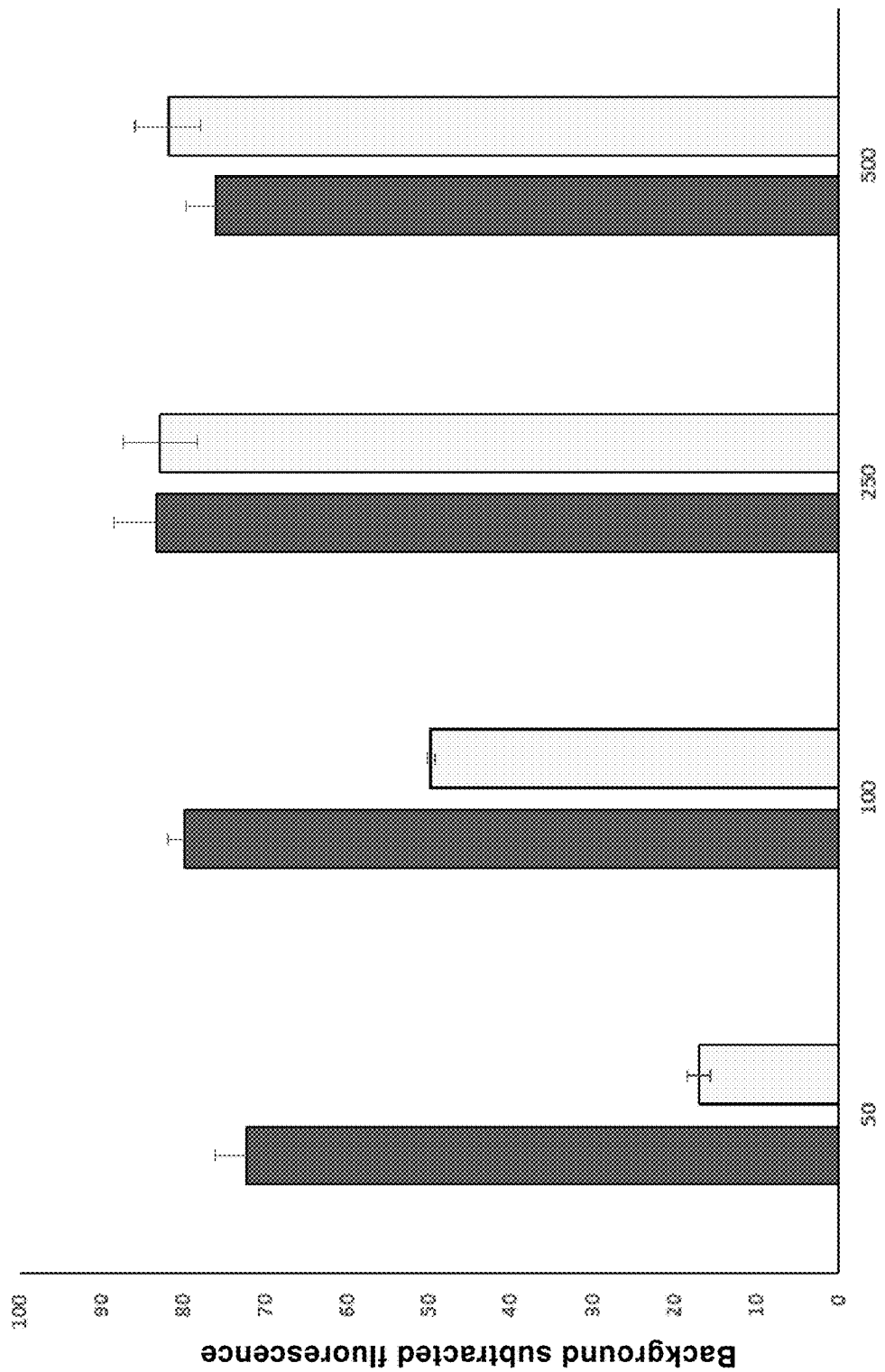
FIG. 1 shows the fluorescence intensity generated by trans cleavage of probes with different concentrations of Cas12b and sgRNA, when dsDNA and ssDNA were used as the target DNA, respectively.

By extensively and intensively studies, the present inventors have for the first time developed a technical solution for target nucleic acid detection, by studying the cleavage properties of Cas12b enzymes. The experimental results show that the technical solution of the present invention can quickly, highly sensitively and accurately detect trace nucleic acid, and can be applied to different fields such as rapid gender identification using saliva samples, *E. coli* contamination detection, rapid identification of SNP genotypes, RNA virus detection, and trace DNA concentration determination in a sample. On this basis, the present invention has been completed.

The Terms

The term "guiding RNA", or "gRNA", or "sgRNA" refers to an RNA that directs the Cas protein (such as Cas12b protein) to specifically bind to a target DNA sequence.

The term "CRISPR" refers to clustered regular interspaced short palindromic repeats, which are the immune systems of many prokaryotes.

The term "Cas protein" refers to a CRISPR-associated protein which is a related protein in the CRISPR system.

The term "Cas12a" (formerly "Cpf1") refers to a crRNA-dependent endonuclease, which is an enzyme of type V-A in the CRISPR system classification.

The terms "Cas12b", "C2c1" are used interchangeably and refer to a sgRNA-dependent endonuclease, which is an enzyme of type V-B in the CRISPR system classification.

The term "LAMP" is a loop-mediated isothermal amplification technique and is a thermostatic nucleic acid amplification technique suitable for gene diagnosis.

The term "PAM" refers to the protospacer-adjacent motif, which is required for Cas12b cleavage of double-stranded DNA, and the PAM of AacCas12b is the sequence TTN.

The term "PCR" refers to "polymerase chain reaction", a method used for amplifying large amounts of DNA fragments of interest.

HOLMES v2.0 refers to one-HOur Low-cost Multipurpose highly Efficient System version 2.0, which is a nucleic acid detection method based on Cas12b.

Detection Method

The present invention provides a method for detecting target nucleic acid molecules, which comprises adding a guiding RNA, a Cas protein, a nucleic acid probe and a buffer into the reaction system containing the target nucleic acid molecules, and then detecting the fluorescence intensity.

The present invention provides a method for rapidly detecting target nucleic acid molecules with high specificity. Once the target DNA (single or double stranded), the sgRNA, and the Cas12b protein form a ternary complex, the complex cleaves other single-stranded DNA molecules in the system.

In the method, the target DNA (a DNA sequence to be detected) is targeted by the designed sgRNA; and sgRNA and Cas12b protein are added to the detection system. When the target DNA (single-stranded DNA or double-stranded DNA) is present, Cas12b, the sgRNA and the target DNA form a ternary complex, and the complex cleaves the nucleic acid probe labeled with fluorescent signal using its bypassing cleavage activity, thereby emitting fluorescence.

A representative nucleic acid probe is a single-stranded DNA with a fluorescent group and a quenching group attached to both ends, so once the probe is cleaved, the fluorescent group can emit light.

In the present invention, by detecting the fluorescence, it is possible to know whether the target DNA molecule is contained in the system to be detected.

In the present invention, an appropriate Cas protein is Cas12b, and preferably the Cas12b protein is: AacCas12b (*Alicyclobacillus acidoterrestris*), Aac2Cas12b (*Alicyclobacillus acidiphilus*), AkaCas12b (*Alicyclobacillus kakegawensis*), AmaCas12b (*Alicyclobacillus macrosporangiidus*), AheCas12b (*Alicyclobacillus herbarius*), or AcoCas12b (*Alicyclobacillus contaminans*).

The target nucleic acid molecules to be detected in the reaction system containing the target nucleic acid molecules to be detected can be unamplified, or obtained after amplification, and/or after reverse transcription amplification.

The detection method of the present invention can detect nucleic acid molecules of different species, such as nucleic acid molecules of mammals, plants, or microorganisms, and viruses. The method of the present invention is particularly suitable for detecting pathogenic microorganisms, gene mutations or specific target DNA or RNA.

The method of the present invention allows rapid detection of whether a sample contains a specific DNA sequence. Further, by combining with amplification technology (such as LAMP, PCR, asymmetric PCR, RPA etc.), the sensitivity of the detection method can be greatly improved.

Preferably, the bypass cleavage of Cas12b can be combined with nucleic acid amplification (such as isothermal amplification, LAMP amplification) and other technologies (such as digital PCR).

In a preferred embodiment of the present invention, when the detection based bypass cleavage of Cas12b is combined with nucleic acid amplification, the detection sensitivity can be increased to a concentration of $10^{-8}$ nM or lower.

In addition, when the detection based bypass cleavage of Cas12b is combined with digital PCR, the detection sensitivity can be increased to 1 copy per reaction system (such as a microdroplet), which can almost meet all the needs of detection sensitivity.

Cas12b-Based Nucleic Acid Detection Method and HOLMES v2.0 (One-HOur Low-Cost Multipurpose Highly Efficient System Version 2.0)

Establishment of Nucleic Acid Detection Methods

Using the characteristics of Cas12b, the present invention has developed a method for specifically detecting nucleic acid molecules, which is called HOLMES (one-HOur Low-cost Multipurpose highly Efficient System version 2.0). As the name of the technology, it is characterized as a fast (1 hour), low cost, multi-purpose, efficient, and simple test method.

In the whole reaction system, it can be divided into two large steps. One is the amplification of the template nucleic acid, and the other is the specific nucleic acid detection by the Cas12b protein. Alternatively, the two steps can be combined into one step.

In the present invention, in a preferred embodiment, LAMP or asymmetric PCR is used for amplification of nucleic acids. But in practice, any amplification method can be combined with nucleic acid detection of the second step, such as isothermal amplification method RPA or the like.

The initial nucleic acid is not limited to double-stranded DNA, and may be single-stranded DNA or RNA, and thus the method is applicable to various types of nucleic acid molecules.

For the nucleic acid detection step, the three components are the significant to the experiment, namely Cas12b, sgRNA and the nucleic acid probe. In addition to the AacCas12b mentioned in the examples, other Cas12b proteins are equally suitable for this method. In addition, other types of Cas proteins (such as Cas12c protein) are also within the protection scope of the present invention.

For sgRNA as a guide, after artificial modification and other modifications, it will be more stable in the system. In the selection of nucleic acid probes, HEX and BHQ1 labeled short single stranded DNA (which is also labeled with FAM and Eclipse) is selected in the present invention, and any other detectable labeling method is theoretically applicable as long as the nucleic acid probe can produce a detectable difference after being cleaved.

Alternatively, the nucleic acid probe can also be designed to be fluorescent after binding to the compound to detect whether the probe is cleaved.

In order to facilitate understanding, various characteristics of the Cas12b-based nucleic acid detection method (including the preferred "HOLMES" v2.0 method) of the present invention are further described.

Identification of Cas12b trans cleavage activity: Although Cas12a and Cas12b are quite different in sequence, the inventors' experimental results show that Cas12b also has trans cleavage activity.

Firstly, the bypass DNA was designed as a fluorescent probe consisting of a random sequence with a length of 12 nt, and the fluorescent group HEX was labeled at the 5'-terminal end and the quenching group BHQ1 was labeled at the 3'-terminal end (HEX-N12-BHQ1). When the system contains the target DNA fragment (dsDNA or ssDNA), a ternary complex of the target DNA, sgRNA and Cas12b protein will be formed.

At this time, the probe is cleaved, and the fluorescence emitted from the HEX fluorescent group can be detected by the fluorescence detector (excitation light 535 nm, emission light 556 nm).

As shown in FIG. 1, when the concentration of Cas12b and sgRNA was 250 nM or 500 nM, both dsDNA and ssDNA as targets had relatively high fluorescence intensity. When the concentration of Cas12b and sgRNA was reduced to 50 nM and 100 nM, ssDNA as the target sequence still had a high fluorescence intensity.

PAM characteristics of Cas12b trans cleavage: Studies have shown that a sequence called PAM is required during the Cas12b cis cleavage of a double-stranded DNA. That is, only the 5' end followed by 5'-TTN-3' can be cut by Cas12b. In order to test whether the target sequence of Cas12b requires the PAM during trans cleavage, the inventors designed different sequences (including TTC, TAC, ATC, AAC, GGC and CCC) at the position of PAM, to test whether the PAM is required during trans cleavage.

Figure 2:
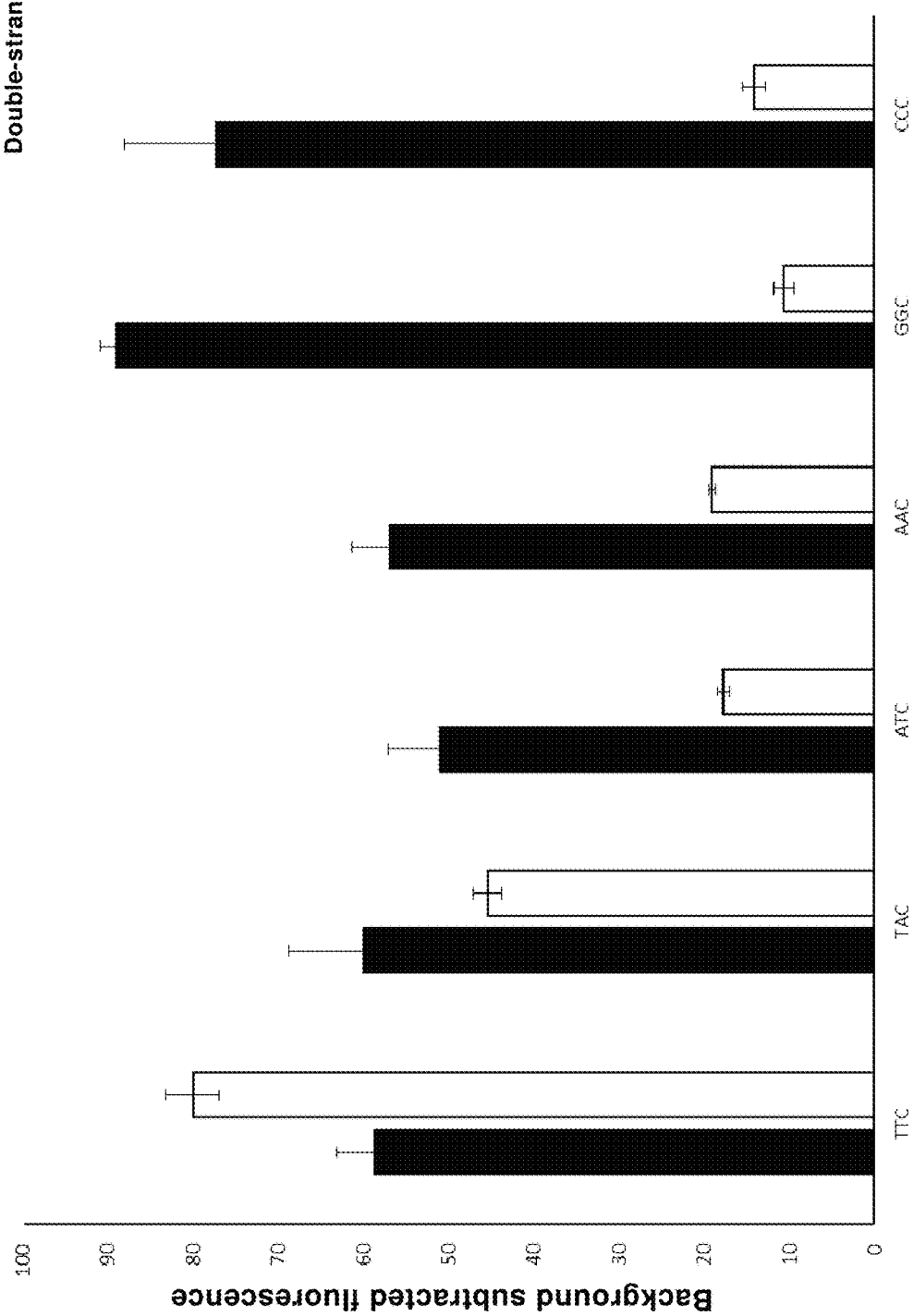
FIG. 2 shows the effect of different bases in the PAM sequence on the intensity of the fluorescence detection of the trans cleavage, when dsDNA and ssDNA were used as the target DNA, respectively.

As shown in FIG. 2, when double-stranded DNA was used as the target, the trans cleavage by Cas12b was more sensitive to the PAM sequence. That is, a higher trans cleavage fluorescence intensity can be obtained when TTC is used (the fluorescence intensity generated after it changed into TAC is slightly lower than that of TTC). And when single-stranded DNA was used as a target, it was not sensitive to the PAM sequence and always showed a high trans cleavage fluorescence intensity.

Cas12b trans cleavage rate: When ssDNA and dsDNA are used as target DNA respectively, the rate of Cas12b trans cleavage was measured.

Figure 3:
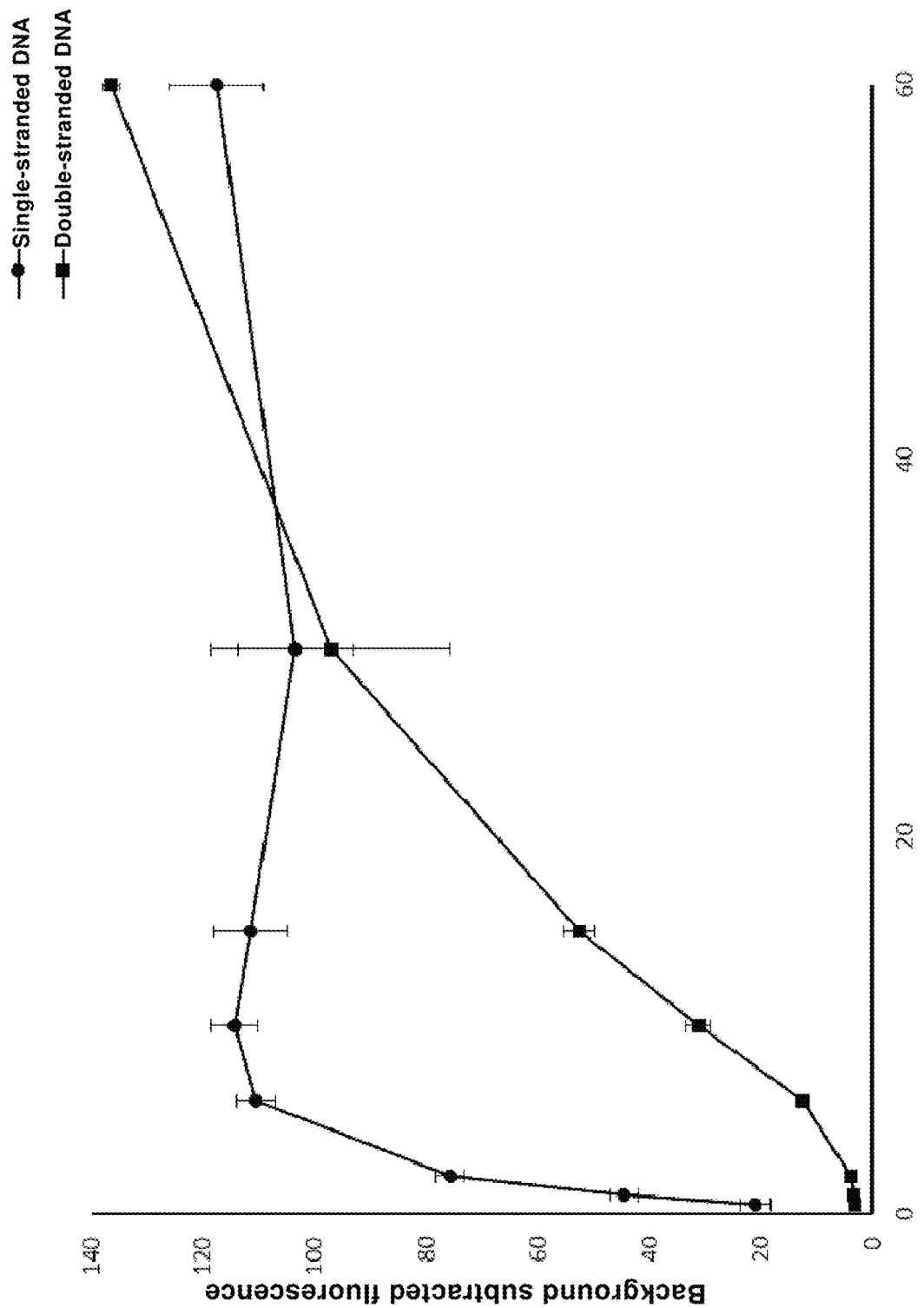
FIG. 3 shows the trans cleavage rate by Cas12b, when ssDNA or dsDNA was used as a target.

As shown in FIG. 3, it can be seen that when ssDNA was used as a substrate, the trans cleavage rate of Cas12b was very fast, and it was close to the highest value in only 6 minutes. When dsDNA was used as a substrate, the cleavage speed was relatively slow, and there was a gradual increase process. This indicates that ssDNA should be used as the substrate for Cas12 bypass cleavage for some occasions that require rapid detection (such as ≤10 minutes).

Figure 4:
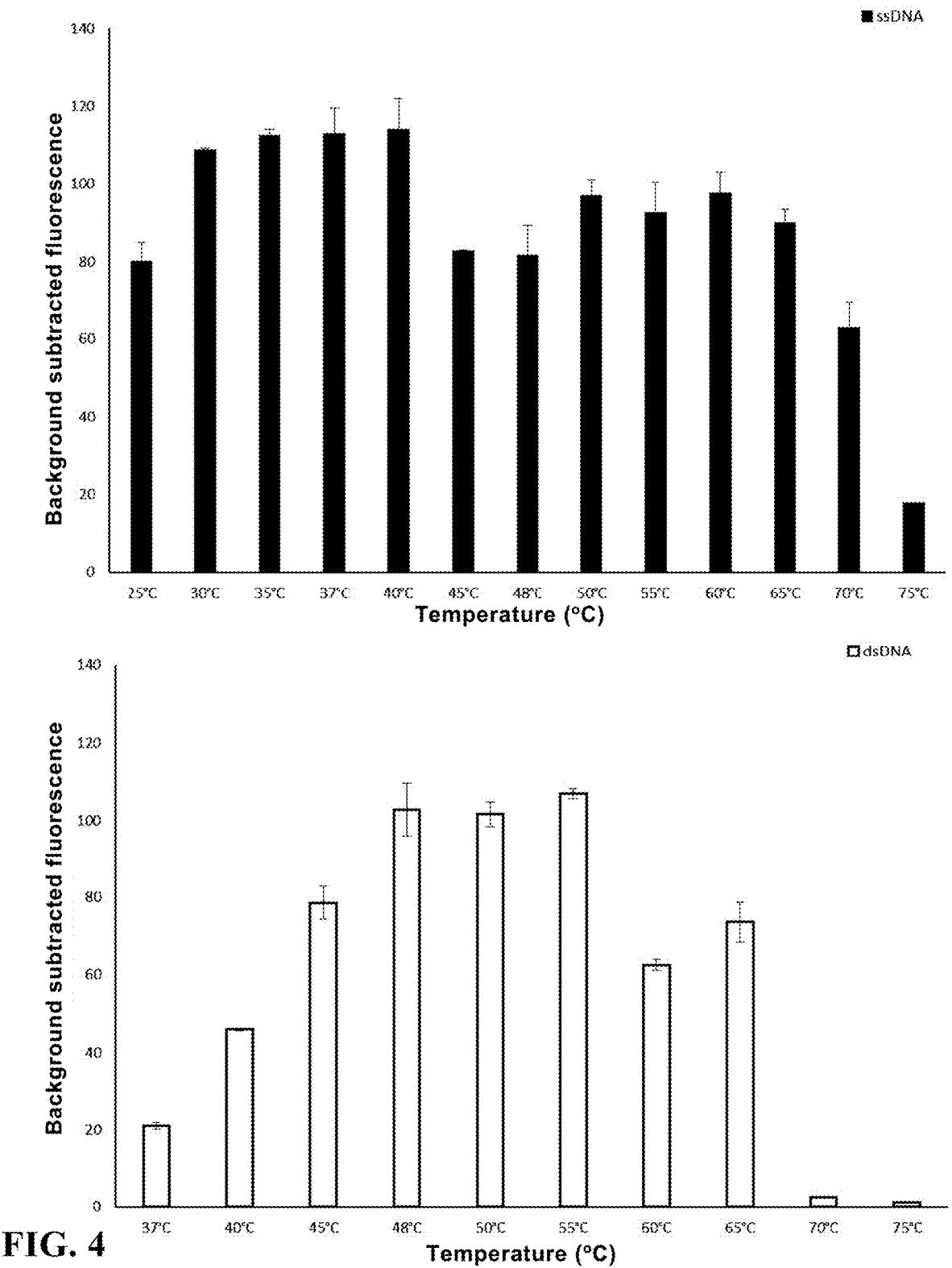
FIG. 4 shows the fluorescence intensity of trans cleavage by Cas12b with dsDNA or ssDNA as the target under different temperature conditions.

The applicable temperature range of Cas12b trans cleavage: Cas12b has a very wide temperature range for trans cleavage, whether it is ssDNA or dsDNA as the target sequence. The temperature of 45-65° C. has a good response value, especially that the temperature range for ssDNA target is wider, of 25-70° C. (see FIG. 4).

Cas12b detection sensitivity: The inventors tested the detection sensitivity of Cas12b by diluting the concentration of the target dsDNA or ssDNA. In a preferred embodiment, the target ssDNA (DNMT1-3(TTC PAM)-R) or dsDNA (obtained by annealing of the two oligonucleotides DNMT1-3(TTC PAM)-F and DNMT1-3(TTC PAM)-R) was diluted to concentrations of 100 nM, 10 nM, 1 nM, . . . to $10^{-4}$ nM.

Figure 5:
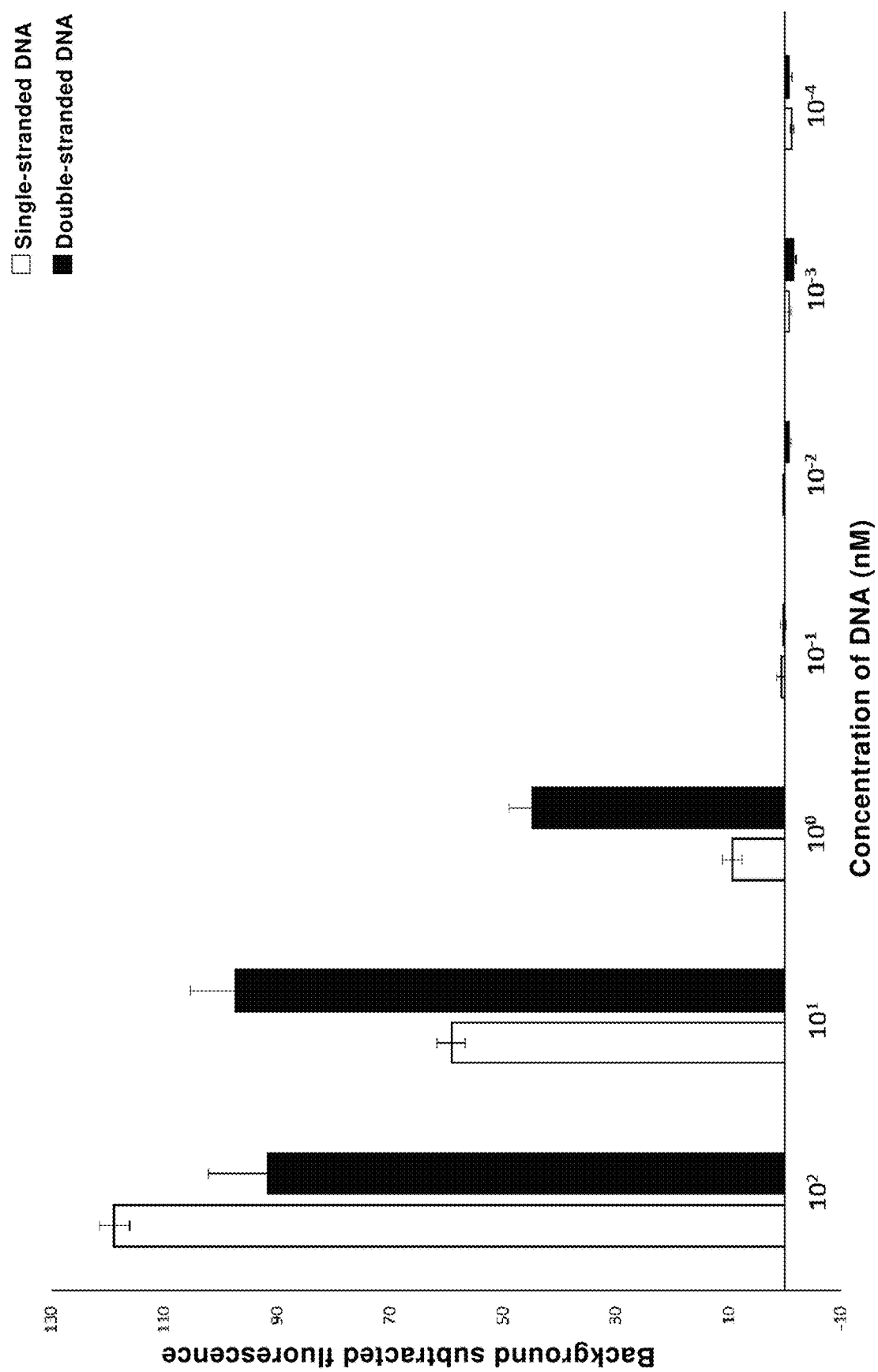
FIG. 5 shows the detection sensitivity of Cas12b (i.e., the fluorescence intensity of trans cleavage) with dsDNA or ssDNA as the target through gradient dilution of the target sequence.

The results show that when the DNA concentration was 1 nM, the target molecule could still be detected using Cas12b (FIG. 5).

Figure 6:
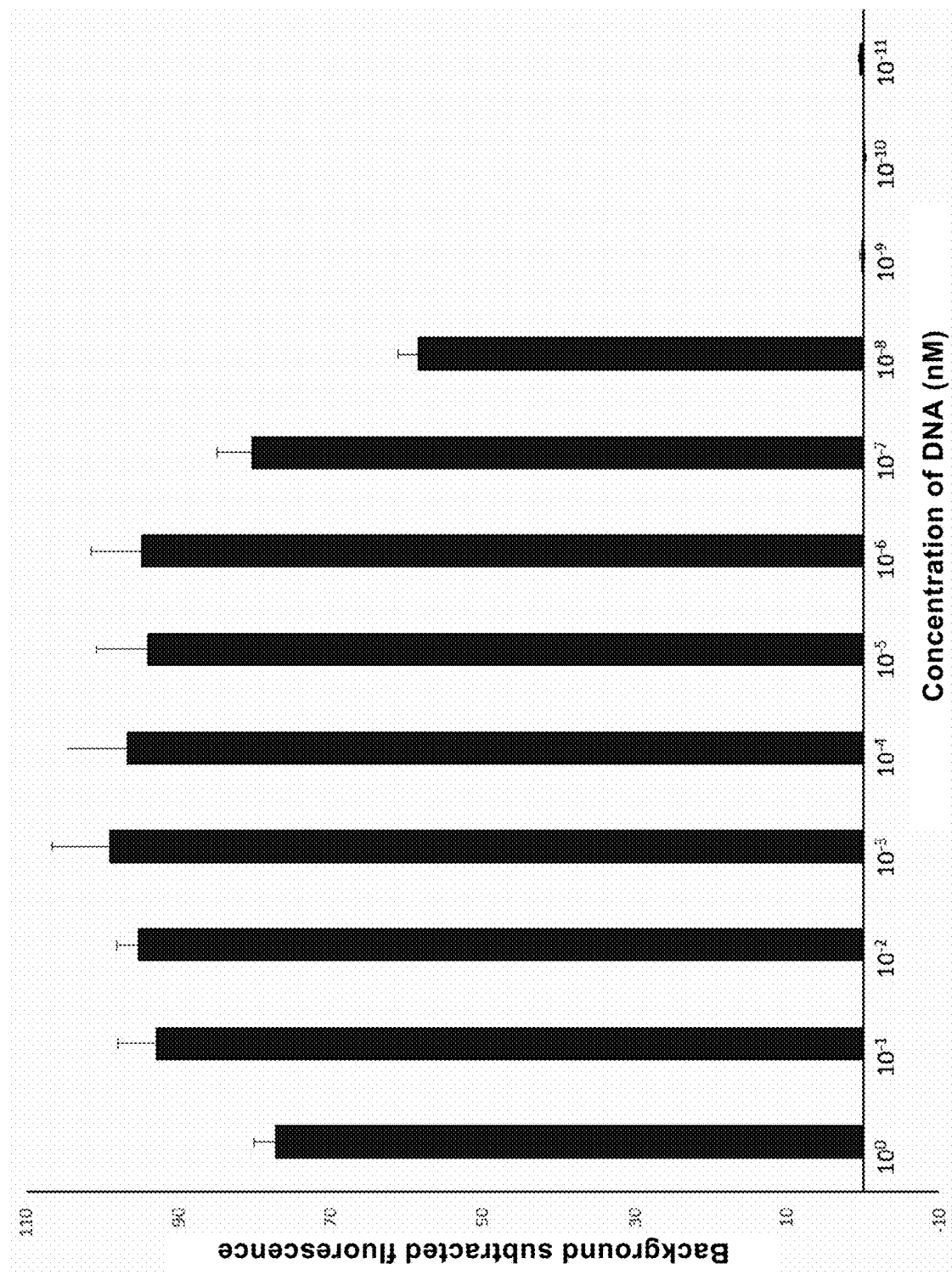
FIG. 6 shows the detection sensitivity of Cas12b combined with LAMP amplification reaction (i.e., HOLMES v2.0 method) to target.

HOLMES v2.0 sensitivity test: In one example, when Cas12b and LAMP reaction were combined (i.e. HOLMES v2.0), the detection sensitivity could reach $10^{-8}$ nM, which greatly improved the sensitivity of target nucleic acid sequence detection (FIG. 6).

SNP test against ssDNA target: The method of the present invention is very suitable for detecting nucleic acid mutations, including SNPs, especially SNPs in ssDNA targets.

Figure 7:
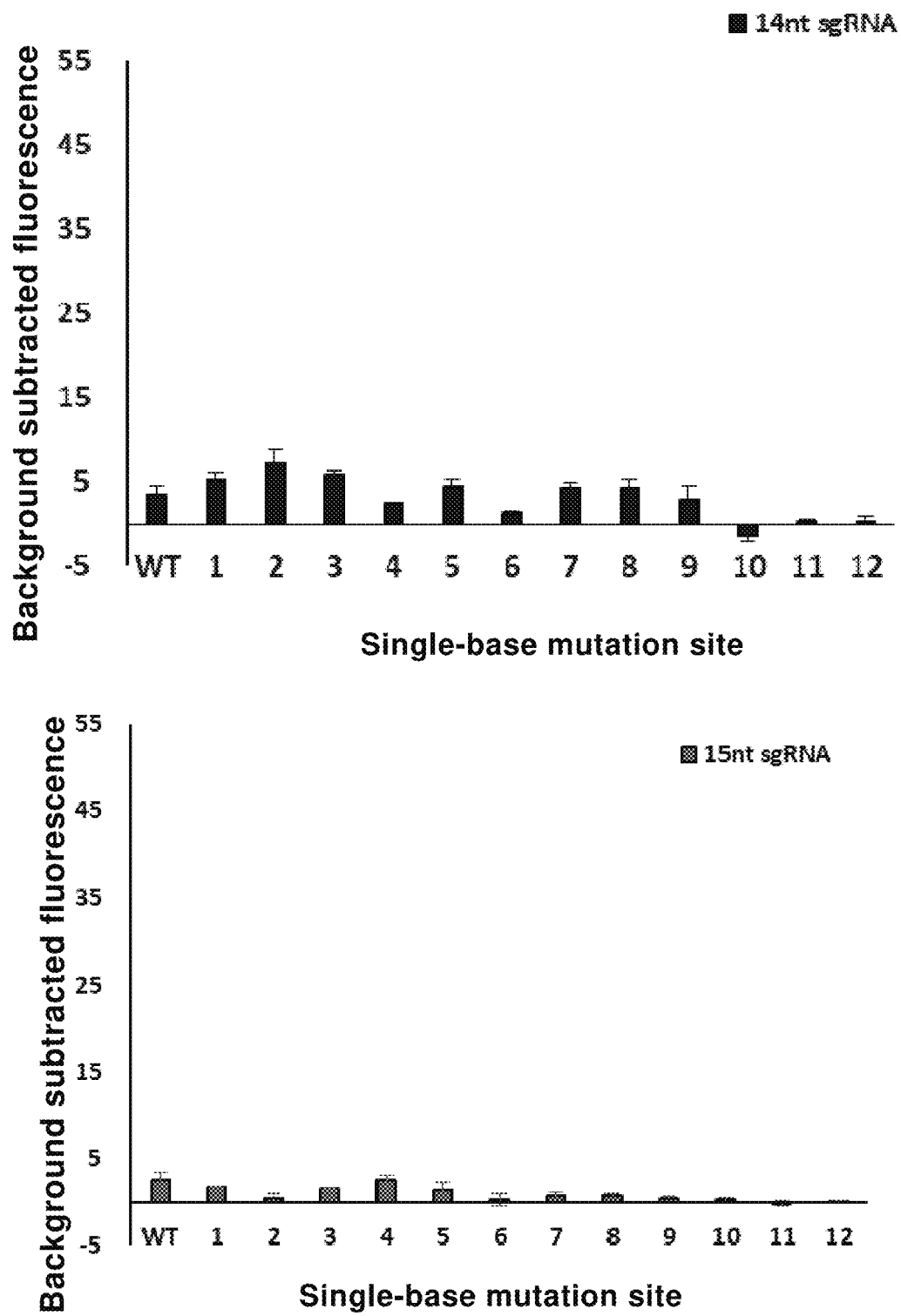
FIG. 7 shows the effect of single-base mutations in positions 1-12 of the ssDNA target sequence on the fluorescence intensity of Cas12b trans cleavage, using sgRNAs with different guiding sequence lengths.
Figure 7:
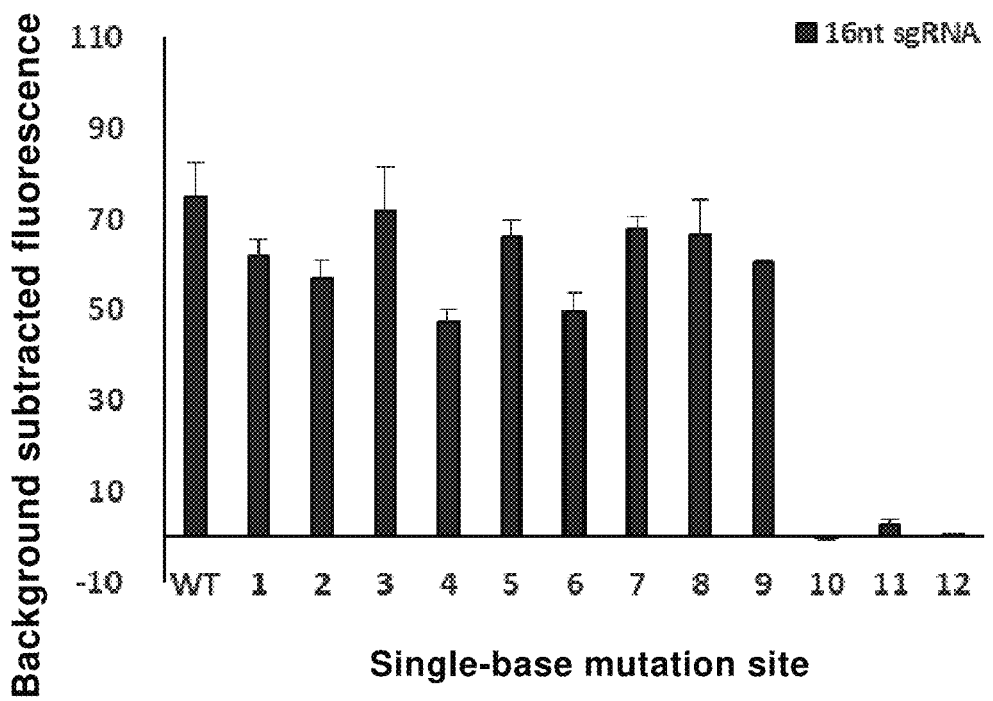
Figure 7:
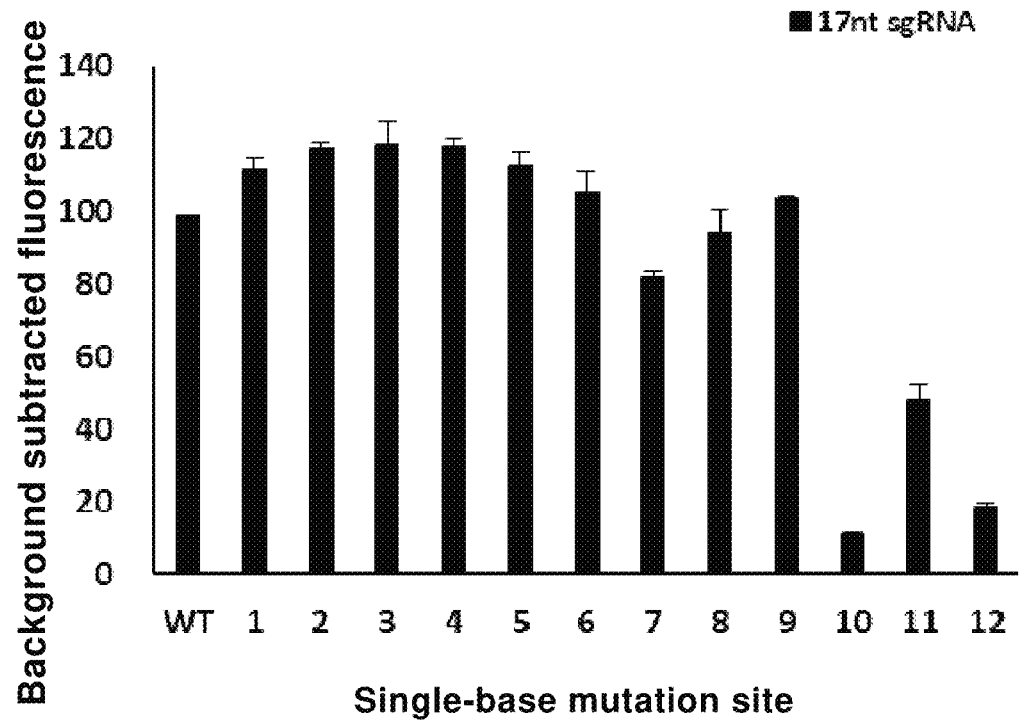
Figure 7:
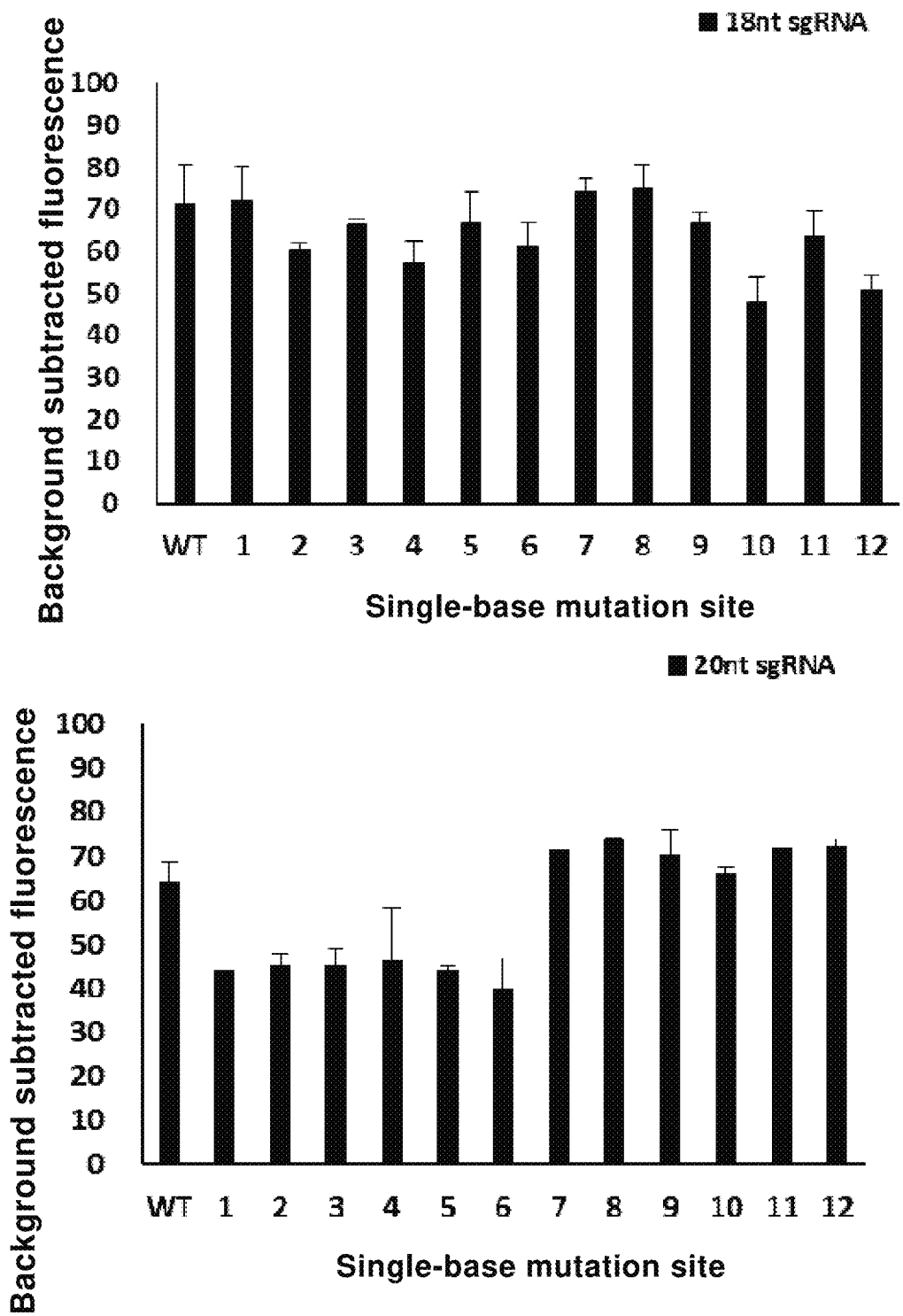

The SNP detection of target single-stranded DNA showed that when the sgRNA guide sequence had a length of 18 nt or 20 nt, the base mutation of positions 1-12 had little effect on the fluorescent signal generated by the trans cleavage. When the sgRNA guide sequence had a length of 14 nt or 15 nt, the fluorescence values including the wild-type control were very low. When the sgRNA guide sequence had a length of 16 nt, after the mutation of positions 10-12, the fluorescence value was significantly decreased compared with the control (FIG. 7).

Figure 8:
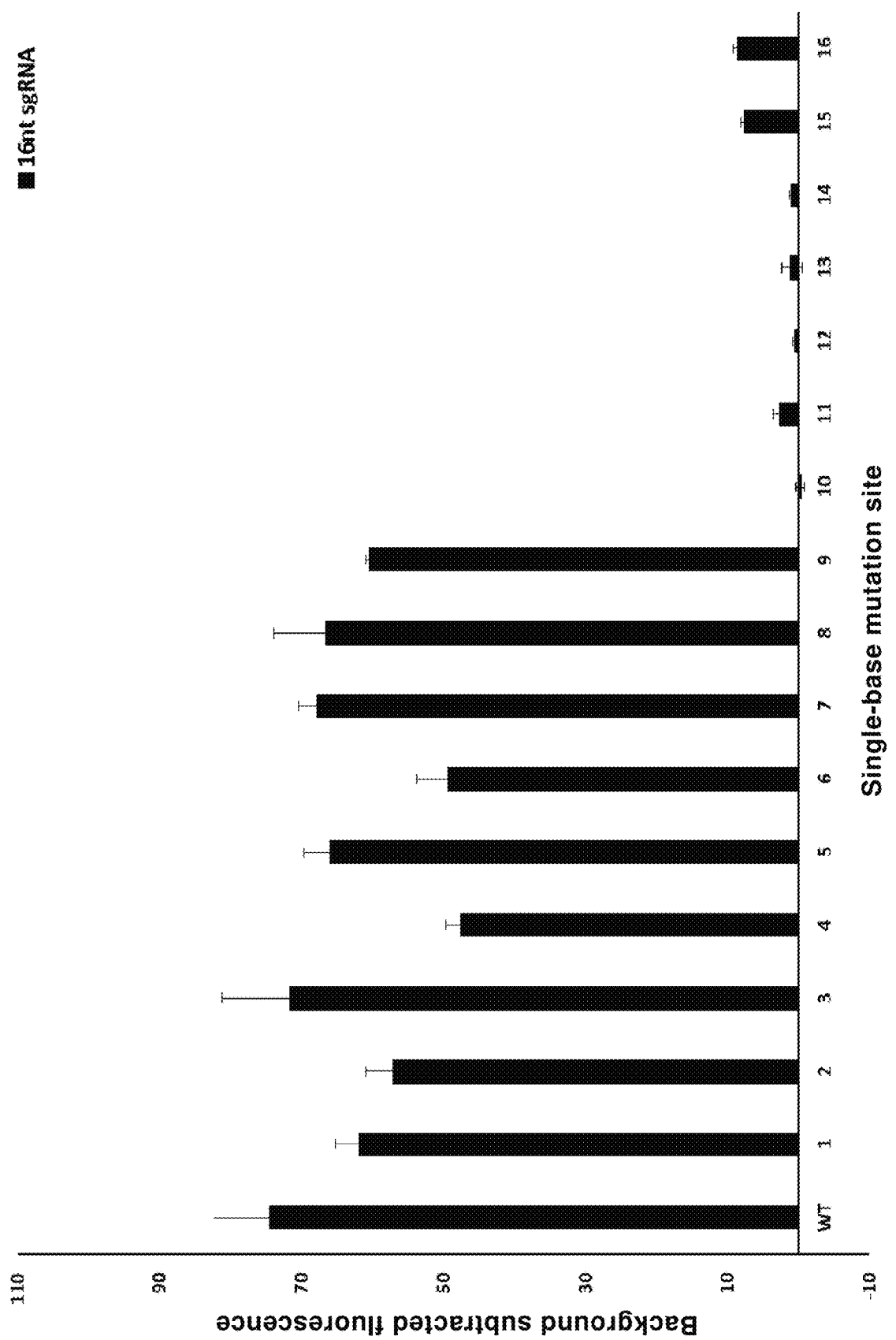
FIG. 8 shows the effect of single-base mutations in positions 1-16 of the ssDNA target sequence on the fluorescence intensity of Cas12b trans cleavage, using the sgRNA with a guiding sequence length of 16 nt.

Further research found that when the guide sequence was a 16 nt sgRNA, the base mutation of positions 10-16 had a very obvious effect on the fluorescence value, especially that the fluorescence value was almost undetectable after the mutation of positions 10-14 (FIG. 8).

In addition, when different positions of the target single-stranded DNA were mutated into different types of bases, there was no essential effect on the fluorescence value.

Figure 9:
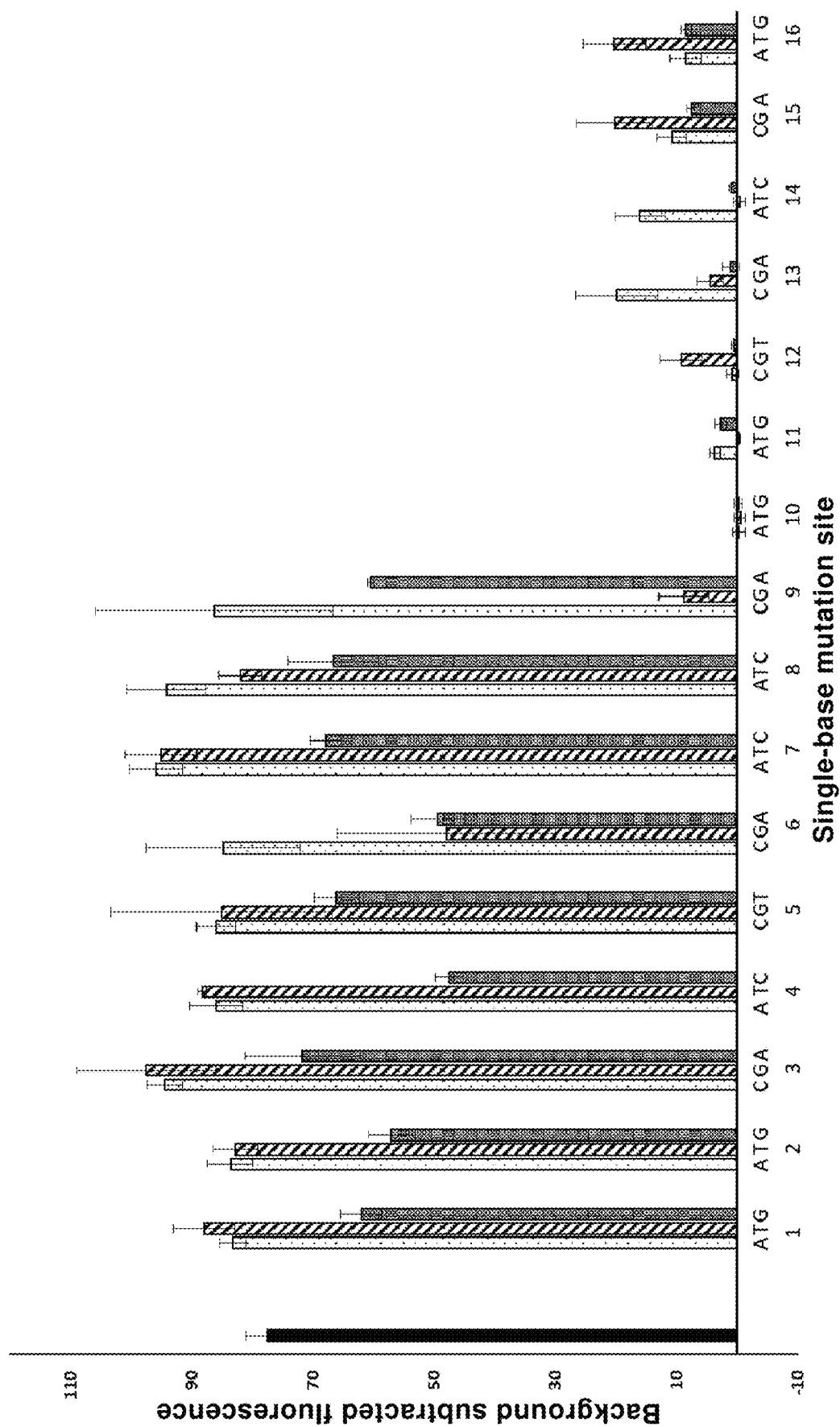
FIG. 9 shows the effect of single-base mutations into any one of the other 3 bases in positions 1-16 of the ssDNA target sequence on the fluorescence intensity of Cas12b trans cleavage, using the sgRNA with a guiding sequence length of 16 nt.

Wherein, only the mutation into G of position 9 greatly changed the fluorescence value (FIG. 9).

Figure 10:
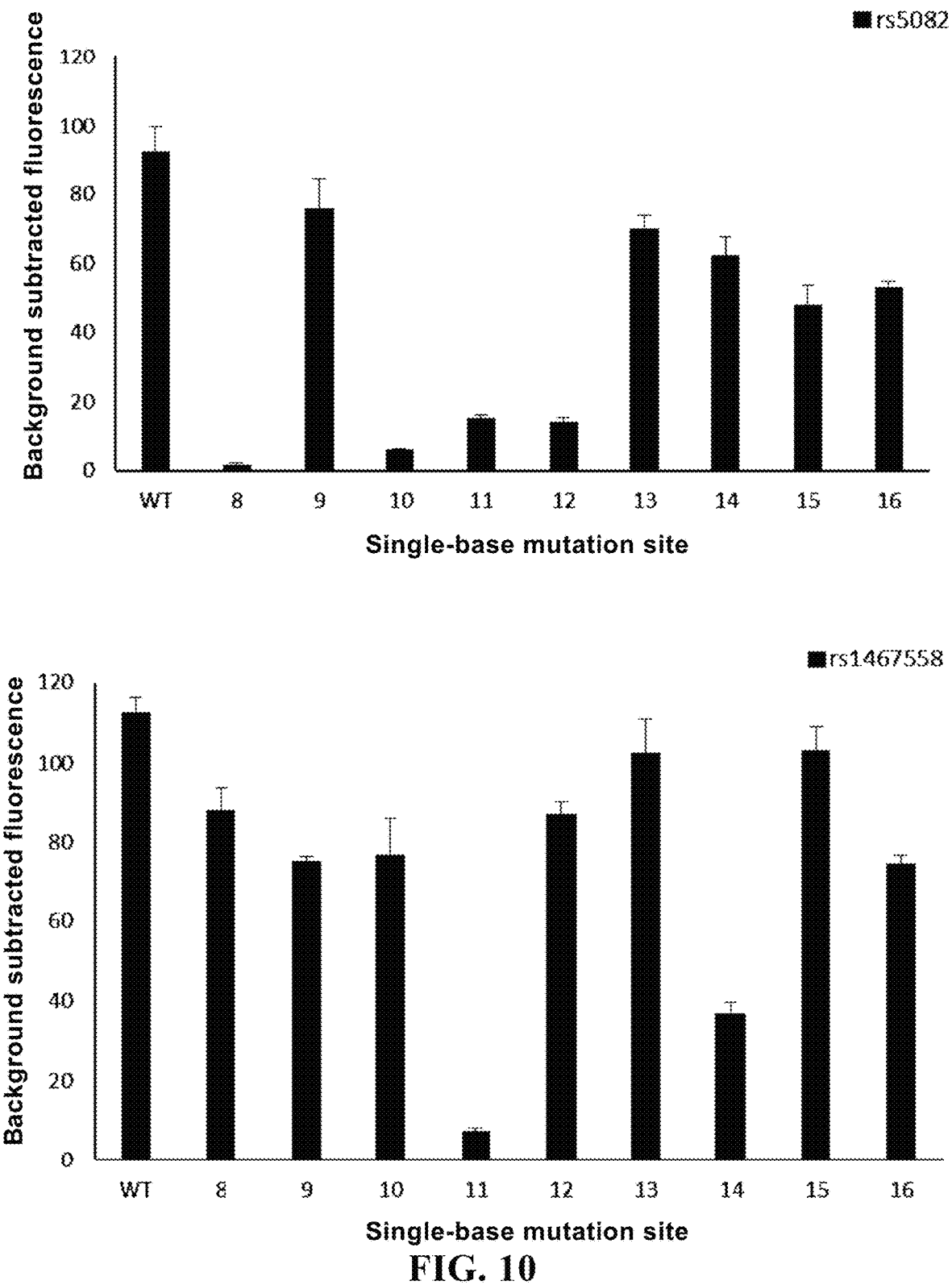
FIG. 10 shows the effect of single-base mutations in positions 8-16 of the three different ssDNA target sequences (rs5082, rs1467558 and rs2952768) on the fluorescence intensity of Cas12b trans cleavage, using the sgRNA with a guiding sequence length of 16 nt.
Figure 10:
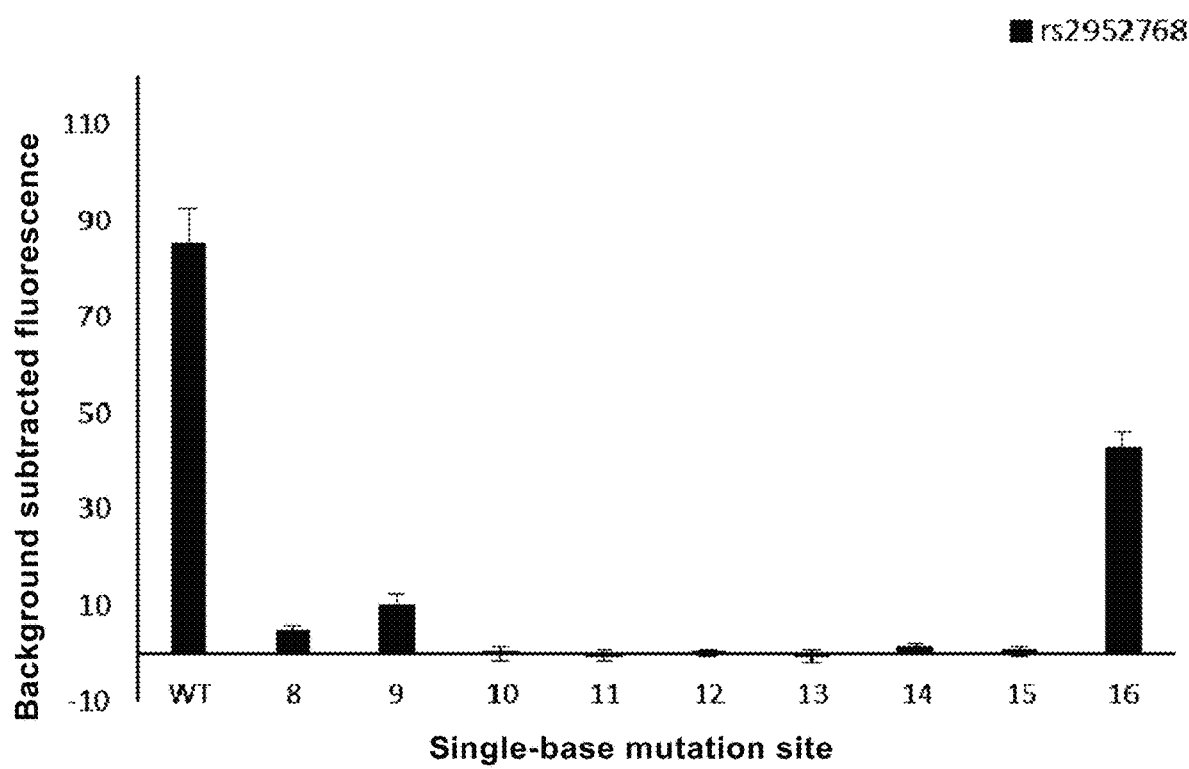

In addition, the inventors also tested three other target sequences. Although different sequences had different fluorescence changes for a certain site mutation, a position leading to significant change could still be found for each sequence among positions 8-16, such as positions 8, 10, 11 and 12 in rs5082, position 11 in rs1467558, positions 8-15 in rs2952768 (FIG. 10).

SNP test against dsDNA target: The method of the present invention is suitable for detecting nucleic acid mutations, including SNPs in dsDNA targets.

Figure 11:
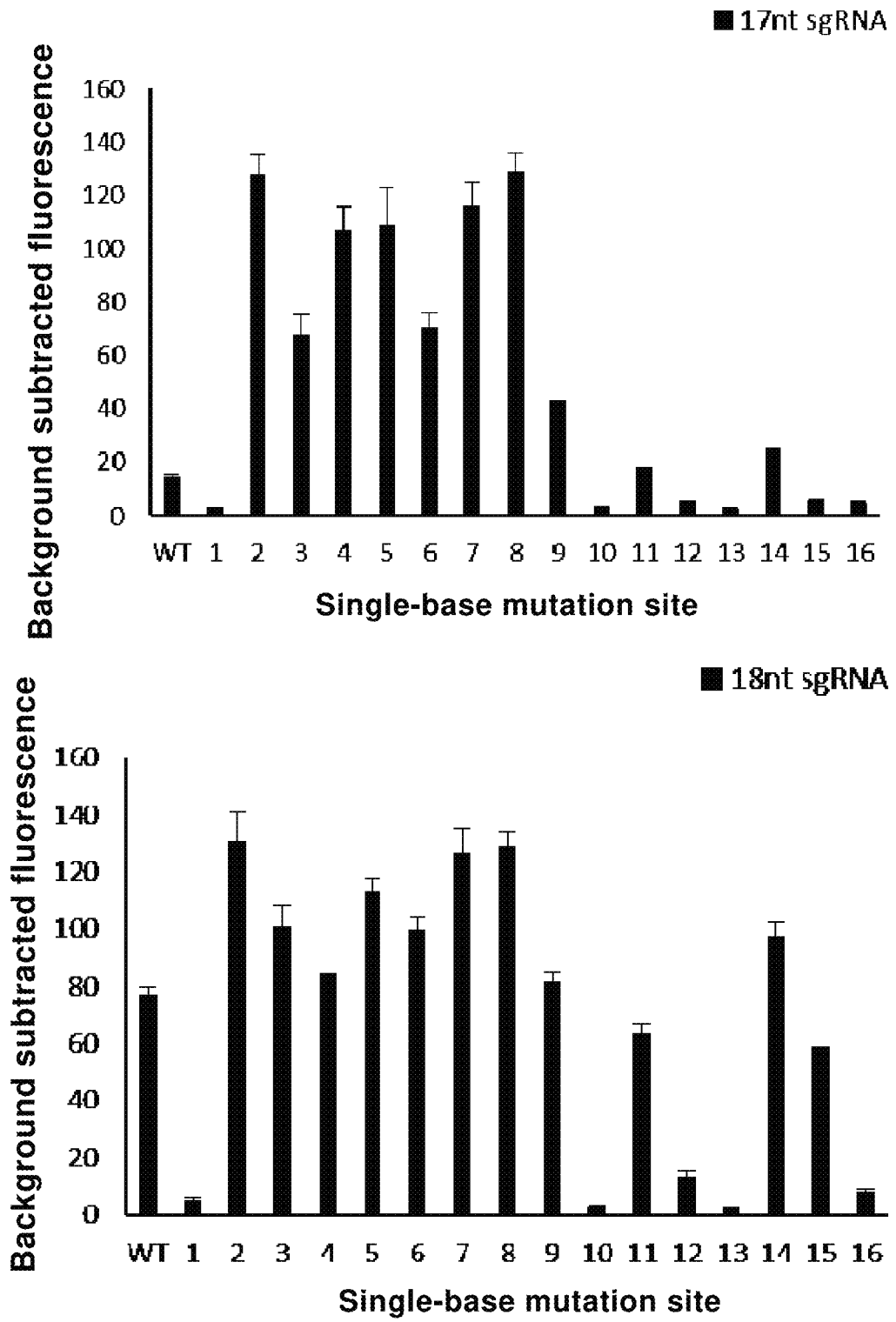
FIG. 11 shows the effect of single-base mutations in any one of positions 1-16 of the dsDNA target sequence on the fluorescence intensity of Cas12b trans cleavage, using sgRNAs with different guiding sequence lengths.
Figure 11:
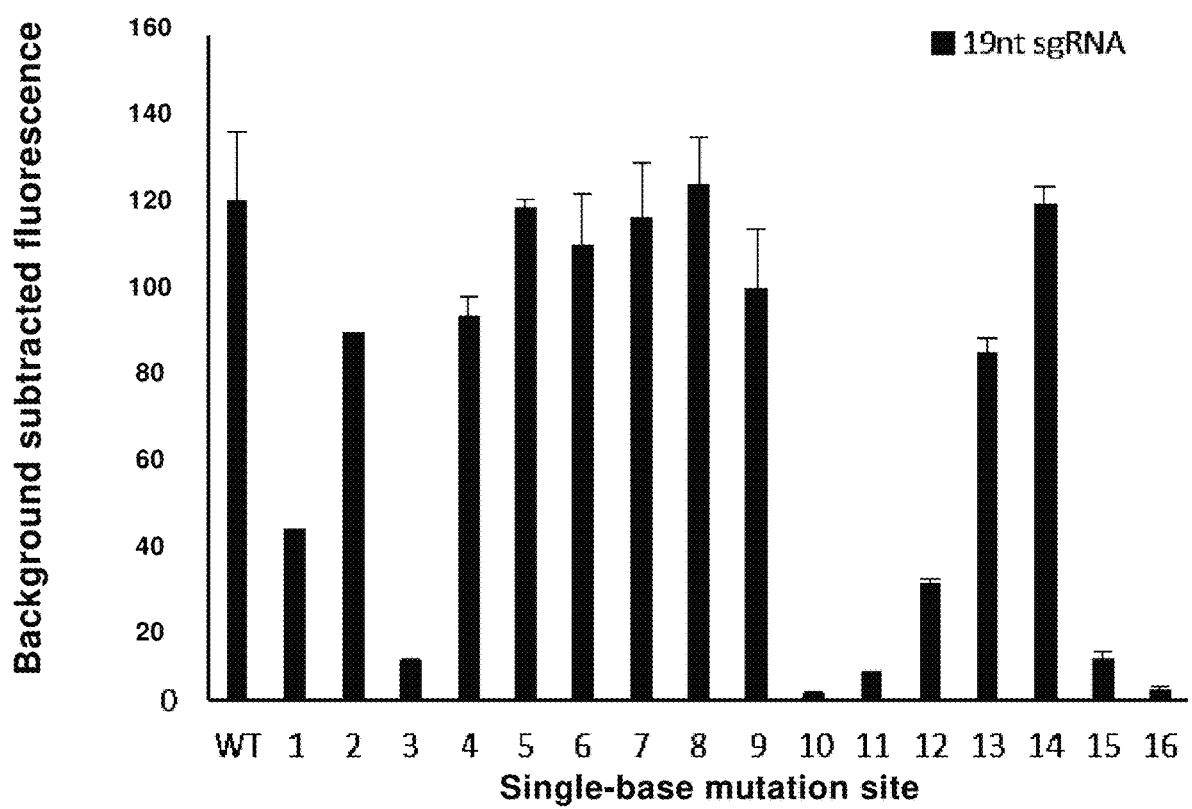
Figure 11:
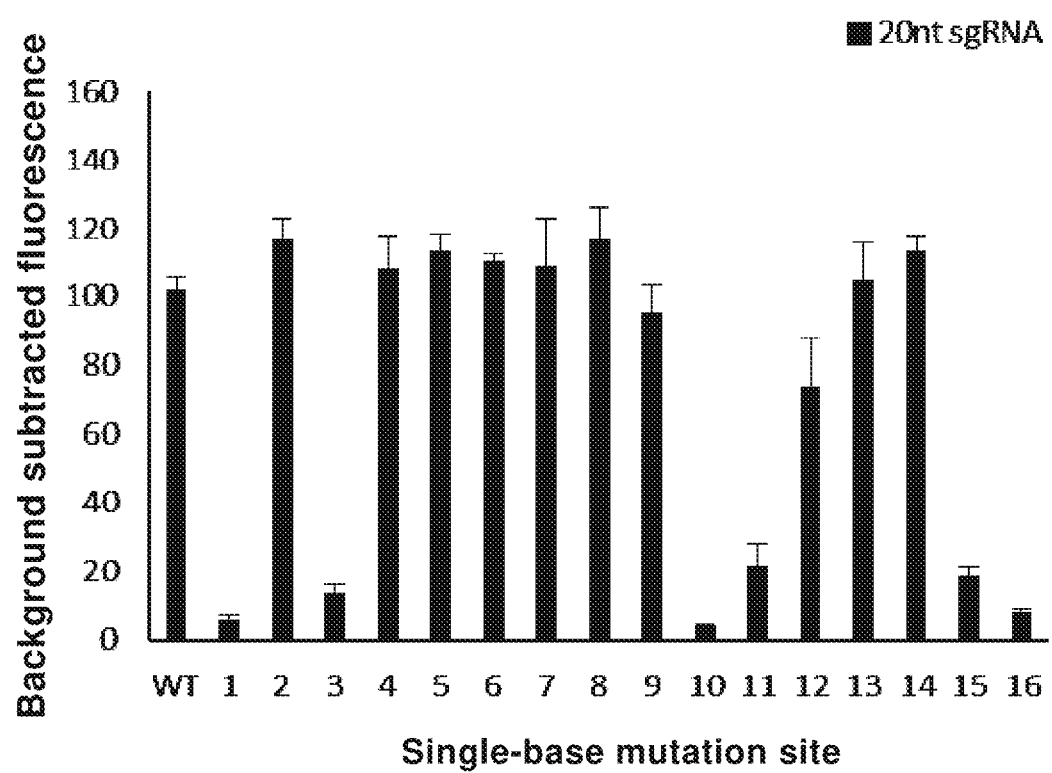

The SNP detection of target double-stranded DNA showed that the fluorescent signal generated by trans cleavage due to the single-base mutation is different from that of ssDNA. For example, sgRNA with a guiding sequence length of 18-20 nt has different degrees of sensitivity to base mutations at positions 10-16 (although the fluorescence signal also decreases to varying degrees after base mutations at positions 1 and 3) (FIG. 11). Generally, these sgRNAs are most sensitive to the 10th and 16th positions.

One-step detection at different temperatures: The present invention also provides a one-step detection that combines nucleic acid amplification and Cas12b.

Figure 12:
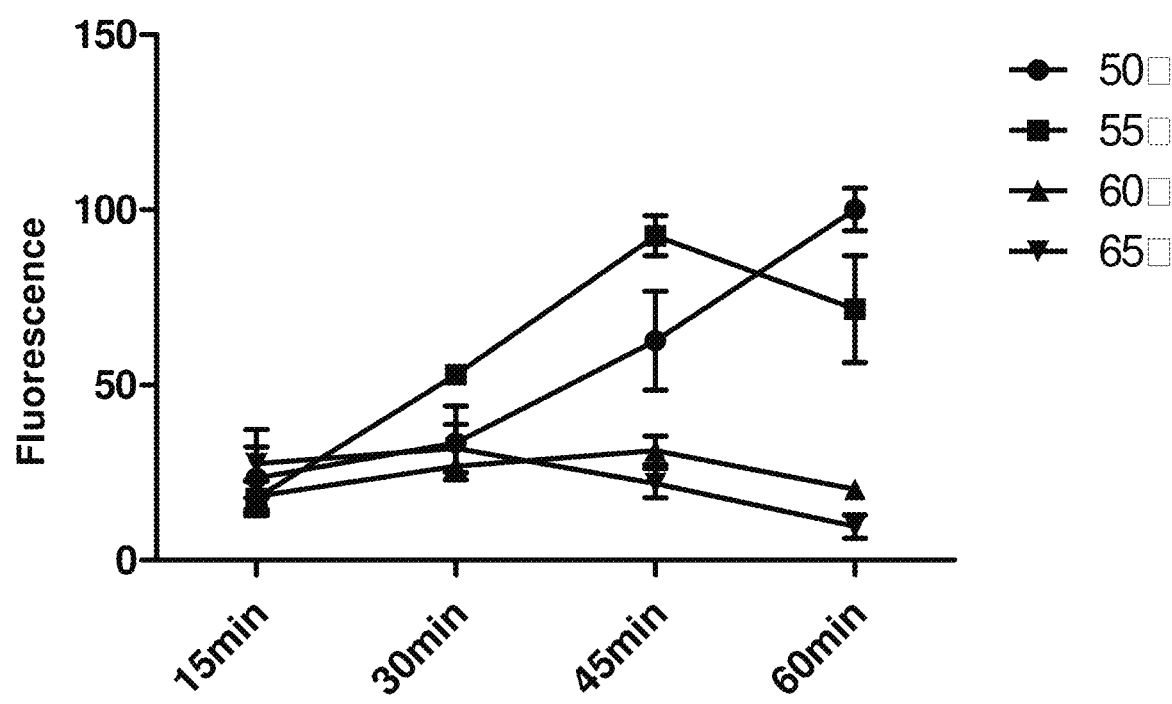
FIG. 12 shows the one-step reaction of LAMP and Cas12b detection at 50° C., 55° C., 60° C. and 65° C.

Preferably, LAMP amplification can be combined with Cas12b detection to realize one-step detection. In the present invention, the trans cleavage by Cas12b was tested under different temperature conditions (50° C., 55° C., 60° C., and 65° C., respectively). As shown in FIG. 12, at 50 and 55° C., one-step detection can be achieved. Especially at 55° C., the fluorescence value increase faster.

Test of target RNA: The method of the present invention is not only suitable for the detection of target DNA, but also suitable for the detection of target RNA. In the present invention, RNA can be reverse transcribed to the DNA form, and then the target sequence can be detected.

Figure 17:
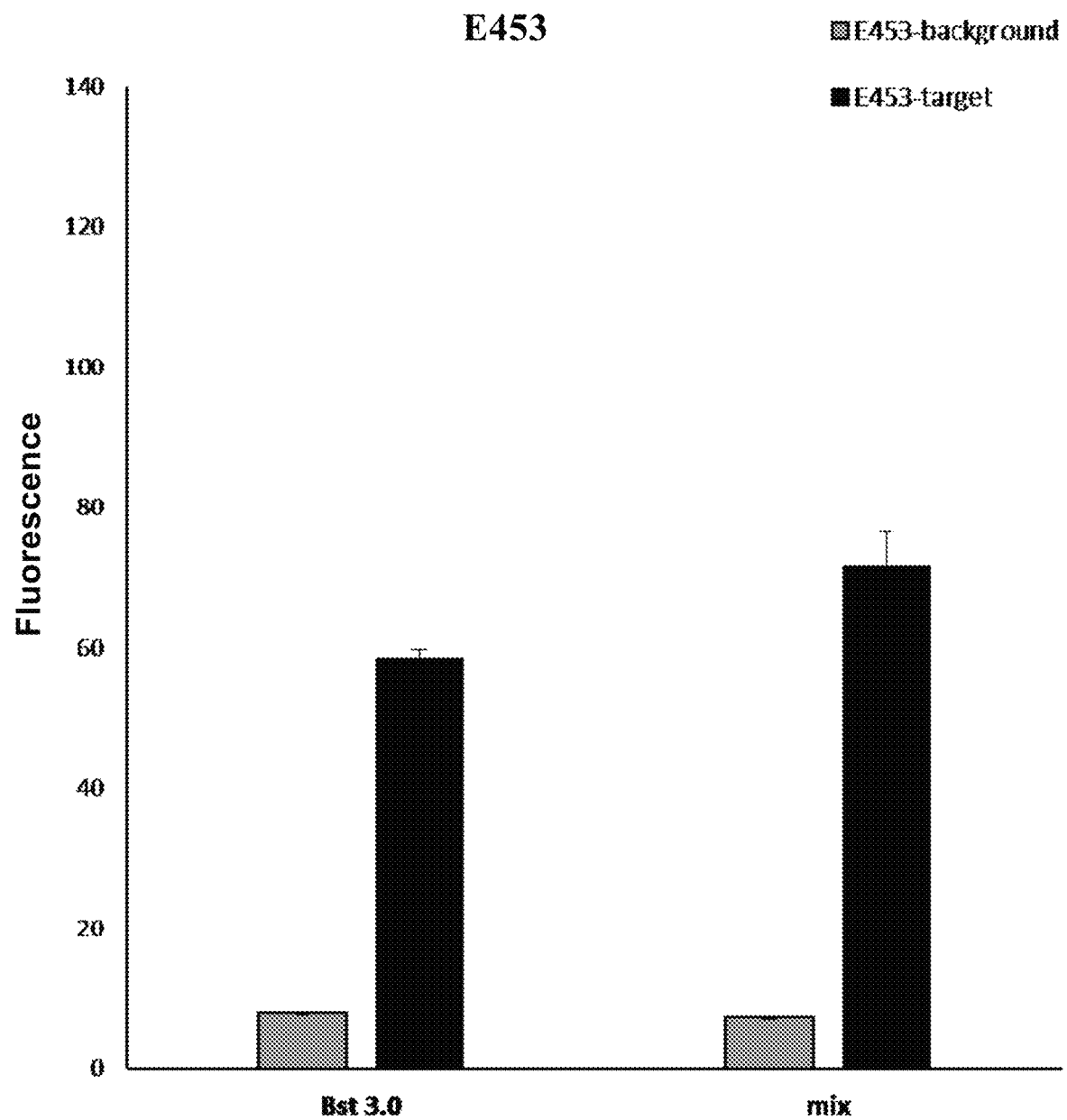
FIG. 17 shows the detection of RNA virus JEV (Japanese encephalitis virus) by HOLMES v2.0 (LAMP combined with Cas12b).
Figure 17:
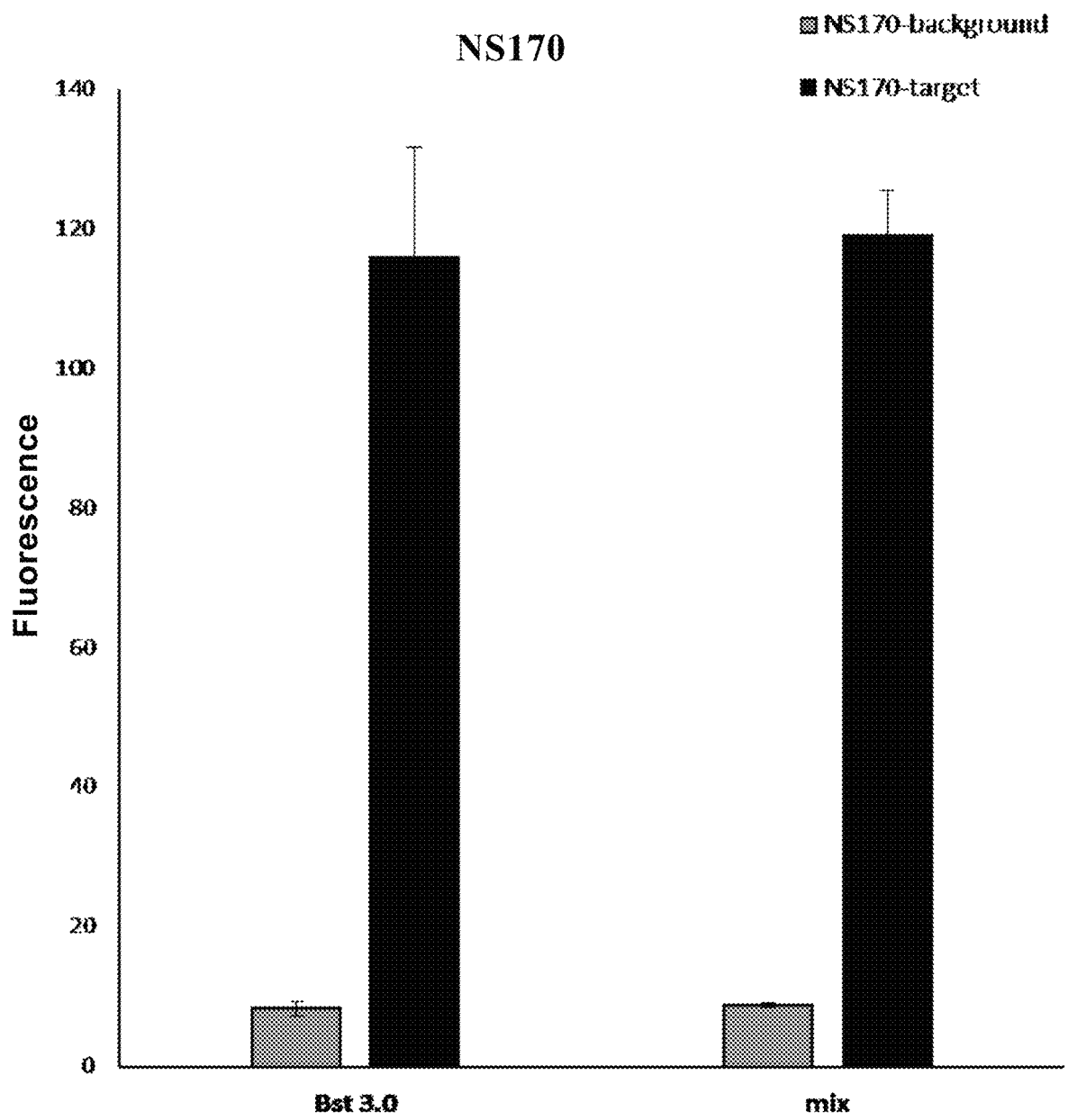

A preferred method is to add reverse transcriptase to the reaction system to achieve reverse transcription of RNA. Then, for example, Bst 2.0 DNA polymerase is used for amplification and Cas12b is used for achieving trans cleavage. Another method is to directly use Bst 3.0 DNA polymerase (this enzyme can amplify the RNA template to produce DNA) to directly realize the reverse transcription and amplification of RNA. (FIG. 17)

Quantitative test of trace DNA template: The method of the present invention can be used for quantitative detection.

Figure 18:
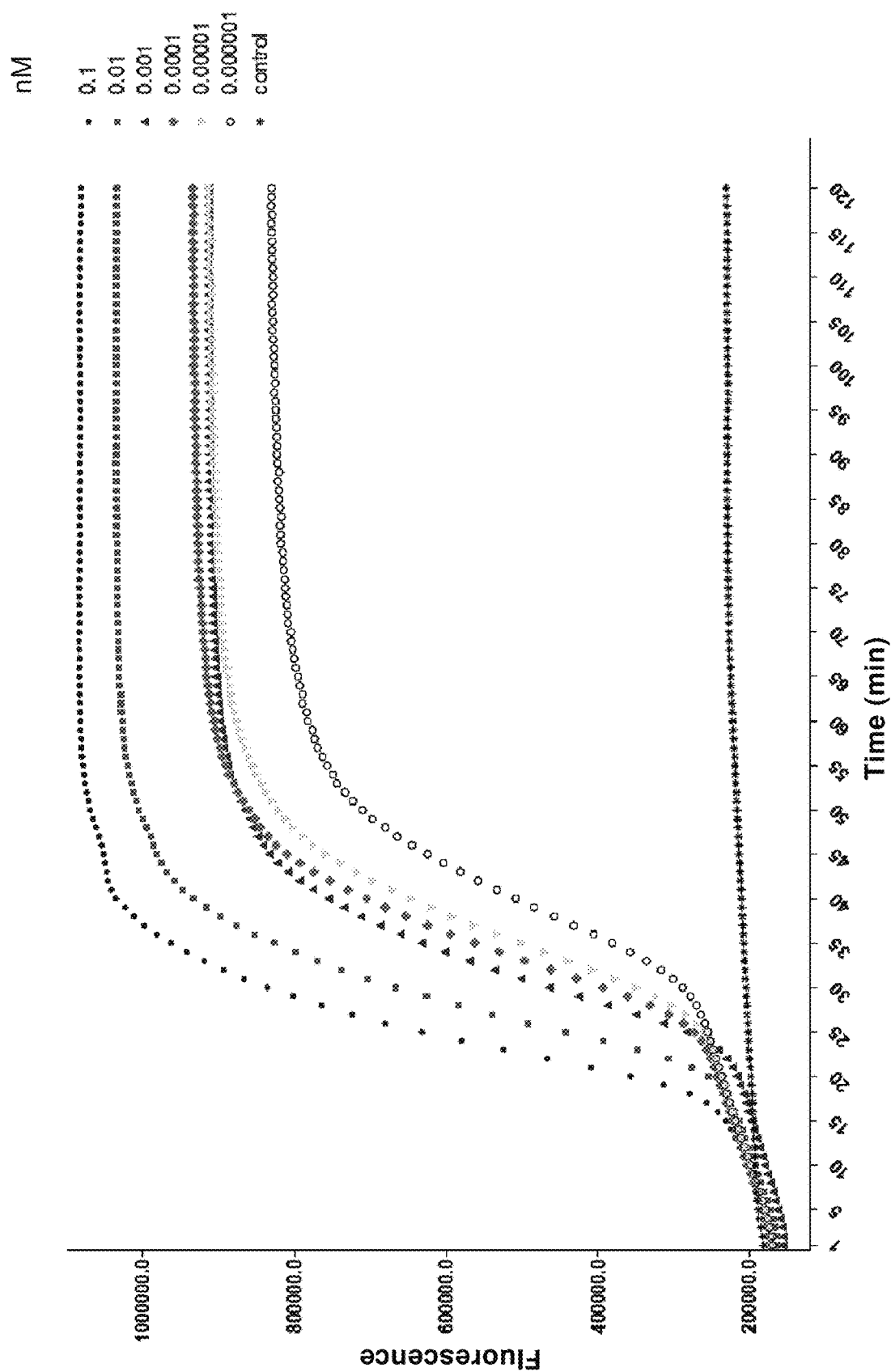
FIG. 18 shows the one-step quantification of trace DNA by HOLMES v2.0 (LAMP combined with Cas12b). By diluting the template DNA into different concentrations, LAMP-Cas12b one-step method was used for detecting the fluorescence value in real-time in a fluorometer (55° C. reaction).
Figure 19:
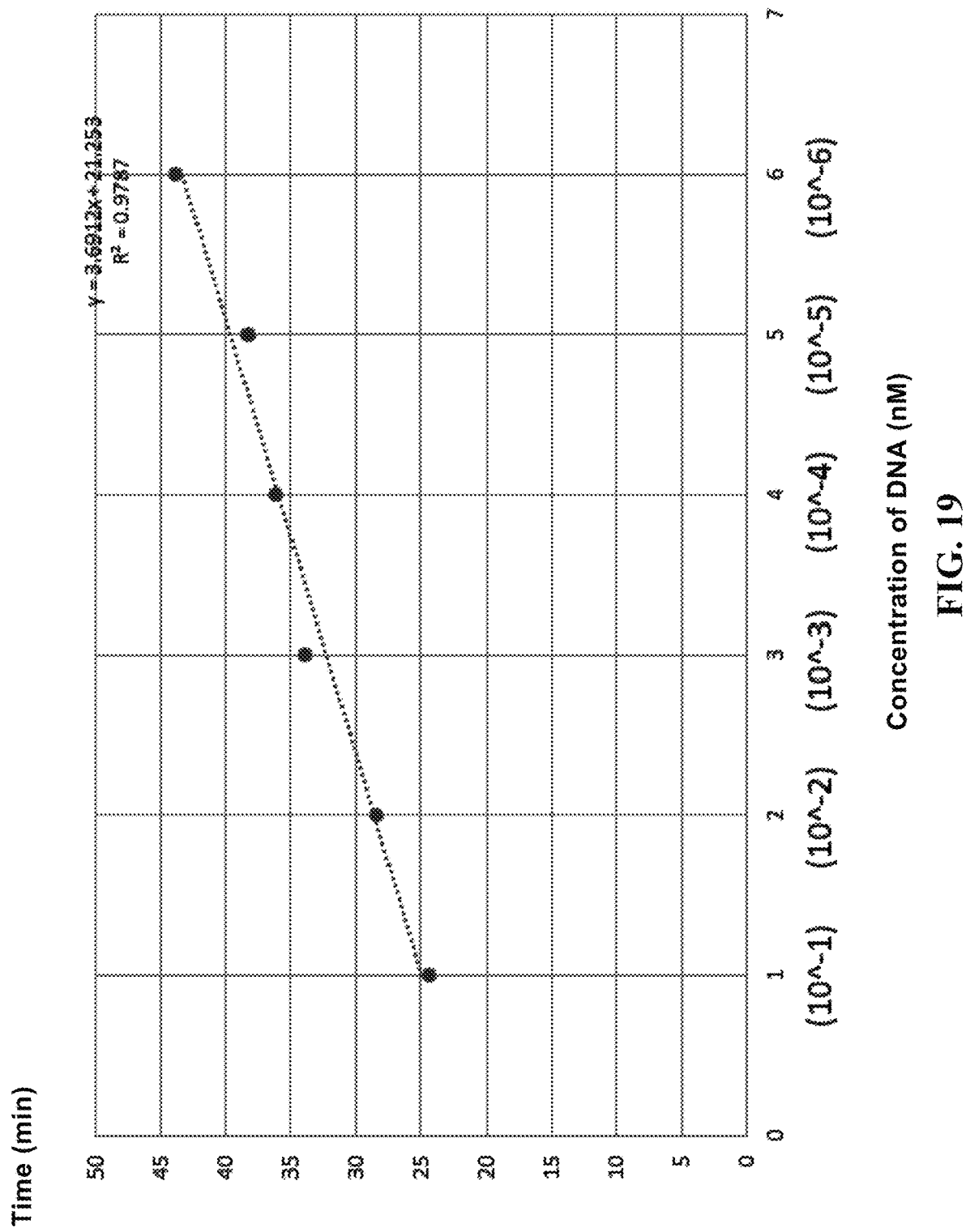
FIG. 19 shows the approximate straight trend line using the time point when the fluorescence value reaches 600,000 as the y-axis (using the data in FIG. 18), and using the 1 g absolute value of the concentration as the x-axis. This equation can be used for quantifying the target sequence.

In one example, a one-step method based on LAMP amplification and Cas12b was used at 55° C., thus quantitative testing the trace DNA. By diluting templates into different concentrations, the fluorescence value of trans cleavage was real-timely detected. Then a standard curve was made, the concentration of the target template sequence can be obtained by calculation (FIGS. 18 and 19).

Another quantitative detection is to combine the Cas12b-based detection method of the present invention with digital PCR technology (see "Digital HOLMES Method" below).

Design of Primers and sgRNA

Based on the teaching of the present invention, those skilled in the art can synthesize corresponding primers and/or sgRNAs according to practical needs, to perform the Cas12b-based nucleic acid detection of the present invention. In the present invention, some preferred designs of primers and sgRNA can refer to the following suggestions.

For primers, the design can refer to the following.

Situation 1. If the LAMP method is chosen for the previous amplification reaction, conventional methods for primer design can be used (http://primerexplorer.jp/elamp4.0.0/index.html). It is recommended to add LoopF and LoopB primers between primers area of F2/F3 and B2/B3, that is, 6 pairs of primers.

Situation 2. If the asymmetric PCR method is chosen for the previous amplification reaction, several primers should be prepared to test for the most suitable combination to produce single-stranded DNA.

Situation 3. For SNP detection, if there is a suitable PAM site near the site, solution of Situation 1 is used; if there is no suitable PAM site, PAM site can be brought into the primer, so that the product produces a PAM site. Usually the SNP site is 8-16 bases away from PAM, but the specific target sequence needs to be tested.

Situation 4. When it is difficult to find suitable LAMP amplification primers near the SNP site or it is difficult to introduce suitable PAM, methods such as asymmetric PCR amplification can be used to amplify single-stranded DNA.

For sgRNA design, the following situations can be referred.

Situation 1. For the detection of target genes, it is generally appropriate to select a 20 bp complementary paired sgRNA, for a target sequence with a PAM sequence.

Situation 2. For SNP detection, if double-stranded amplification such as LAMP is used in the amplification step, the position of the SNP site in the target sequence should be tested first. sgRNAs with a guiding sequence length of 18 nt is tested firstly for positions 10-16.

Situation 3. For SNP detection, if single-stranded amplification such as asymmetric PCR is used in the amplification step, the position of the SNP site in the target sequence should be tested first. sgRNAs with a guiding sequence length of 16 nt is tested firstly for positions 10-16, especially for positions 10-12.

Digital HOLMES Method

In the present invention, it also provides a technology that combines the HOLMES technology of the present invention with digital PCR (dPCR), referred to as "digital HOLMES method" for short.

Digital PCR is an absolute quantitative technology for nucleic acid molecules that has developed rapidly in recent years. At present, there are mainly two types, droplet digital PCR (ddPCR) and chip digital PCR (cdPCR). That is, the sample is dropletized or added to the chip before traditional PCR amplification, and the reaction system containing nucleic acid molecules is divided into thousands of nanoliter level reaction systems. Compared with traditional PCR, digital PCR additionally has a pre-processing step and a later fluorescence detection step. At present, digital PCR detection still requires the use of an traditional PCR machine to carry out the amplification step, and the conditions of the PCR reaction are stricter and the time required is longer (about 3-4 hours).

Using the HOLMES method combined with the current fluorescence reading instrument for chip digital PCR (i.e., the digital HOLMES method), absolute quantitative detection can be performed only at a constant temperature.

In addition, when LAMP or other methods for amplification is used in digital HOLMES, it can be amplified under a wide temperature range (50-70° C., or about 50-55° C.), without the requirement for precise temperature control like conventional PCR machines. Because Cas12b also has bypass cleavage activity in this temperature range, it can not only integrate effectively, but also perform amplification and bypass cleavage at the same time.

The present invention also provides a device for digital HOLMES detection, especially the device according to the seventh aspect of the present invention.

Therefore, digital HOLMES technology can be used for integrating pre-processing, amplification and detection into one instrument, which can not only reduce human operation errors, but also speed up detection and reduce instrument costs.

Kits

The invention also provides a kit, comprising a guiding RNA, a Cas12b protein and a nucleic acid probe. In addition, the kit of the present invention may also comprise other reagents, such as buffers, reagents required for amplification, reagents required for reverse transcription, or a combination thereof.

Typically, the kit of the present invention comprises:
i) a first container and a Cas12b protein located in the first container, wherein the Cas12b protein is Cas12b or a Cas protein having an activity similar to the bypass single-strand DNA cleavage activity of Cas12b;
ii) an optional second container and a guiding RNA located in the second container, wherein the guiding RNA directs the Cas protein to specifically bind to the target nucleic acid molecules;
iii) a third container and a nucleic acid probe (preferably a fluorescent probe) located in the third container;
iv) optionally a fourth container and a buffer located in the fourth container;
wherein, the target nucleic acid molecule is a target DNA.

Furthermore, the kit of the invention may further comprise:
v) a fifth container and a polymerase for amplifying target DNA located in the fifth container;
vi) an optional sixth container and a reverse transcriptase for reverse transcription located in the sixth container;
vii) a seventh container and dNTP for amplification reaction and/or reverse transcription reaction located in the seventh container.

In the present invention, one or more or all of the containers may be the same container or different containers.

The Main Advantages of the Invention are:

Using the characteristics of Cas12b, the inventors of the present invention have developed a method for specifically detecting nucleic acid molecules, which is called HOLMES (one-HOur Low-cost Multipurpose highly Efficient System version 2.0). It is characterized as a fast (1 hour), low cost, multi-purpose, efficient, and simple method. The method can be used in the fields of rapid pathogen detection, SNP detection and the like. Compared with the first generation of HOLMES based on Cas12a, the second generation of HOLMES based on the high temperature enzyme Cas12b has more advantages.

(1) Fast: When the test conditions are ready, it takes only about 1 hour from the time you get the sample to the time you get the test result.

(2) Low cost: There are no special materials or enzymes required in the experiment, and the amount of materials and reagents involved is small. It can be used for testing and analysis of trace amounts.

(3) Efficient: The method of the present invention has extremely high sensitivity and can detect DNA at a concentration of 10 aM.

(4) Multi-purpose: It can detect different nucleic acid samples, including DNA samples and RNA samples.

(5) Simple: There are no special complicated step. If the kit is ready and the program is set, only the steps of simply adding the sample and the like are needed.

(6) One-step reaction: the amplification reaction and detection reaction can be performed at the same time, to realize the one-step test.

(7) Isothermal: Since both LAMP amplification and Cas12b detection are under a constant temperature condition, the requirements for the instrument are lower.

(8) A wide range of reaction temperature: Cas12b can be used for detection at 45-65° C., so the requirements for the instrument are lower.

(9) Two enzymes can realize the amplification and detection of DNA or RNA: Since Bst 3.0 DNA polymerase has DNA polymerase activity using DNA or RNA as a template, only two enzymes, Bst 3.0 and Cas12b, are required to achieve the amplification and detection of DNA or RNA, which saves production costs.

(10) Highly sensitive SNP detection: By reasonably designing sites and sgRNA, it is possible to distinguish single base differences with high sensitivity.

(11) Quantitative detection can be achieved: Real-time detection of fluorescence by one-step HOLMES, or combined with the chip and detection system of a digital PCR instrument, can achieve quantitative detection of samples.

The invention is further illustrated below in conjunction with specific embodiments. It should be understood that the examples are not intended to limit the scope of the invention. The experimental methods in the following examples which do not specify the specific conditions are usually in accordance with conventional conditions, such as conditions described in Sambrook et al., Molecular Cloning: Laboratory Manual (New York: Cold Spring Harbor Laboratory Press, 1989), or in accordance with the conditions recommended by the manufacturer. Unless otherwise stated, percentages and parts are by weight.

In this application, unless otherwise specified, the Cas12b trans cleavage activity system comprises: 250 nM of sgRNA and 250 nM of Cas12b, and the reaction conditions are 48° C. 30 min.

Materials

1. The RNase inhibitor was purchased from TaKaRa. The high-fidelity DNA polymerase KOD FX was purchased from ToYoBo. The primers (oligonucleotides) were synthesized by Shanghai Biotech. The T7 RNA polymerase was purchased from Thermo. the RNA purification and concentration kit (RNA Clean & Concentrator™-5) was purchased from Zymo Research. Wizard® SV Gel and PCR Clean-Up System was purchased from Promega. The medium (e.g. Tryptone, Yeast Extract, etc.) were purchased from OXOID.
2. Medium formula: liquid LB (1% Tryptone, 0.5% Yeast extract, and 1% NaCl). When formulating solid LB, only 2% agar should be added to the liquid LB.

Example 1 Detection of Double-Stranded DNA (dsDNA) or Single-Stranded DNA (ssDNA) Targets Using Cas12b Protein Single-stranded DNA or double-stranded DNA (target T1) was selected as the target sequence to test the response values of Cas12b protein and sgRNA at different concentrations.

1. Preparation of guiding RNA (sgRNA)

First, the plasmid pUC18-sgRNA-T1 was constructed with pUC18 as the plasmid backbone. In the plasmid, the T7 promoter and the template DNA sequence for the transcription of sgRNA were inserted into pUC18. (Note: The sgRNA transcribed from this template is targeted to the sequence called T1 in this study.) In this preparation method, pUC18 plasmid was used as the template, and pUC18-1-F and pUC18-1-R were used as primers, and a first round of PCR was performed. Then T4 DNA Ligase was used to connect the PCR products, and the reaction product was transformed into DH10b. After being sequenced, the correct clone was obtained, which was called pUC18-sgRNA-T1-pre. Then pUC18-sgRNA-T1-pre was used as a template, and pUC18-2-F and pUC18-2-R were used as primers, and a second round of PCR was performed. PCR products were connected in the same way and transformed. And finally the correct sequenced plasmid pUC18-sgRNA-T1 was obtained.

Then, the plasmid pUC18-sgRNA-T1 was used as a template and T7-crRNA-F and sgRNA-T1-R were used as primers, and the DNA template required for in vitro transcription was amplified by PCR. Then DpnI added into the PCR product (1 μl of DpnI (10 U/μl) per 50 μl of PCR system), incubated in 37° C. water bath for 30 min. The plasmid DNA template was digested, and gel and PCR product column recovery kit (Promega) was used to recover the PCR product. The recovered PCR product was used as a template, and sgRNA (named sgRNA-T1) was synthesized using T7 High Yield Transcription Kit (Thermo). And the reaction was carried out overnight (12-16 h) at 37° C.

Finally, DNase I was added to the transcription system (2 μl of DNase I (5 U/μl) was added into per 50 μl of transcription system), incubated at 37° C. water bath for 30 min. Plasmid DNA template was eliminated, and RNA purification and concentration kit was used to purify RNA. And then NanoDrop 2000C was used for quantify and the product was stored in a refrigerator at −80° C. for later use.

2. Preparation of Target DNA (1) If the target DNA was single-stranded, an oligonucleotide target DNA (T1-R) was directly synthesized, which contains the 20 bp target sequence (T1) recognized by sgRNA.

(2) If the target DNA was double-stranded, two complementary oligonucleotides (T1-F; T1-R) were directly synthesized, which contain the 20 bp target sequence (T1) recognized by sgRNA. The two oligonucleotides were annealed, thus double-stranded target DNA was obtained. Specifically, the paired oligonucleotides (2 μM) were mixed in 1×PCR buffer (Transgen Biotech), with a total volume of 20 μL. And then the annealing procedure was performed: initially denatured at 95° C. for 5 minutes, then cooled down from 95° C. to 20° C., with a cooling rate of 1° C. per minute using a thermal cycler.

3. Cas12b Reaction (1) sgRNA annealing: sgRNA was diluted to an appropriate concentration, and annealed in a PCR machine. Annealing procedure: denatured at 75° C. for 5 min, then cooled down from 75° C. to 20° C., with a cooling rate of 1° C. per minute.

(2) Incubation of sgRNA with Cas12b: The annealed sgRNA was incubated with Cas12b at an equimolar concentration and placed at 30° C. for 20-30 min.

(3) Cas12b reaction: In a 20 μl reaction system, the mixture of sgRNA and Cas12b incubated in step (2) (the final concentration of both was 50, 100, 250 or 500 nM), the fluorescence and quenching probe (HEX-N12-BHQ1, with a final concentration of 500 nM), and 2 μl of 10×NEB Buffer 3.1 and 0.5 μl of RNase inhibitor (40 U/μl) were added. After mixed, it was reacted at 48° C. for 30 min. After that, it was inactivated by being heated at 98° C. for 5 min.

4. Detection of the Bypass Single-Stranded DNA Cleavage Activity of Cas12b Using a Fluorescence Microplate Reader Method 20 μL of the inactivated reaction solution was added to a 96-well plate and detected with a microplate reader (excitation light 535 nm, emission light 556 nm).

The results are shown in FIG. 2. When the concentration of Cas12b and sgRNA were 250 nM or 500 nM, both dsDNA and ssDNA as targets showed relatively high fluorescence intensity. When the concentration of Cas12b and sgRNA were reduced to 50 nM and 100 nM, ssDNA as the target sequence still showed high fluorescence intensity.

Example 2 Response Sensitivity Tested Using HOLMES v2.0 (LAMP Combined with Cas12b)

By detecting the excited fluorescence intensity of the fluorescent probe (HEX-N12-BHQ1), the concentration of target DNA required for the bypass single-stranded DNA cleavage activity of Cas12b was determined, that is, the sensitivity of the bypass single-stranded DNA cleavage reaction of Cas12b.

1. Preparation of sgRNA

First, the previously constructed plasmid pUC18-sgRNA-T1 was used as a template, and primers named sgRNA-DNMT1-3-F and sgRNA-DNMT1-3-R were designed. And the 20 bases targeting the target DNA T1 in the sgRNA was replaced with sgRNA targeting DNMT1-3 by PCR, thus obtaining another plasmid pUC18-sgRNA-DNMT1-3.

Then, the plasmid pUC18-sgRNA-DNMT1-3 was used as a template and T7-crRNA-F and ZLsgRNA-DNMT1-3-R were used as primers, and the DNA template required for in vitro transcription was amplified by PCR. Then DpnI was added into the PCR product (1 μl of DpnI (10 U/μl) per 50 μl of PCR system), incubated in 37° C. water bath for 30 min. The plasmid DNA template was digested, and gel and PCR product column recovery kit (Promega) was used to recover the PCR product. The recovered PCR product was used as a template, and sgRNA (named sgRNA-DNMT1-3) was synthesized using T7 High Yield Transcription Kit (Thermo). And the reaction was carried out overnight (12-16 h) at 37° C.

Finally, DNase I was added to the transcription system (2 μl of DNase I (5 U/μl) was added into per 50 μl of transcription system), incubated at 37° C. water bath for 30 min. Plasmid DNA was eliminated, and RNA purification and concentration kit was used to purify RNA. And then NanoDrop 2000C was used for quantify and the product was stored in a refrigerator at −80° C. for later use.

2. Preparation of Target DNA

For the target DNA, a first situation was that Cas12b was directly added to the reaction system without amplification. Method was as below:

(1) If the target DNA was single-stranded, an oligonucleotide with a length of 50 bp (DNMT1-3) was directly synthesized to be used as the target DNA, which contains the 20 bp target sequence (DNMT1-3) recognized by sgRNA.

(2) If the target DNA was double-stranded, two complementary oligonucleotides with a length of 50 bp (DNMT1-3(TTC PAM)-F; DNMT1-3(TTC PAM)-R) were directly synthesized, which contain the 20 bp target sequence (DNMT1-3) recognized by sgRNA. The two oligonucleotides were annealed, thus double-stranded target DNA was obtained. Specifically, the paired oligonucleotides (2 μM) were annealed in 1×PCR buffer (Transgen Biotech), with a total volume of 20 μL. And then the annealing procedure was performed: initially denatured at 95° C. for 5 minutes, then cooled down from 95° C. to 20° C., with a cooling rate of 1° C. per minute using a thermal cycler.

(3) The single-stranded or double-stranded target DNA was diluted to 2 μM, 0.2 μM, 0.02 μM, 0.002 μM, and 0.0002 μM for use.

A second situation was that the fragment containing the target sequence (DNMT1-3) was inserted into a plasmid vector and amplified through the LAMP reaction.

(1) pEasy-Blunt Zero Cloning Kit from Transgen was used to insert the fragment containing the target sequence (DNMT1-3) into the pEasy-Blunt Zero Cloning Vector, and the correct clone was obtained after sequencing verification.

(2) LAMP Amplification Reaction

The above plasmid was used as a template to carry out the LAMP amplification reaction. the template were added respectively with 0, 1 nM, 0.1 nM, and concentration with a 10-fold dilution to $10^{-11}$ nM. The total volume of each reaction system was 25 μL. 1.6 μM of LAMP-DNM-FIP and LAMP-DNM-BIP, 0.2 μM of LAMP-DNM-F3 and LAMP-DNM-B3, and 0.4 μM of LAMP-DNM-LoopF and LAMP-DNM-LoopB were used as the primers. The kit used for LAMP reaction was WarmStart® LAMP Kit (NEB). The LAMP reaction program was 65° C. 30 min. After the LAMP was completed, the product was inactivated at 85° C. for 10 min, and then directly used in the Cas12b reaction.

3. Cas12b Reaction (1) sgRNA annealing: sgRNA was diluted to an appropriate concentration (5 μM), and annealed in a PCR machine. Annealing procedure: denatured at 75° C. for 5 min, then cooled down from 75° C. to 20° C., with a cooling rate of 1° C. per minute.

(2) Incubation of sgRNA with Cas12b: The annealed sgRNA was incubated with Cas12b at an equimolar concentration and placed at 30° C. for 20-30 min.

(3) Cas12b reaction: In a 20 μl reaction system, the mixture of sgRNA and Cas12b incubated in step (2) (the final concentration of both was 250 nM), 1 μl of target DNA or 1 μl of the LAMP product, the fluorescence probe (HEX-N12-BHQ1, with a final concentration of 500 nM), and 2 μl of 10×NEB Buffer 3.1 and 0.5 μl of RNase inhibitor (40 U/μl) were added. After mixed, it was reacted at 48° C. for 30 min. After that, it was inactivated by being heated at 98° C. for 5 min.

4. Detection of the bypass single-stranded DNA cleavage activity of Cas12b using a fluorescence microplate reader method 20 μL of the inactivated reaction solution was added to a 96-well plate and detected with a microplate reader (excitation light 535 nm, emission light 556 nm).

As shown in FIG. 5, it can be seen that Cas12b can detect single-stranded or double-stranded DNA at a concentration of 1 nM. When combined with LAMP amplification, Cas12b (i.e., HOLMES v2.0 method) can detect DNA at a concentration of $10^{-8}$ nM (FIG. 6).

Example 3 Detection of Single-Base Mutation Target by Cas12b

Single-stranded DNA or double-stranded DNA was used as the target sequence to test the change of the fluorescent signal of Cas12b trans cleavage when there was a single-base mutation in the target DNA, thereby detecting single-base mutations.

1. Preparation of Guiding RNA (sgRNA)

Plasmid pUC18-sgRNA-DNMT1-3 was used as template, T7-crRNA-F was used as upstream primer, and oligonucleotides containing guide sequences complementary to different targets were used as downstream primers. And the DNA template required for in vitro transcription was amplified by PCR. Then DpnI was added into the PCR product (1 μl of DpnI (10 U/μl) per 50 μl of PCR system), incubated in 37° C. water bath for 30 min. The plasmid DNA template was digested, and gel and PCR product column recovery kit (Promega) was used to recover the PCR product. The recovered PCR product was used as a template, and full-length sgRNA (with a guiding sequence length of 20 nt) or truncated sgRNA (with a guiding sequence length of less than 20 nt) was synthesized using T7 High Yield Transcription Kit (Thermo). And the reaction was carried out overnight (12-16 h) at 37° C.

Then DNase I was added to the transcription system (2 μl of DNase I (5 U/μl) was added into per 50 μl of transcription system), incubated at 37° C. water bath for 30 min. DNA template was eliminated, and RNA purification and concentration kit was used to purify RNA. And then NanoDrop 2000C was used for quantify and the product was stored in a refrigerator at −80° C. for later use.

2. Preparation of Target DNA
   (1) If the target DNA was single-stranded, an oligonucleotide with a length of 50 bp was directly synthesized to be used as the target DNA, which contains the target sequence recognized by sgRNA.
   (2) If the target DNA was double-stranded, two complementary oligonucleotides with a length of 50 bp were directly synthesized, which contain the target sequence recognized by sgRNA. The two oligonucleotides were annealed, thus double-stranded target DNA was obtained. Specifically, the paired oligonucleotides (1 μM) were annealed in 1×PCR buffer (Transgen Biotech), with a total volume of 20 μL. And then the annealing procedure was performed: initially denatured at 95° C. for 5 minutes, then cooled down from 95° C. to 20° C., with a cooling rate of 1° C. per minute using a thermal cycler.

3. Cas12b Reaction
   (1) sgRNA annealing: sgRNA was diluted to an appropriate concentration (5 μM), and annealed in a PCR machine. Annealing procedure: denatured at 75° C. for 5 min, then cooled down from 75° C. to 20° C., with a cooling rate of 1° C. per minute.
   (2) Incubation of sgRNA with Cas12b: The annealed sgRNA was incubated with Cas12b at an equimolar concentration and placed at 30° C. for 20-30 min.
   (3) Cas12b reaction: In a 20 μl reaction system, the mixture of sgRNA and Cas12b incubated in step (2) (the final concentration of both was 250 nM), target DNA (with a final concentration of 50 nM), the fluorescence and quenching probe (HEX-N12-BHQ1, with a final concentration of 500 nM), and 2 μl of 10×NEB Buffer 3.1 and 0.5 μl of RNase inhibitor (40 U/μl) were added. After mixed, it was reacted at 48° C. for 30 min. After that, it was inactivated by being heated at 98° C. for 5 min.

4. Detection of the Bypass Single-Stranded DNA Cleavage Activity of Cas12b Using a Fluorescence Microplate Reader Method 20 μL of the inactivated reaction solution was added to a 96-well plate and then detected with a microplate reader (excitation light 535 nm, emission light 556 nm).

First of all, as shown in FIG. 7, as for the target sequence of DNMT1-3, and for the target single-stranded DNA, when the sgRNA guide sequence was 20 nt, the effect of base mutations at positions 1-12 on the fluorescence signal generated by trans cleavage was not significant. When the sgRNA guide sequence had a length of 14 nt or 15 nt, the fluorescence values including the control were very low. When the sgRNA guide sequence had a length of 16 nt, after the mutation of positions 10-12, the fluorescence value was significantly decreased.

Further research found that, as shown in FIG. 8, the base mutation of positions 10-16 had a very obvious effect on the fluorescence value, especially that the fluorescence value was almost undetectable after the mutation of positions 10-14. Then different positions of the target single-stranded DNA were mutated into different types of bases, and there was no essential effect on the fluorescence value. Wherein, only the mutation into G of position 9 greatly changed the fluorescence value (FIG. 9).

Then the inventors also tested three other target sequences. Although different sequences had different fluorescence changes for a certain site mutation, a position leading to significant change could still be found for each sequence among positions 8-16, such as positions 8, 10, 11 and 12 in rs5082, position 11 in rs1467558, positions 8-15 in rs2952768 (FIG. 10).

For the target double-stranded DNA, as shown in FIG. 11, it shows that the fluorescent signal generated by trans cleavage due to the influence from the single-base mutation was different from that of ssDNA. Taking the target sequence of DNMT1-3 as an example, sgRNA with a guiding sequence length of 18-20 was sensitive to base mutations at positions 10-16. In addition, in this example, several kinds of sgRNAs are most sensitive to the 10th and 16th positions.

One-step reaction of LAMP and Cas12b detection was realized at 50° C., 55° C., 60° C. and 65° C. (FIG. 12).

Example 4 Detection of E. coli and Other Microorganisms in Environmental Water

The E. coli gyrB gene was selected as the detection target to indirectly detect E. coli and other microorganisms in the water body and determine the detection limit.

1. Preparation of Guiding RNA (sgRNA)

Plasmid pUC18-sgRNA-DNMT1-3 was used as a template, and T7-crRNA-F was used as an upstream primer, and ZL-gyrB-crRNA2-R was used as a downstream primer.

The DNA template required for in vitro transcription was amplified by PCR. Then DpnI was added into the PCR product (1 μl of DpnI (10 U/μl) per 50 μl of PCR system), incubated in 37° C. water bath for 30 min. The plasmid DNA template was digested, and gel and PCR product column recovery kit (Promega) was used to recover the PCR product. The recovered PCR product was used as a template, and sgRNA was synthesized using T7 High Yield Transcription Kit (Thermo). And the reaction was carried out overnight (12-16 h) at 37° C.

Then DNase I was added to the transcription system (2 μl of DNase I (5 U/μl) was added into per 50 μl of transcription system), incubated at 37° C. water bath for 30 min. DNA template was eliminated, and RNA purification and concentration kit was used to purify RNA. And then NanoDrop 2000C was used for quantify and the product was stored in a refrigerator at −80° C. for later use.

2. LAMP Amplification Reaction

When E. coli MG1655 was cultivated to an $OD_{600}$ of 1.0, a part of the bacterial solution was placed at 100° C. for 15 min. Then the LAMP amplification reaction was performed. The template was added with the bacterial solution of different dilutions, wherein the diluted solutions were with an $OD_{600}$ of 0, $5\times10^{-3}$, $5\times10^{-4}$, to $5\times10^{-9}$, respectively.

After coating test, an $OD_{600}$ of $5\times10^{-3}$ contained about 7000 bacteria. The total volume of each reaction system was 25 μL. 1.6 μM of LAMP-gyrB-FIP and LAMP-gyrB-BIP, 0.2 μM of LAMP-gyrB-F3 and LAMP-gyrB-B3, and 0.4 μM of LAMP-gyrB-LoopF and LAMP-gyrB-LoopB were used as the primers. The kit used for LAMP reaction was WarmStart® LAMP Kit (NEB). The LAMP reaction program was 65° C. 30 min. After the LAMP was completed, the product was inactivated at 85° C. for 10 min, and then directly used in the Cas12b reaction.

3. Cas12b Reaction
   (1) sgRNA annealing: sgRNA was diluted to an appropriate concentration (5 μM), and annealed in a PCR machine. Annealing procedure: denatured at 75° C. for 5 min, then cooled down from 75° C. to 20° C., with a cooling rate of 1° C. per minute.

(2) Incubation of sgRNA with Cas12b: The annealed sgRNA was incubated with Cas12b at an equimolar concentration and placed at 30° C. for 20-30 min.

(3) Cas12b reaction: In a 20 μl reaction system, the mixture of sgRNA and Cas12b incubated in step (2) (the final concentration of both was 250 nM), 1 μl of the LAMP product, the fluorescence probe (HEX-N12-BHQ1, with a final concentration of 500 nM), and 2 μl of 10×NEB Buffer 3.1 and 0.5 μl of RNase inhibitor (40 U/μl) were added. After mixed, it was reacted at 48° C. for 30 min. After that, it was inactivated by being heated at 98° C. for 5 min.

4. Detection of the Bypass Single-Stranded DNA Cleavage Activity of Cas12b Using a Fluorescence Microplate Reader Method 20 μL of the inactivated reaction solution was added to a 96-well plate and detected with a microplate reader (excitation light 535 nm, emission light 556 nm).

Figure 13:
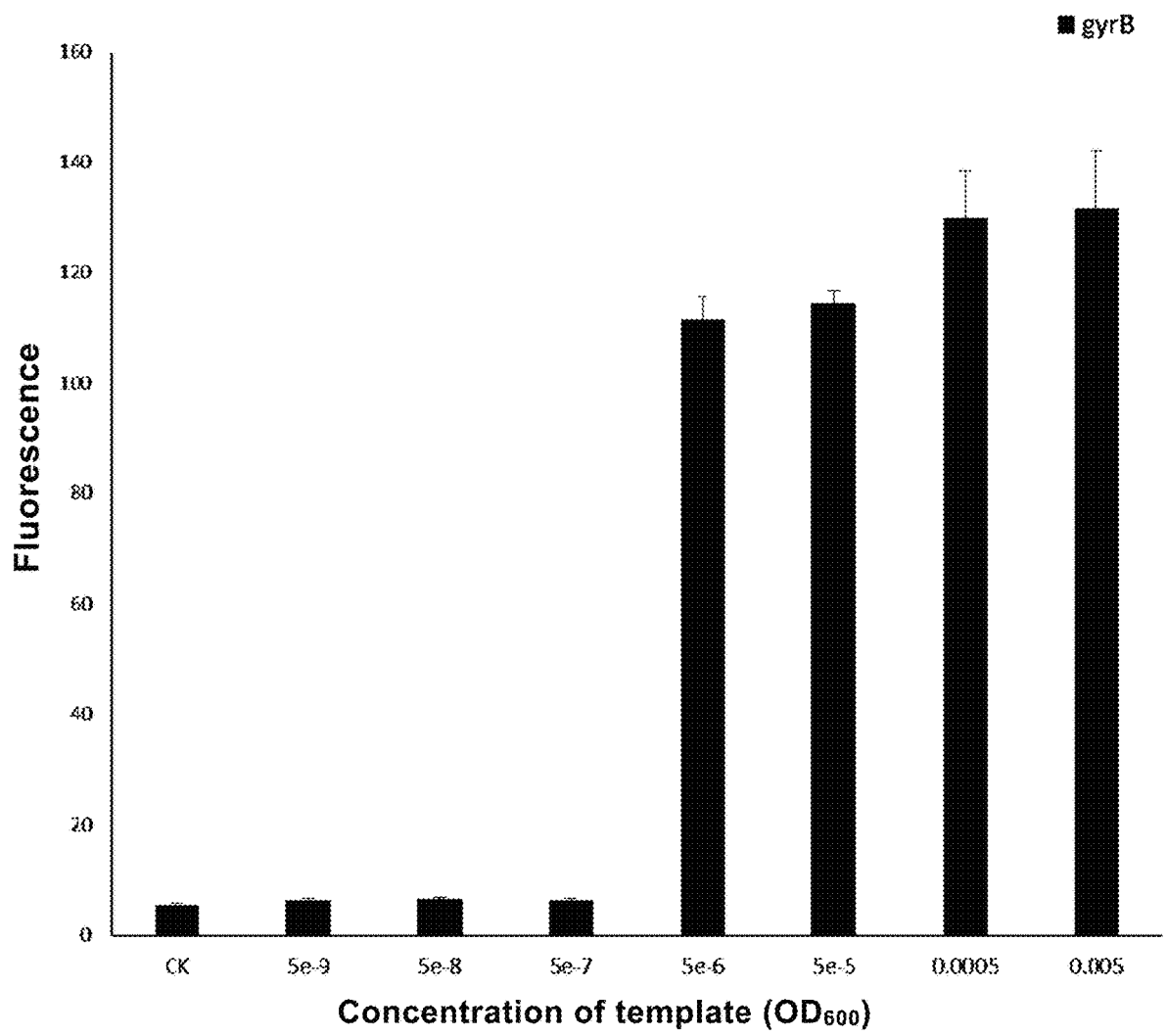
FIG. 13 shows the results of HOLMES v2.0 (LAMP combined with Cas12b) tests for the gyrB site of *E. coli*, to identify the presence of *E. coli* and the detection sensitivity through a gradient dilution test. (After coating test, the number of 0.005 OD of *E. coli* was about 7000)

As shown in FIG. 13, combining with LAMP amplification, the sensitivity of Cas12b (i.e., HOLMES v2.0 method) can reach the level of detecting very few *E. coli* (after coating test, $OD_{600}=5\times10^{-6}$ contained about 7 *E. coli*).

Example 5 Saliva Gender Test

In this example, the specific sry gene locus of the Y chromosome was selected as the test target, and the sex was identified using the saliva source sample through HOLMES v2.0.

1. Preparation of Guiding RNA (sgRNA)

Plasmid pUC18-sgRNA-DNMT1-3 was used as a template, and T7-crRNA-F was used as an upstream primer, and ZL-sry-crRNA3-R and ZLsgRNA-DNMT1-3-R were used as downstream primers. The two DNA templates required for in vitro transcription was amplified by PCR, respectively. Then DpnI was added into the PCR product (1 μl of DpnI (10 U/μl) per 50 μl of PCR system), incubated in 37° C. water bath for 30 min. The plasmid DNA template was digested, and gel and PCR product column recovery kit (Promega) was used to recover the PCR product. The recovered PCR product was used as a template, and sgRNA was synthesized using T7 High Yield Transcription Kit (Thermo). And the reaction was carried out overnight (12-16 h) at 37° C.

Then DNase I was added to the transcription system (2 μl of DNase I (5 U/μl) was added into per 50 μl of transcription system), incubated at 37° C. water bath for 30 min. DNA template was eliminated, and RNA purification and concentration kit was used to purify RNA. And then NanoDrop 2000C was used for quantify and the product was stored in a refrigerator at −80° C. for later use.

2. LAMP Amplification Reaction

Male and female saliva samples were used as templates, and LAMP amplification reaction was performed. The total volume of each reaction system was 25 μL. 1.6 μM of LAMP-sry-FIP and LAMP-sry-BIP, 0.2 μM of LAMP-sry-F3 and LAMP-sry-B3, and 0.4 μM of LAMP-sry-LoopF and LAMP-sry-LoopB were used as the primers. The kit used for LAMP reaction was WarmStart® LAMP Kit (NEB). The LAMP reaction program was 65° C. 30 min. After the LAMP was completed, the product was inactivated at 85° C. for 10 min, and then directly used in the Cas12b reaction.

3. Cas12b Reaction (1) sgRNA annealing: sgRNA was diluted to an appropriate concentration (5 μM), and annealed in a PCR machine. Annealing procedure: denatured at 75° C. for 5 min, then cooled down from 75° C. to 20° C., with a cooling rate of 1° C. per minute.

(2) Incubation of sgRNA with Cas12b: The annealed sgRNA was incubated with Cas12b at an equimolar concentration and placed at 30° C. for 20-30 min.

(3) Cas12b reaction: In a 20 μl reaction system, the mixture of sgRNA and Cas12b incubated in step (2) (the final concentration of both was 250 nM), 1 μl of the LAMP product, the fluorescence probe (HEX-N12-BHQ1, with a final concentration of 500 nM), and 2 μl of 10×NEB Buffer 3.1 and 0.5 μl of RNase inhibitor (40 U/μl) were added. After mixed, it was reacted at 48° C. for 30 min. After that, it was inactivated by being heated at 98° C. for 5 min.

4. Detection of the Bypass Single-Stranded DNA Cleavage Activity of Cas12b Using a Fluorescence Microplate Reader Method 20 μL of the inactivated reaction solution was added to a 96-well plate and detected with a microplate reader (excitation light 535 nm, emission light 556 nm).

Figure 14:
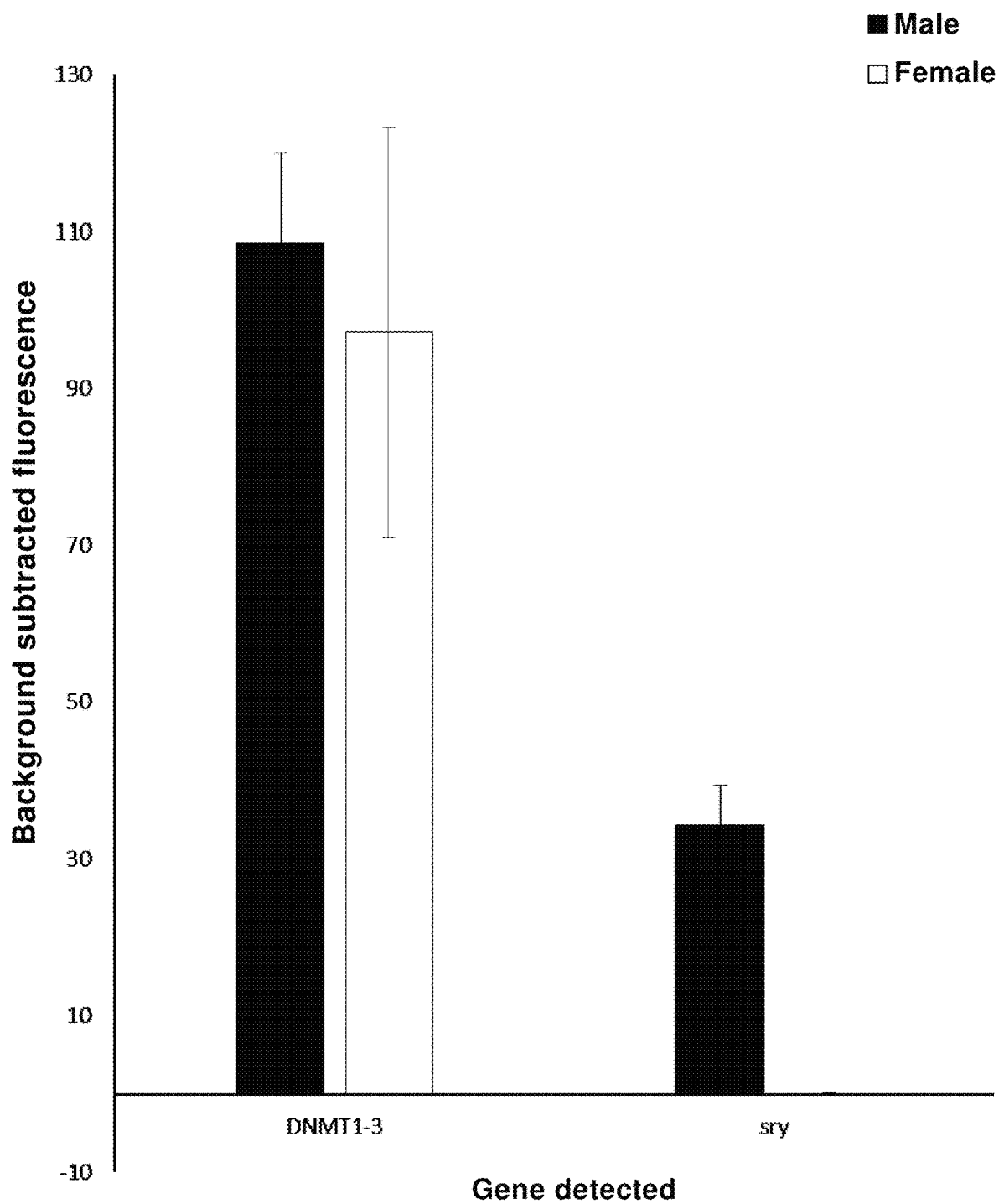
FIG. 14 shows the results of HOLMES v2.0 (LAMP combined with Cas12b) tests for the Y chromosome sry locus, using saliva samples to identify sex (DNMT1-3 locus is a gene locus on the chromosome, which was used as a positive control).

As shown in FIG. 14, combining with LAMP amplification, Cas12b (i.e., HOLMES v2.0 method) can efficiently perform human gender identification using saliva samples.

Example 6 Detection of Human SNP

In this example, human rs5082 locus was detected. Target DNA was prepared by asymmetric PCR or LAMP isothermal amplification method to identify the SNP type of saliva-derived samples.

1. Preparation of Guiding RNA (sgRNA)

Plasmid pUC18-sgRNA-DNMT1-3 was used as template, T7-crRNA-F was used as upstream primer, and oligonucleotides containing guide sequences complementary to rs5082 site with different lengths were used as downstream primers. And the DNA template required for in vitro transcription was amplified by PCR. Then DpnI was added into the PCR product (1 μl of DpnI (10 U/μl) per 50 μl of PCR system), incubated in 37° C. water bath for 30 min. The plasmid DNA template was digested, and gel and PCR product column recovery kit (Promega) was used to recover the PCR product. The recovered PCR product was used as a template, and truncated sgRNA was synthesized using T7 High Yield Transcription Kit (Thermo). And the reaction was carried out overnight (12-16 h) at 37° C. For the target DNA generated by asymmetric PCR, a truncated sgRNA with a guiding sequence of 16 nt was used in the Cas12b reaction. For the target DNA generated by LAMP amplification, a truncated sgRNA with a guiding sequence of 18 nt was used in the Cas12b reaction.

Then DNase I was added to the transcription system (2 μl of DNase I (5 U/μl) was added into per 50 μl of transcription system), incubated at 37° C. water bath for 30 min. Plasmid DNA template was eliminated, and RNA purification and concentration kit was used to purify RNA. And then NanoDrop 2000C was used for quantify and the product was stored in a refrigerator at −80° C. for later use.

2. Amplification Reaction (Asymmetric PCR or LAMP)

Asymmetric PCR amplification reaction: Human cell genome HEK293T was used as a template, and primers ASP-primer, ASP-rs5082-F, ASP-rs5082-R were used for asymmetric PCR amplification (while traditional PCR does not involve the ASP-primer), and KOD FX enzyme was used for the amplification reaction.

LAMP amplification reaction: Human cell genome HEK293T was used as a template to perform the LAMP amplification reaction. The total volume of each reaction system was 25 μL. 1.6 μM of LAMP-rs5082-FIP-10PAM (LAMP-rs5082-FIP as the control) and LAMP-rs5082-BIP, 0.2 µM of LAMP-rs5082-F3 and LAMP-rs5082-B3, and 0.4 µM of LAMP-rs5082-LoopF and LAMP-rs5082-LoopB were used as the primers. The kit used for LAMP reaction was WarmStart® LAMP Kit (NEB). The LAMP reaction program was 65° C. 30 min. After the LAMP was completed, the product was inactivated at 85° C. for 10 min, and then directly used in the Cas12b reaction. Because the sequence of primer LAMP-rs5082-FIP-10PAM was added with PAM sequence, the amplified DNA has PAM sequence.

3. Cas12b Reaction
   (1) sgRNA annealing: sgRNA was diluted to an appropriate concentration (5 µM), and annealed in a PCR machine. Annealing procedure: denatured at 75° C. for 5 min, then cooled down from 75° C. to 20° C., with a cooling rate of 1° C. per minute.
   (2) Incubation of sgRNA with Cas12b: The annealed sgRNA was incubated with Cas12b at an equimolar concentration and placed at 30° C. for 20-30 min.
   (3) Cas12b reaction: In a 20 µl reaction system, the mixture of sgRNA and Cas12b incubated in step (2) (the final concentration of both was 500 nM, and the concentration of Cas12b in the LAMP amplification test was 250 nM), 1 µl of target DNA or 1 µl of the LAMP product, the fluorescence probe (HEX-N12-BHQ1, with a final concentration of 500 nM), and 2 µl of 10×NEB Buffer 3.1 and 0.5 µl of RNase inhibitor (40 U/µl) were added. After mixed, it was reacted at 48° C. for 60 min. After that, it was inactivated by being heated at 98° C. for 5 min in a PCR instrument.

4. Detection of the Bypass Single-Stranded DNA Cleavage Activity of Cas12b Using a Fluorescence Microplate Reader Method 20 µL of the inactivated reaction solution was added to a 96-well plate and detected with a microplate reader (excitation light 535 nm, emission light 556 nm).

Figure 15:
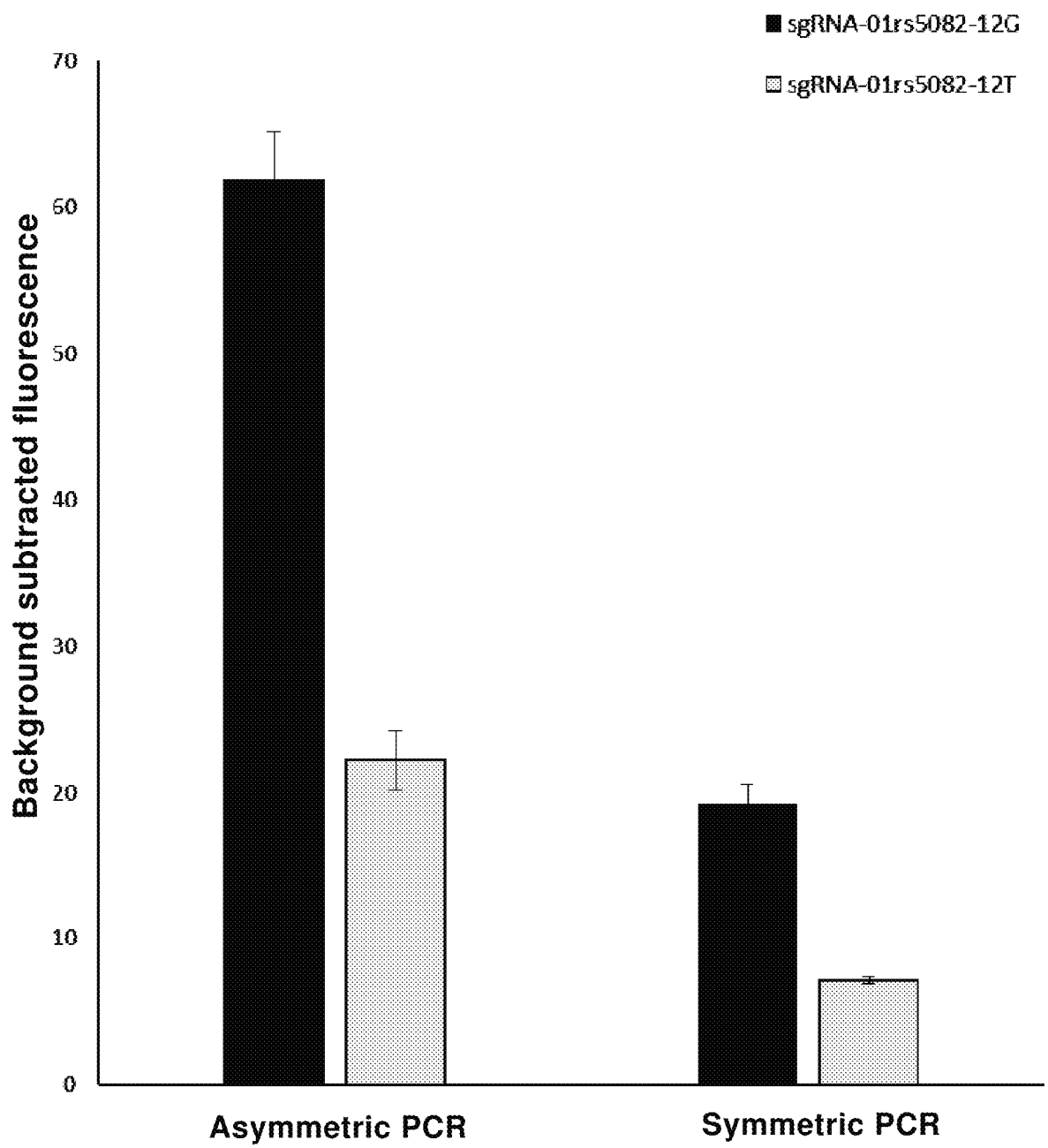
FIG. 15 shows the detection of the SNP site (rs5082) by asymmetric or symmetric PCR amplification combined with Cas12b. It can be seen that since there is no PAM sequence near the rs5082 site, the asymmetric PCR that produces single-stranded DNA can more clearly distinguish the SNP sites.

It can be seen from FIG. 15 that since there is no PAM sequence near the rs5082 site, the asymmetric PCR that produces single-stranded DNA can more clearly distinguish the SNP sites.

Figure 16:
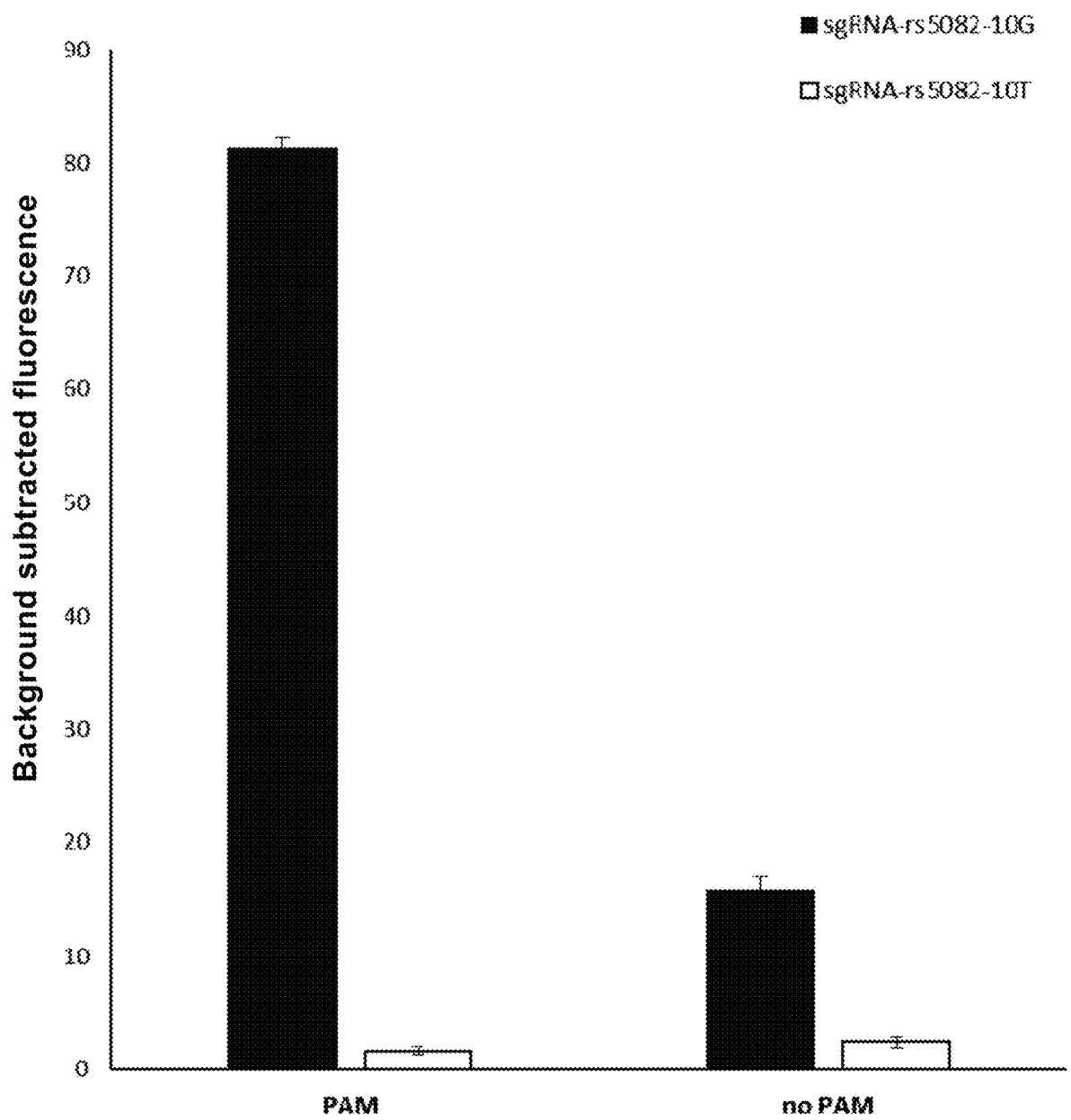
FIG. 16 shows the detection of the SNP site (rs5082) through LAMP amplification, combined with Cas12b, wherein primers were designed and PAM sequence was introduced. It can be seen that since there is no PAM sequence near the rs5082 site, the LAMP amplification method introduced with PAM (with PAM sequence in the primer) was better for distinguish SNP sites.

If combined with LAMP amplification, since there was no PAM sequence near the rs5082 site, the detection site needed to be introduced with the PAM sequence to better distinguish SNP sites (FIG. 16).

Example 7 Detection of RNA Virus

In this example, the RNA virus JEV (Japanese encephalitis virus) was selected, and HOLMES v2.0 was used to identify whether the sample was infected with the virus, and the sites selected for testing were E453 and NS170.

1. Preparation of Guiding RNA (sgRNA)

Plasmid pUC18-sgRNA-DNMT1-3 was used as template, T7-crRNA-F was used as upstream primer, and oligonucleotides containing guide sequences complementary to the corresponding targets were used as downstream primers. And the DNA template required for in vitro transcription was amplified by PCR. Then DpnI was added into the PCR product (1 µl of DpnI (10 U/µl) per 50 µl of PCR system), incubated in 37° C. water bath for 30 min. The plasmid DNA template was digested, and gel and PCR product column recovery kit (Promega) was used to recover the PCR product. The recovered PCR product was used as a template, and sgRNA was synthesized using T7 High Yield Transcription Kit (Thermo). And the reaction was carried out overnight (12-16 h) at 37° C.

Then DNase I was added to the transcription system (2 µl of DNase I (5 U/µl) was added into per 50 µl of transcription system), incubated at 37° C. water bath for 30 min. Plasmid DNA template was eliminated, and RNA purification and concentration kit was used to purify RNA. And then Nano-Drop 2000C was used for quantify and the product was stored in a refrigerator at −80° C. for later use.

2. LAMP Amplification Reaction

Cell fluid infected with JEV virus was used as a template, and LAMP amplification reaction was performed. The total volume of each reaction system was 25 µL. 1.6 µM of LAMP-E453-FIP and LAMP-E453-BIP, 0.2 µM of LAMP-E453-F3 and LAMP-E453-B3, and 0.4 µM of LAMP-E453-LoopF and LAMP-E453-LoopB (or 1.6 µM of LAMP-NS170-FIP and LAMP-NS170-BIP, 0.2 µM of LAMP-NS170-F3 and LAMP-NS170-B3, and 0.4 µM of LAMP-NS170-LoopF and LAMP-NS170-LoopB) were used as the primers. The kit used for LAMP reaction was WarmStart® LAMP Kit (NEB) or Bst 3.0 DNA polymerase (NEB). The LAMP reaction program was 65° C. 30 min. After the LAMP was completed, the product was inactivated at 85° C. for 10 min, and then directly used in the Cas12b reaction.

3. Cas12b Reaction
   (1) sgRNA annealing: sgRNA was diluted to an appropriate concentration (5 µM), and annealed in a PCR machine. Annealing procedure: denatured at 75° C. for 5 min, then cooled down from 75° C. to 20° C., with a cooling rate of 1° C. per minute.
   (2) Incubation of sgRNA with Cas12b: The annealed sgRNA was incubated with Cas12b at an equimolar concentration and placed at 30° C. for 20-30 min.
   (3) Cas12b reaction: In a 20 µl reaction system, the mixture of sgRNA and Cas12b incubated in step (2) (the final concentration of both was 250 nM), 1 µl of the LAMP product, the fluorescence probe (HEX-N12-BHQ1, with a final concentration of 500 nM), and 2 µl of 10×NEB Buffer 3.1 and 0.5 µl of RNase inhibitor (40 U/µl) were added. After mixed, it was reacted at 48° C. for 30 min. After that, it was inactivated by being heated at 98° C. for 5 min in a PCR machine.

4. Detection of the Bypass Single-Stranded DNA Cleavage Activity of Cas12b Using a Fluorescence Microplate Reader Method 20 µL of the inactivated reaction solution was added to a 96-well plate and detected with a microplate reader (excitation light 535 nm, emission light 556 nm).

As shown in FIG. 17, combining with LAMP amplification, Cas12b (i.e., HOLMES v2.0 method) can detect the presence of JEV virus very sensitively.

Example 8 Relative Quantitative Detection of Trace DNA (Real-Time HOLMES Method)

1. Preparation of Guiding RNA (sgRNA)

Plasmid pUC18-sgRNA-DNMT1-3 was used as template, T7-crRNA-F was used as upstream primer, and oligonucleotides containing guide sequences complementary to the targets were used as downstream primers. And the DNA template required for in vitro transcription was amplified by PCR. Then DpnI was added into the PCR product (1 µl of DpnI (10 U/µl) per 50 µl of PCR system), incubated in 37° C. water bath for 30 min. The plasmid DNA template was digested, and gel and PCR product column recovery kit (Promega) was used to recover the PCR product. The recovered PCR product was used as a template, and sgRNA was synthesized using T7 High Yield Transcription Kit (Thermo). And the reaction was carried out overnight (12-16 h) at 37° C.

Then DNase I was added to the transcription system (2 μl of DNase I (5 U/μl) was added into per 50 μl of transcription system), incubated at 37° C. water bath for 30 min. Plasmid DNA template was eliminated, and RNA purification and concentration kit was used to purify RNA. And then Nano-Drop 2000C was used for quantify and the product was stored in a refrigerator at −80° C. for later use.

2. One-Step LAMP Amplification-Fluorescence Detection Reaction (Using Real-Time PCR Instrument)

The DNMT1-3 plasmids of different dilution concentrations were used as templates to carry out the LAMP amplification reaction. The total volume of each reaction system was 20 μL. 1.6 μM of LAMP-DNM-FIP and LAMP-DNM-BIP, 0.2 μM of LAMP-DNM-F3 and LAMP-DNM-B3, and 0.4 μM of LAMP-DNM-LoopF and LAMP-DNM-LoopB were used as the primers. The kit used for LAMP reaction was WarmStart® LAMP Kit (NEB).

The mixture of sgRNA and Cas12b (the final concentration of both was 500 nM), the fluorescence probe (FAM-N12-Eclipse, with a final concentration of 500 nM), and 0.5 μl of RNase inhibitor (40 U/μl) were added. After mixing, real-time fluorescence detection was performed on a fluorometer, and the reaction condition was 55° C. for 120 min.

3. Result Analysis

FIG. 18 shows the real-time fluorescence measurement values of target DNA at different dilution concentrations.

The approximate straight trend line was obtained, using the time point when the fluorescence value reaches 600,000 as the y-axis and using the 1 g absolute value of the concentration as the x-axis.

The above results indicate that the method of the present invention can accurately quantify $10^{-1}$-$10^{-6}$ nM DNA within 45 minutes.

Example 9 Absolute Quantitative Detection of Trace DNA (Digital HOLMES Method)

In this example, the HOLMES method was combined with chip digital PCR to perform absolute quantitative detection at one reaction temperature.

1. Preparation of Guiding RNA (sgRNA)

Plasmid pUC18-sgRNA-DNMT1-3 was used as template, T7-crRNA-F was used as upstream primer, and oligonucleotides containing guide sequences complementary to rs5082 site with different lengths were used as downstream primers. And the DNA template required for in vitro transcription was amplified by PCR. Then DpnI was added to this PCR product (1 μl DpnI(10 U/μl) per 50 μl PCR system), incubated in 37° C. water bath for 30 minutes. The plasmid DNA template was digested, and gel and PCR product column recovery kit (Promega) was used to recover the PCR product. The recovered PCR product was used as a template, and sgRNA was synthesized using T7 High Yield Transcription Kit (Thermo). And the reaction was carried out overnight (12-16 h) at 37° C.

Then DNase I was added to the transcription system (2 μl of DNase I (5 U/μl) was added into per 50 μl of transcription system), incubated at 37° C. water bath for 30 min. Plasmid DNA template was eliminated, and RNA purification and concentration kit was used to purify RNA. And then Nano-Drop 2000C was used for quantify and the product was stored in a refrigerator at −80° C. for later use.

2. One-Step LAMP Amplification-Fluorescence Detection Reaction (Using Jnmedsys ddPCR Instrument)

The human 293T cell genome at different dilution concentrations were used as the template for absolute quantitative detection. The total volume of each reaction system was 15 μL. 1.6 μM of LAMP-rs5082-FIP-10PAM and LAMP-rs5082-BIP, 0.2 μM of LAMP-rs5082-F3 and LAMP-rs5082-B3, and 0.4 μM of LAMP-rs5082-LoopF and LAMP-rs5082-LoopB were used as the primers. The kit used for LAMP reaction was WarmStart® LAMP Kit (NEB). The mixture of sgRNA and Cas12b (the final concentration of both was 500 nM), the fluorescence probe (HEX-N12-BHQ1 and FAM-N12-Eclipse, both with a final concentration of 500 nM), 0.375 μl of RNase inhibitor (40 U/μl) and 0.75 μl of JN solution were added.

After mixing, the slide was used to deliver the sample to the chip (in the PCR tube) for system partitioning. Then the chip was transferred to the Sealing Enhancer instrument for processing.

Then, 235 ul of blocking solution was added, and reacted in a metal bath under the condition of 55° C. for 120 min. After 0, 60, 90, and 120 minutes, the chip was placed in the View Jig instrument to detect fluorescence.

3. Result Analysis

Figure 20:
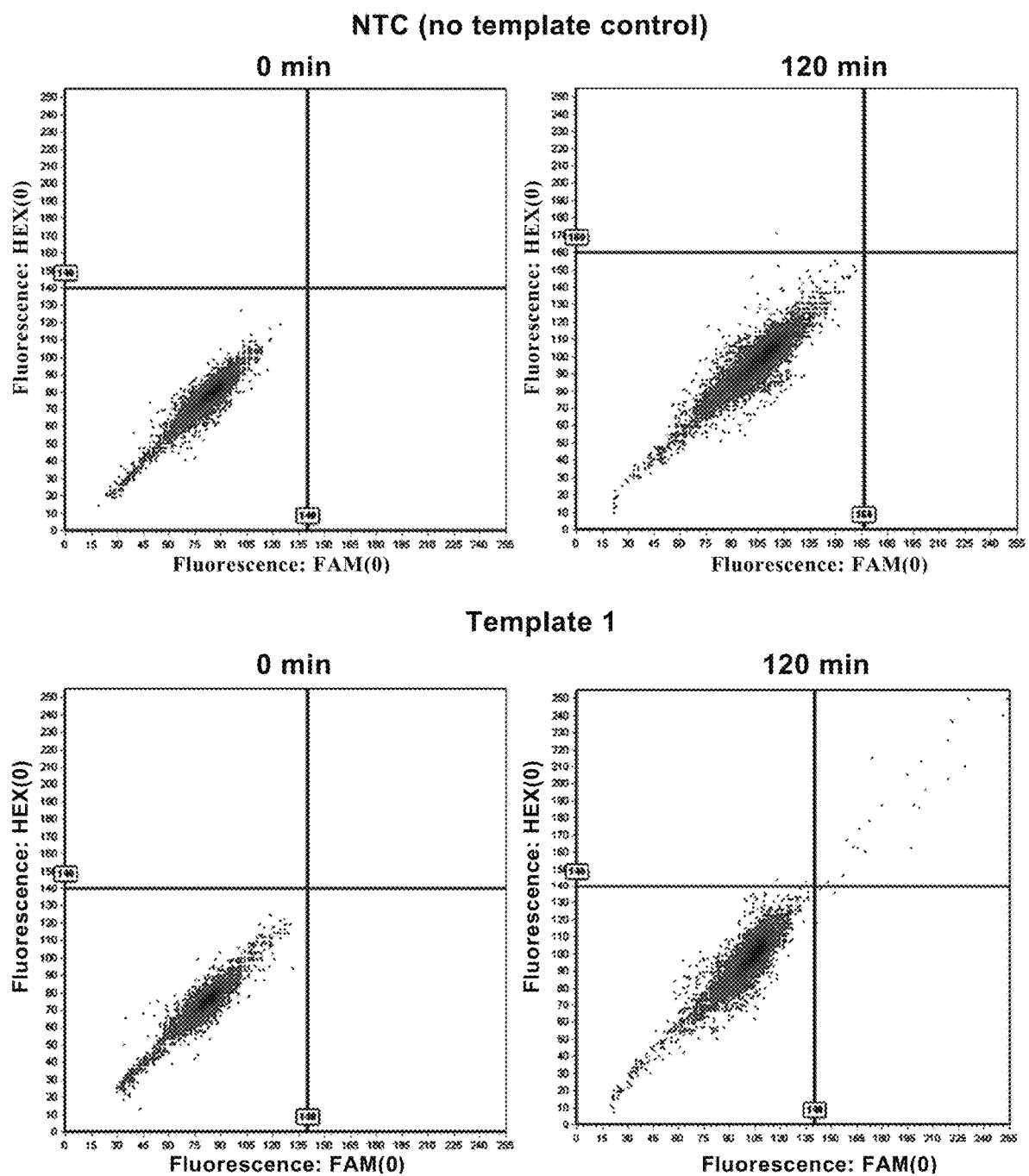
FIG. 20 shows the absolute quantitative detection of nucleic acid samples using digital HOLMES (LAMP combined with Cas12b and clarity chip) method.
Figure 20:
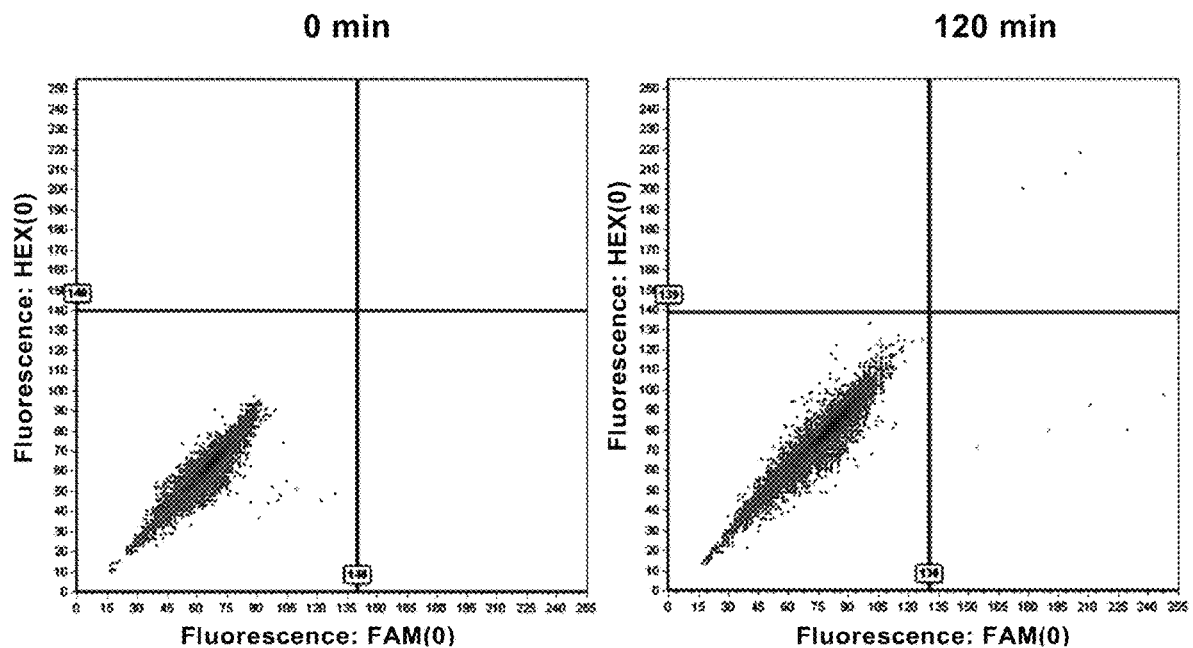

As shown in FIG. 20, after 120 minutes of reaction, by calculation, 51.75 copies were detected in template 1 and 6.3 copies were detected in the 10-fold diluted template 2. No copy was detected in the control without template.

The results show that the digital HOLMES method of the present invention can not only quantitatively detect, but also accurately detect a single copy of a template in a micro-detection system with extreme sensitivity, and greatly reduced time-consuming.

Example 10 Detection of Methylation Sites

In this example, through the NCBI search query, a promoter region (250 bp) of the collagen α2(I) gene (COL1A2), containing 13 CpG sites (M1-M13), was selected as the target gene detection sequence (NCBI accession number: AF004877.1). Collagen α2(I) gene (COL1A2) encodes collagen and is related to tumorigenesis.

In COL1A2(BSP)-C, CpG sites were all modified by methylation. After bisulfite conversion treatment (converting unmethylated C to uracil) and PCR amplification, the methylated C base in CpG was still C.

In COL1A2(BSP)-T, none of the CpG sites was modified by methylation. After bisulfite conversion treatment and PCR amplification, the C base in CpG became T.

Figure 21:
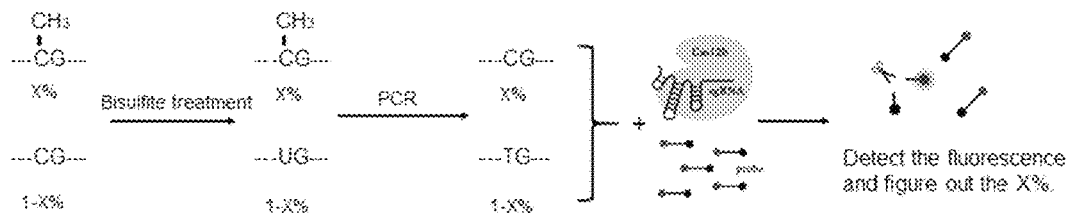
FIG. 21 is a schematic diagram of HOLMESv2 detecting target DNA methylation. After bisulfite conversion treatment and PCR amplification, the C base at the unmethylated CpG site would be converted to T. By designing an sgRNA guide sequence that exactly matches the methylated target site, the HOLMESv2 reaction (namely added with Cas12b, sgRNA and a single-stranded DNA probe labeled with a fluorescent group at one end and a quenching group at the other end) was used for detecting the content of methylation sites in the system. Similarly, it is also possible to design an sgRNA guide sequence that exactly matches the unmethylated target site, and use the HOLMESv2 reaction to detect the content of unmethylated sites in the system, and then the ratio of methylated sites can be calculated.

The principle of the methylation site detection method of the present invention is shown in FIG. 21.

Experimental Method:

1. The genomes of four cancer cell lines (293T, SW480, NCI-N87, and MCF-7) were extracted.
2. The genome was treated by bisulfite conversion. The promoter region of the COL1A2 gene containing the M3 site was selected, and the corresponding BSP primers (primer COL1A2(BSP)-F/R) were designed. The cell genome treated by bisulfite conversion was used as the template for PCR amplification, and the gel was recovered and purified to obtain the product, which was used as the target DNA for subsequent detection.
3. Preparation of target nucleic acid for standard curve
   (1) Primers (primer COL1A2-F/R) were used to amplify the gene fragment COL1A2 from SW480-gDNA, and it was assembled into the pClone007S T vector (TSINGKE, TSV-007S). Then the vector was transformed into DH10b. After cultured in LB medium with appropriate antibiotics at 37° C., the plasmid was extracted and sequenced, and finally the plasmid pClone007-COL1A2 was obtained.

(2) Plasmid pClone007-COL1A2 was treated with CpG methyltransferase (M.SssI) (M0226V, NEB), so that cytosine residues in all 5'-CG-3' sequences were methylated. And then the plasmids pClone007-COL1A2 and pClone007-COL1A2 treated with CpG methyltransferase were treated for bisulfite conversion, to convert unmethylated cytosine to uracil. The BSP primer pair (primer COL1A2(BSP)-F/R) was designed for PCR amplification, and the amplified fragments were recovered and purified by gel and assembled into pClone007S T vector to construct plasmids pClone007-COL1A2(BSP)-C and pClone007-COL1A2(BSP)-T, thus obtaining fragments COL1A2(BSP)-C(Target C) and COL1A2(BSP)-T(Target T).

4. Detection of Methylation

The four cancer cell lines gDNA (293T, SW480, NCI-N87, and MCF-7) were treated with EZ DNA methylation-direct™ kit (D5021, Zymo Research) for bisulfite conversion. And then BSP primer pair (primer COL1A2(BSP)-F/R) was used to amplify the COL1A2(BSP) (250 bp) gene fragments of the four cancer cell lines, and gel recovery and purification was performed.

Bisulfite Clone Sequencing Method

The above four COL1A2 (BSP) gene fragments were connected to the pClone007S T vector, and then transformed into DH10b. More than 10 positive monoclonal clones were picked from the plate and sent for sequencing analysis. The methylation rate calculation tool, QUantification tool for Methylation Analysis (QUMA), was used to calculate the degree of methylation of the 13 CpG sites in the COL1A2 gene.

Direct Bisulfite Sequencing

The above four COL1A2(BSP) gene fragments were analyzed by Sanger sequencing method, and the methylation rate was obtained by calculating the peak ratio C/(C+T) of 13 CpG sites in the COL1A2 gene.

Bisulfite NGS High-Throughput Sequencing Method

The above four COL1A2 (BSP) gene fragments were subjected to NGS high-throughput sequencing and NGS high-throughput sequencing and analysis (completed by Zhongke Purui Biotechnology Co., Ltd.), and the degree of methylation of the 13 CpG sites in the COL1A2 gene were analyzed.

Methylation Detection by HOLMESv2 System (1) Extraction of CRISPR-Cas12b Protein The codon-optimized AacCas12b full-length gene was synthesized by Shanghai Tolo Biotechnology Company Limited, and cloned into the vector pET28a. And the N-terminal His-tagged recombinant Cas12b protein was expressed and produced in E. coli BL21 (DE3). When $OD_{600}$ of the bacterial solution reached 0.6, 0.25 mM of isopropyl thiogalactoside (IPTG) was added to induce expression and the bacterial was culture at 16° C. for 14-18 h. And then the solution was centrifuged to harvest the bacteria. The bacterial solution was suspended in buffer A (50 mM Tris-HCl (pH 7.6), 150 mM NaCl, 20 mM imidazole, and 1/500 toluenesulfonyl fluoride (v/v)), and lysed by a high-pressure homogenizer (Avestin), and centrifuged at 15,000 rpm for 30 min. Ni column (GE Healthcare) was pre-equilibrated with buffer A, and the supernatant was transferred to Ni column. And then buffer B (50 mM Tris-HCl (pH 7.6), 200 mM NaCl and 30 mM imidazole) was used to elute the Ni column, and buffer B (wherein the imidazole concentration was adjusted to 300 mM) to elute the recombinant protein. The eluted fractions containing AacCas12b protein were collected by ultrafiltration and concentrated to about 5 mL. Then it was loaded to the column HiLoad 16/600 Superdex 200 pg column (GE Healthcare) equilibrated with buffer C (40 mM Tris-HCl (pH 7.6), 200 mM NaCl, 2 mM DTT and 5% glycerol (v/v))), and the eluted fractions containing AacCas12b protein was collected, concentrated to 4 mg/mL, added with 50% glycerol and stored at −20° C.

(2) Preparation of sgRNA

Plasmid pUC18-sgRNA-DNMT1-3 was used as a template, and T7-sgRNA-F was used as an upstream primer, and downstream primers specific for targets were designed. The DNA template required for in vitro transcription was amplified by PCR. Then DpnI was added into the PCR product (1 μl of DpnI per 50 μl of PCR system), incubated in 37° C. water bath for 30 min. The plasmid DNA template was digested, and gel and PCR product column recovery kit (Promega) was used to recover the PCR product. The recovered PCR product was used as a template, and sgRNA was synthesized using T7 High Yield Transcription Kit (Thermo). And the reaction was carried out overnight (12-16 h) at 37° C. Finally, DNase I was added to the transcription system (2 μl of DNase I was added into per 50 μl of transcription system), incubated at 37° C. water bath for 30 min. DNA template was eliminated, and RNA purification and concentration kit (Zymo Research) was used to purify RNA. The obtained sgRNA was named sgRNA-DNMT1-3 The product was quantified with NanoDrop 2000C, and stored in −80° C. refrigerator for later use.

(3) Screening of sgRNA

For COL1A2, a variety of sgRNA were designed wherein the guiding sequences of different lengths matched to the upstream and downstream of each CpG site, and the CpG sites corresponded to different positions of the gene. The sgRNA (with a final concentration of 10 μM) was annealed on a PCR instrument. The annealing procedure was: 75° C. for 5 min; and then, the temperature was cooled down with a cooling rate of 1° C. per 1 min, until 20° C. After annealing, sgRNA and AacCas12b protein (with a final concentration of 5 μM) were mixed in equal volume and incubated at 30° C. for 15-20 min. Finally, a 20 μL Cas12b reaction system was prepared (operation on ice):

| | |
|---|---|
| Cas12b | 250 nM |
| SgRNA | 500 nM |
| Target DNA (COL1A2(BSP)-C/T) | 100 nM |
| HEX-N12-BHQ1 (Fluorescence labeling) | 500 nM |
| 10 × NEB Buffer 3.1 | 2 μL |
| RRI (RNase inhibitor) | 0.5 μL |

Rnase-free $H_2O$ was added up to a totle volume of 20 μL.

Reaction was carried out in 48° C. water bath for 1 h, and 20 μL of the system was transformed into 96-well plate. The excitation light wavelength was set as 535 nm and emission wavelength was set as 556 nm on the microplate reader, to measure the fluorescence value. The sgRNA, used in the group of reactions wherein target DNA (COL1A2(BSP)-C/T) had the largest difference in fluorescence value, was screened out, which was the most suitable sgRNA.

(4) Methylation Detection Based on HOLMESv2 System

The fragments COL1A2(BSP)-C and COL1A2(BSP)-T were mixed well according to the proportion of COL1A2(BSP)-C as 0%, 10%, 30%, and 50%, respectively, as the target DNA of the methylation detection standard curve. The sample fragments COL1A2 (BSP) after treatment with bisulfite from the four cancer cell lines (293T, SW480, NCI-N87, and MCF-7) were mixed with the fragment COL1A2 (BSP)-T at an equimolar concentration, respectively, and the mixtures were then used as the target DNA to detect the methylation ratio of real samples. Then the methylation standard curve of the COL1A2 promoter region M3 site and the methylation ratio of M3 site in the four cancer cell lines (293T, SW480, NCI-N87, MCF-7) were detected respectively, using sgRNA-COL1A2m3-C12-17 in the HOLMESv2 system.

The sgRNA (with a final concentration of 10 μM) was annealed on a PCR instrument. The annealing procedure was: 75° C. for 5 min; and then, the temperature was cooled down with a cooling rate of 1° C. per 1 min, until 20° C. After annealing, sgRNA and AacCas12b protein (with a final concentration of 5 μM) were mixed in equal volume and incubated at 30° C. for 15-20 min. Finally, a 20 μL Cas12b reaction system was prepared (operation on ice):

| | |
|---|---|
| Cas12b | 250 nM |
| sgRNA | 500 nM |
| Target DNA (M3) | 5 nM |
| FAM-N12-Eclipse (Fluorescent label) | 500 nM |
| Sheared salmon sperm DNA | 500 ng |
| 10 × NEB Buffer 3.1. | 2 μL |
| RRI (RNase inhibitor) | 0.25 μL |

Rnase-free H$_2$O was added up to a totle volume of 20 μL.

20 μL of the system was transferred into a 96-well plate, which was then put into a real-time PCR instrument. The program was set to react at 48° C. for 1 h, and the fluorescence value was measured every 2 min.

The methylation standard curve at the M3 site took the fluorescence value at 30 min and 10 min as the ordinate Y, and took the proportion of COL1A2(BSP)-C 0%, 10%, 30%, and 50% as the abscissa X. The equation model was: Y=aX+b. The concentration of COL1A2 (BSP) in the four cancer cell lines was ½ of the target DNA in the standard curve. Therefore, the methylation ratio calculation model was: $X_{unknown}=2(Y_{unknown}-b)/a$.

Experimental Results:
1. Detection Mode Diagram

After the genes containing methylated CpG sites were subjected to bisulfite conversion treatment, all non-methylated sites CG in the genes were converted to UG, and all methylated sites CG remained unchanged. The transformed gene was used as the target DNA to form a ternary complex with AacCas12b protein and sgRNA. In a single-stranded DNA probe system with a fluorescent group and a quencher group (i.e., HOLMESv2 system), the reaction was constant at 48° C. for a certain period, and the fluorescence value was detected. If the detection site is methylated, the DNA probe emits light and the fluorescence value is high. If the detection site is not methylated, the DNA probe does not emit light, and the fluorescence value is very low or zero.

2. Screening of sgRNA

Figure 22:
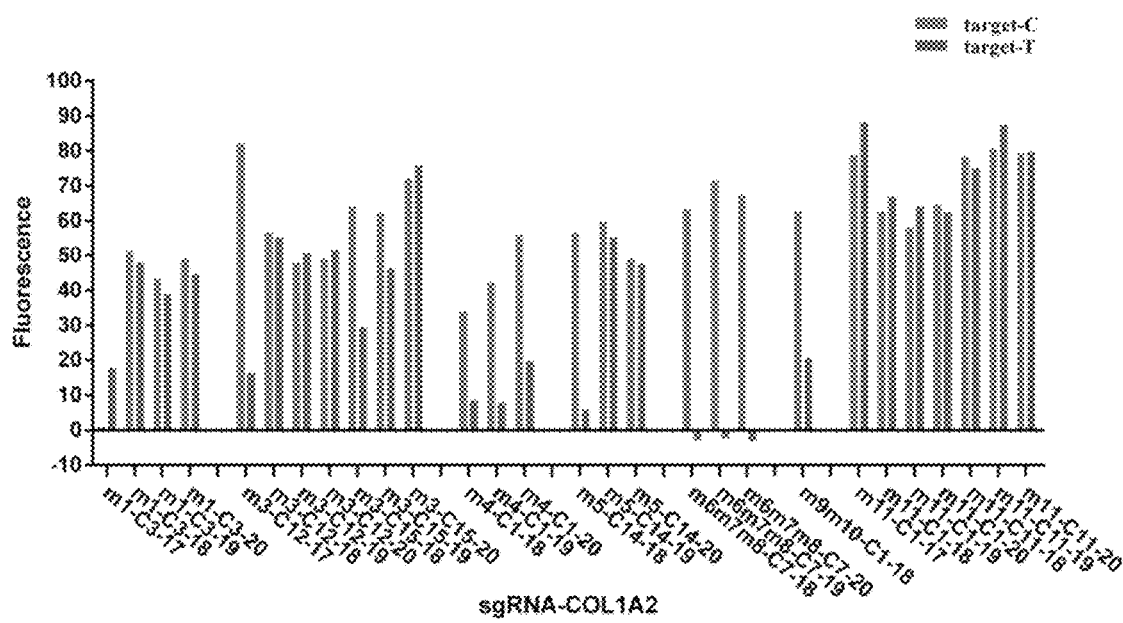
FIG. 22 shows the experimental results of detecting target DNA methylation using sgRNAs with different sites and different lengths. Target-C, means the test result when the position is C (representing methylation); while target-T means the test result when the position is T (representing the base before the bisulfite conversion treatment is not methylated). If an sgRNA sequence has a high signal value when targeting target-C and a low signal value when targeting target-T, the sgRNA sequence can be used for distinguishing whether the site has methylation modification.
Figure 23:
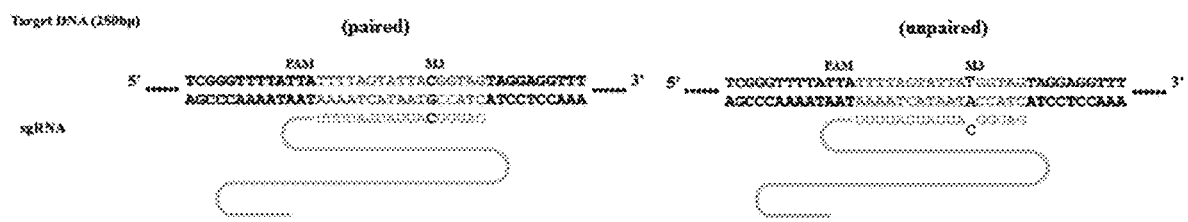
FIG. 23 shows a schematic diagram of target DNA methylation detection using sgRNA at m3-C12-17 of SEQ ID NO: 127. The left picture shows that the sgRNA sequence was completely matched with the target sequence; while the right picture shows that after the bisulfite conversion treatment and PCR amplification of the unmethylated site, the M3 site became T, causing the sgRNA sequence fail to match the target sequence.

As shown in FIG. 22, by comparing the fluorescence values of each sgRNA and two targets (target-C and target-T represent COL1A2 fragments after bisulfite treatment with a methylation degree in all CpG sites of 100% and 0%, respectively) in the HOLMESv2-Cas12b reaction system, the most suitable sgRNA can be selected. Wherein, the fluorescence values of 9 sgRNAs, m3-C12-17, m4-C1-18, m4-C1-19, m4-C1-20, m5-C14-18, m6m7m8-C7-18, m6m7m8-19, m6m7m8-20, and m9m10-C1-18, had obvious differences in the two targets (target-C, target-T), all of which can be used for methylation detection. In this study, a single point sgRNA (m3-C12-17) was selected for the subsequent methylation detection. The sgRNA was shown in FIG. 23.

3. Quantitative Detection of Methylation at M3 CpG Site (COL1A2)

Figure 25:
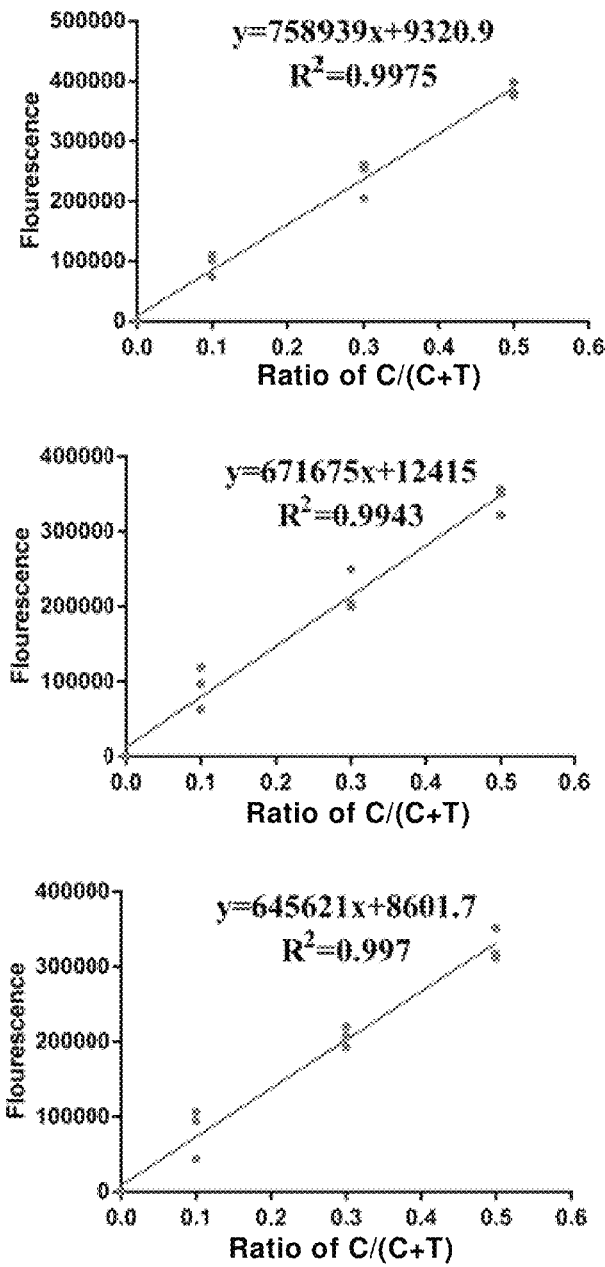
FIG. 25 shows a standard curve of the methylation level of M3 CpG site (COL1A2). A standard curve diagram was made according to the result of the standard curve test in FIG. 5.

The fragments COL1A2 (BSP)-C and COL1A2 (BSP)-T were mixed according to a ratio of COL1A2 (BSP)-C content of 0%, 10%, 30%, 50%, and sgRNA-COL1A2m3-C12-17 used to detect the fluorescence value of the reaction at 30 min in the HOLMESv2 system. After data analysis, the fluorescence value of 0% was used as a zero point for normalization, and the quantitative standard curve of M3 CpG site (COL1A2) methylation was drawn. The standard curve was drawn correspondingly for each test. The inventors tested for three times with three repetitions each time. The equations of the standard curves were: y=758939x+9320.9 ($R^2$=0.9975); y=671675x+12415 ($R^2$=0.9943); and y=645621x+8601.7 ($R^2$=0.997), respectively. The linear correlation of the three standard curves was very good, wherein $R^2$ reached 0.99 or more. Therefore, the fluorescent value of this gene locus in real samples can be detected by HOLMESv2, to calculate the corresponding degree of methylation (FIG. 25).

Figure 24:
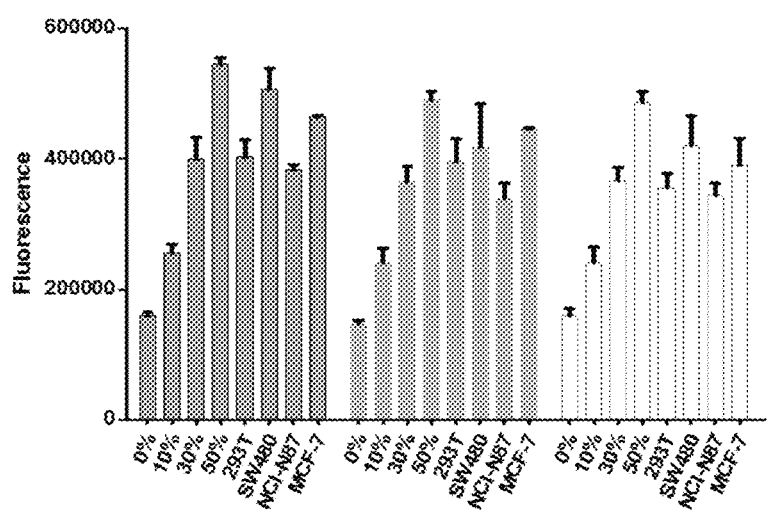

COL1A2 showed different levels of methylation in different cancers. In order to verify the practicability of HOLMESv2-Cas12b methylation detection method, sgRNA-COL1A2m3-C12-17 was used to detect the fluorescent values of the M3 CpG site (COL1A2) in the four kinds of cancer cells (293T, SW480, NCI-N87, and MCF-7) after 30 min reaction, in the HOLMESv2 system (FIG. 24). Wherein, the concentration of the target gene in cancer cells detected was ½ of that of the standard curve. Their degrees of methylation were calculated according to the above standard curve equations, respectively: 63.3%, 81.3%, 54.8% and 77.1%.

Figure 26:
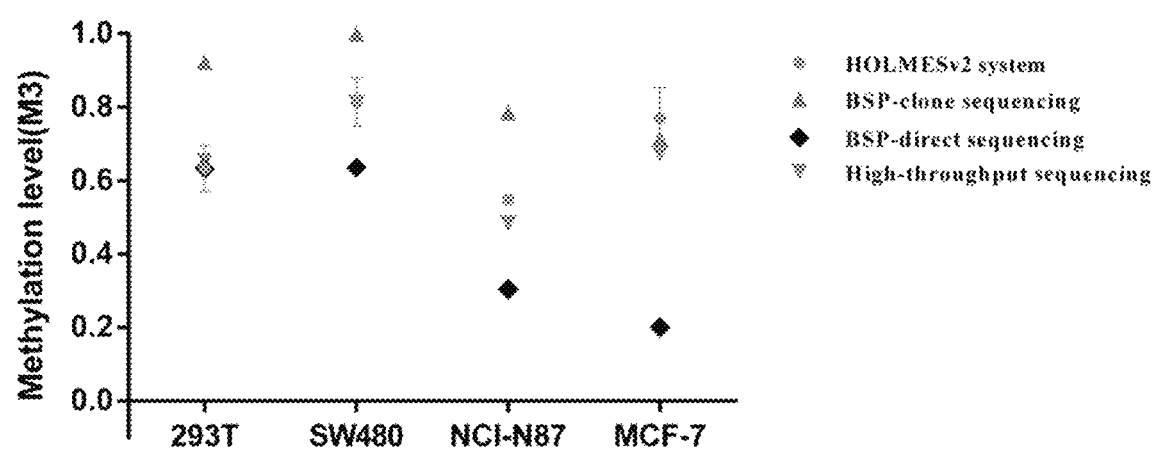
FIG. 26 shows the methylation rate test results of the M3 CpG site (COL1A2) in four cell lines (293T, SW480, NCI-N87, and MCF-7). As can be seen from the figure, the test result of the HOLMESv2 system was the closest to the NGS sequencing result (High-throughput sequencing).

In addition, at the same time, the currently widely used methylation detection method was used to detect the methylation levels of the COL1A2 gene in the above four cancer cells, and compared with the method of the present invention to verify the effectiveness and feasibility of the HOLMESv2-Cas12b methylation detection method (FIG. 26).

The bisulfite NGS high-throughput sequencing method can be used to quantitatively detect methylation. The methylation rates of the M3 CpG site (COL1A2) in four cancer cells (293T, SW480, NCI-N87, and MCF-7) were: 65.26%, 81.06%, 48.27%, and 67.3%, which was consistent with the HOLMESv2-Cas12b detection results.

The bisulfite direct sequencing method and bisulfite clone sequencing method can only be used to semi-quantitatively detect methylation at present. The methylation detection results of the M3 CpG site (COL1A2) in the above four cancer cells (293T, SW480, NCI-N87, and MCF-7) by these two methods were 63.2%, 63.6%, 30.4%, 20%, and 92.3% (12/13), 100% (15/15), 78.6% (11/14), 71.4% (10/14). Compared with the results of bisulfite NGS high-throughput sequencing method, the difference was large, wherein the former was low and the latter was high.

The above results indicate that the quantitative results of the HOLMESv2-Cas12b detection method of the present invention are very accurate, fast and simple.

Example 11 Detection of Alternatively Spliced RNA and Circular RNA

Pre-mRNA alternative splicing is a key link in post-transcriptional regulation of high eukaryotes, and plays an important role in human diseases such as tumor progression. Some pre-mRNA will be processed to form circular RNA.

Figure 27:
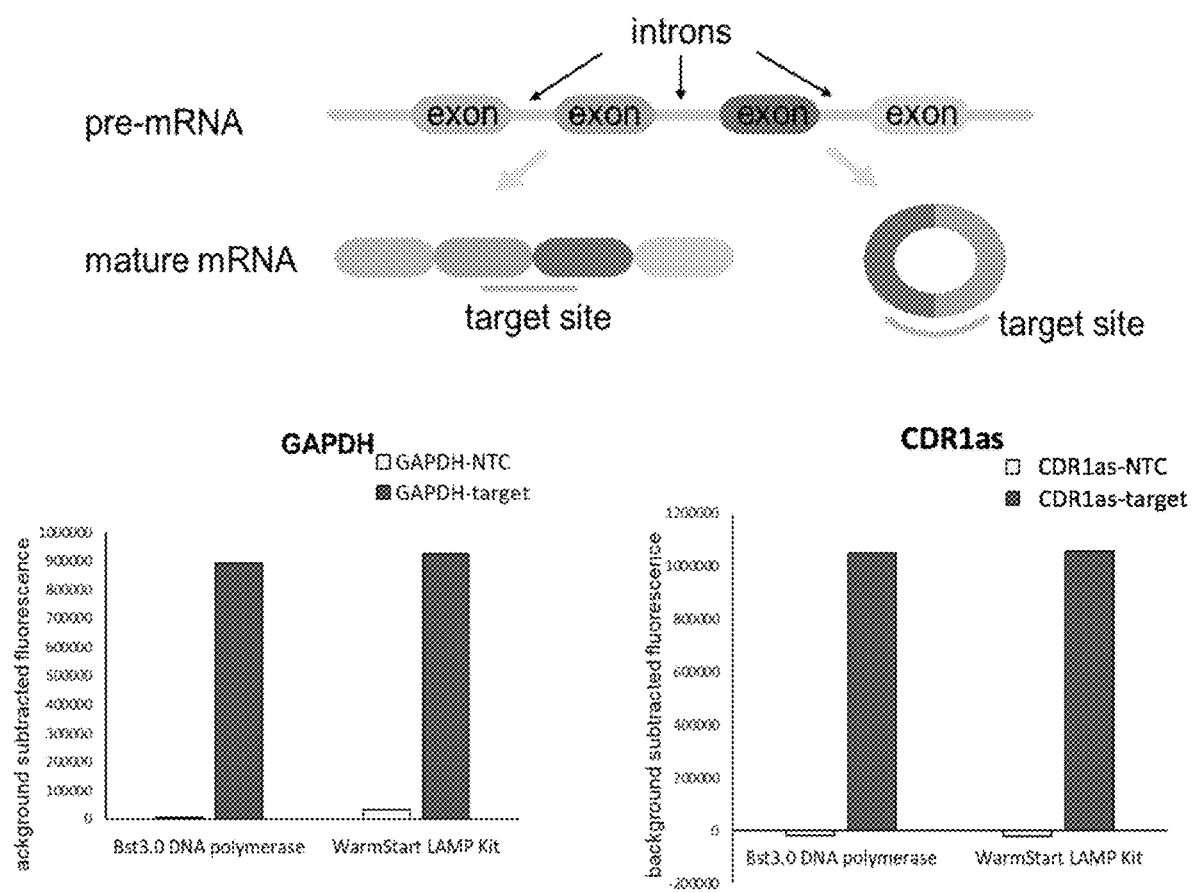
FIG. 27 shows the detection results of circular RNA using HOLMESv2 technology. Upper figure is a schematic diagram showing RNA detection by HOLMESv2 and the target site selection. Bottom left figure is a diagram showing the detection of target GAPDH by HOLMESv2. Bottom right figure is a diagram showing the detection of target CDR1as by HOLMESv2. Target site means target site. NTC is the experimental control group, wherein the sample was sterile water. Target is the experimental group, wherein the sample was an RNA sample. The fluorescence values in the lower left and lower right graphs are fluorescence values after the experimental background fluorescence deducted. Both the NTC and target reaction groups were amplified by the LAMP reaction, and the amplified products were used for the Cas12b reaction test; and the background fluorescence was the fluorescence value of the Cas12b reaction system tested by addingsterile water directly.

In this example, HOLMESv2 was used to detect mRNA splicing, specifically targeting the splicing site to detect, combined with RT-LAMP amplification, in order to detect the mature spliced mRNA of the GAPDH gene (FIG. 27). In addition, a similar strategy was adopted in the design of crRNA, and the circular RNA of Cdr1as in HEK293T was successfully detected in this example (FIG. 27).

1. Preparation of Guiding RNA (sgRNA)

Plasmid pUC18-sgRNA-DNMT1-3 was used as template, T7-sgRNA-F was used as upstream primer, and oligonucleotides containing guide sequences complementary to related targets were used as downstream primers (see Table 2). And the DNA template required for in vitro transcription was amplified by PCR. Then DpnI was added into the PCR product (1 μL of DpnI (10 U/μL) per 50 μL of PCR system), incubated in 37° C. water bath for 30 min. The plasmid DNA template was digested, and gel and PCR product column recovery kit (Promega) was used to recover the PCR product. The recovered PCR product was used as a template, and sgRNA was synthesized using T7 High Yield Transcription Kit (Thermo). And the reaction was carried out overnight (12-16 h) at 37° C.

Then DNase I was added to the transcription system (2 μL of DNase I (5 U/μL) was added into per 50 μL of transcription system), incubated at 37° C. water bath for 30 min. Plasmid DNA template was eliminated, and RNA purification and concentration kit was used to purify RNA. And then NanoDrop 2000C was used for quantify and the product was stored in a refrigerator at −80° C. for later use.

2. LAMP Amplification Reaction

The 293T cell genome was used for LAMP amplification reaction. The total volume of each reaction system was 25 μL. 1.6 μM of LAMP-FIP and LAMP-BIP, 0.2 μM of LAMP-F3 and LAMP-B3, and 0.4 μM of LAMP-LoopF and LAMP-LoopB were used as the primers. The kit used for LAMP reaction was WarmStart® LAMP Kit (NEB) or Bst 3.0 DNA polymerase (NEB). The LAMP reaction program was 65° C. 30 min. After the LAMP was completed, the product was inactivated at 85° C. for 10 min, and then directly used in the Cas12b reaction.

3. Cas12b Reaction (1) sgRNA annealing: sgRNA was diluted to an appropriate concentration (5 μM), and annealed in a PCR machine. Annealing procedure: denatured at 75° C. for 5 min, then cooled down from 75° C. to 20° C., with a cooling rate of 1° C. per minute.

(2) Incubation of sgRNA with Cas12b: The annealed sgRNA was incubated with Cas12b at an equimolar concentration and placed at 30° C. for 20-30 min.

(3) Cas12b reaction: In a 20 μL reaction system, the mixture of sgRNA and Cas12b incubated in step (2) (the final concentration of both was 250 nM), 1 μL of the LAMP product, the fluorescence probe (HEX-N12-BHQ1, with a final concentration of 500 nM), and 2 μL of 10×NEB Buffer 3.1 and 0.5 μL of RNase inhibitor (40 U/μL) were added.

After mixed, it was reacted at 48° C. for 30 min. After that, it was inactivated by being heated at 98° C. for 5 min in a PCR instrument.

4. Detection of the Bypass Single-Stranded DNA Cleavage Activity of Cas12b Using a Fluorescence Microplate Reader Method 20 μL of the inactivated reaction solution was added to a 96-well plate and detected with a microplate reader (excitation light 535 nm, emission light 556 nm). As shown in FIG. 27, it can be seen that after LAMP amplification, Cas12b (i.e., HOLMES v2.0 method) can detect and identify whether the RNA met the expected RNA splicing situation or whether it was circular RNA.

TABLE 1

Oligonucleotides as substrates

| name | Sequence (5'-3') | SEQ ID No.: |
|---|---|---|
| target-T1-F | tttctgtttgttatcgcaactttctactgaattcaagctttactctagaaagaggagaaaggatcc | 1 |
| target-T1-R | ggatcctttctcctctttctagagtaaagcttgaattcagtagaaagttgcgataacaaacagaaa | 2 |
| target-T1-FAM-5'-R | fam-ggatcctttctcctctttctagagtaaagcttgaattcagtagaaagttgcgataacaaacagaaa | 3 |
| target-T1-R-FAM | ggatcctttctcctctttctagagtaaagcttgaattcagtagaaagttgcgataacaaacagaaa-fam | 4 |
| DNMT1-3(TTC PAM)-F | aatgttccctgatggtccatgtctgttactcgcctgtcaagtggcgtgac | 5 |
| DNMT1-3(TTC PAM)-R | gtcacgccacttgacaggcgagtaacagacatggaccatcagggaacatt | 6 |
| DNMT1-3(AAC PAM)-F | aatgaaccctgatggtccatgtctgttactcgcctgtcaagtggcgtgac | 7 |
| DNMT1-3(AAC PAM)-R | gtcacgccacttgacaggcgagtaacagacatggaccatcagggttcatt | 8 |
| DNMT1-3(ATC PAM)-F | aatgatccctgatggtccatgtctgttactcgcctgtcaagtggcgtgac | 9 |
| DNMT1-3(ATC PAM)-R | gtcacgccacttgacaggcgagtaacagacatggaccatcagggatcatt | 10 |
| DNMT1-3(TAC PAM)-F | aatgtaccctgatggtccatgtctgttactcgcctgtcaagtggcgtgac | 11 |
| DNMT1-3(TAC PAM)-R | gtcacgccacttgacaggcgagtaacagacatggaccatcagggtacatt | 12 |
| DNMT1-3(GGC PAM)-R | gtcacgccacttgacaggcgagtaacagacatggaccatcagggcccatt | 13 |
| DNMT1-3(CCC PAM)-R | gtcacgccacttgacaggcgagtaacagacatggaccatcaggggggcatt | 14 |

TABLE 1-continued

Oligonucleotides as substrates

| name | Sequence (5'-3') | SEQ ID No.: |
|---|---|---|
| DNMT1-3-C1G-F | aatgttcgctgatggtccatgtctgttactcgcctgtcaagtggcgtgac | 15 |
| DNMT1-3-C1G-R | gtcacgccacttgacaggcgagtaacagacatggaccatcagcgaacatt | 16 |
| DNMT1-3-C2G-F | aatgttccgtgatggtccatgtctgttactcgcctgtcaagtggcgtgac | 17 |
| DNMT1-3-C2G-R | gtcacgccacttgacaggcgagtaacagacatggaccatcacggaacatt | 18 |
| DNMT1-3-T3A-F | aatgttcccagatggtccatgtctgttactcgcctgtcaagtggcgtgac | 19 |
| DNMT1-3-T3A-R | gtcacgccacttgacaggcgagtaacagacatggaccatctgggaacatt | 20 |
| DNMT1-3-G4C-F | aatgttccctcatggtccatgtctgttactcgcctgtcaagtggcgtgac | 21 |
| DNMT1-3-G4C-R | gtcacgccacttgacaggcgagtaacagacatggaccatgagggaacatt | 22 |
| DNMT1-3-A5T-F | aatgttccctgttggtccatgtctgttactcgcctgtcaagtggcgtgac | 23 |
| DNMT1-3-A5T-R | gtcacgccacttgacaggcgagtaacagacatggaccaacagggaacatt | 24 |
| DNMT1-3-T6A-F | aatgttccctgaaggtccatgtctgttactcgcctgtcaagtggcgtgac | 25 |
| DNMT1-3-T6A-R | gtcacgccacttgacaggcgagtaacagacatggaccttcagggaacatt | 26 |
| DNMT1-3-G7C-F | aatgttccctgatcgtccatgtctgttactcgcctgtcaagtggcgtgac | 27 |
| DNMT1-3-G7C-R | gtcacgccacttgacaggcgagtaacagacatggacgatcagggaacatt | 28 |
| DNMT1-3-G8C-F | aatgttccctgatgctccatgtctgttactcgcctgtcaagtggcgtgac | 29 |
| DNMT1-3-G8C-R | gtcacgccacttgacaggcgagtaacagacatggagcatcagggaacatt | 30 |
| DNMT1-3-T9A-F | aatgttccctgatggaccatgtctgttactcgcctgtcaagtggcgtgac | 31 |
| DNMT1-3-T9A-R | gtcacgccacttgacaggcgagtaacagacatggtccatcagggaacatt | 32 |
| DNMT1-3-C10G-F | aatgttccctgatggtgcatgtctgttactcgcctgtcaagtggcgtgac | 33 |
| DNMT1-3-C10G-R | gtcacgccacttgacaggcgagtaacagacatgcaccatcagggaacatt | 34 |
| DNMT1-3-C11G-F | aatgttccctgatggtcgatgtctgttactcgcctgtcaagtggcgtgac | 35 |
| DNMT1-3-C11G-R | gtcacgccacttgacaggcgagtaacagacatcgaccatcagggaacatt | 36 |
| DNMT1-3-A12T-F | aatgttccctgatggtccttgtctgttactcgcctgtcaagtggcgtgac | 37 |
| DNMT1-3-A12T-R | gtcacgccacttgacaggcgagtaacagacaaggaccatcagggaacatt | 38 |
| DNMT1-3-T13A-F | aatgttccctgatggtccaagtctgttactcgcctgtcaagtggcgtgac | 39 |
| DNMT1-3-T13A-R | gtcacgccacttgacaggcgagtaacagacttggaccatcagggaacatt | 40 |
| DNMT1-3-G14C-F | aatgttccctgatggtccatctctgttactcgcctgtcaagtggcgtgac | 41 |
| DNMT1-3-G14C-R | gtcacgccacttgacaggcgagtaacagagatggaccatcagggaacatt | 42 |
| DNMT1-3-T15A-F | aatgttccctgatggtccatgactgttactcgcctgtcaagtggcgtgac | 43 |
| DNMT1-3-T15A-R | gtcacgccacttgacaggcgagtaacagtcatggaccatcagggaacatt | 44 |
| DNMT1-3-C16G-F | aatgttccctgatggtccatgtgtgttactcgcctgtcaagtggcgtgac | 45 |
| DNMT1-3-C16G-R | gtcacgccacttgacaggcgagtaacacacatggaccatcagggaacatt | 46 |
| DNMT1-3-T17A-F | aatgttccctgatggtccatgtcagttactcgcctgtcaagtggcgtgac | 47 |
| DNMT1-3-T17A-R | gtcacgccacttgacaggcgagtaactgacatggaccatcagggaacatt | 48 |
| target-01-rs-R | agacttagatctgagccctccctcttcccagcacaggcaggggtagaagc | 49 |
| target-01-rs-12T-R | agacttagatctgagccctccctcttcccagaacaggcaggggtagaagc | 50 |
| target-02-rs-R | tgtgtttggatttgcagtaggctgaagcgttatactatgactggagtcca | 51 |

TABLE 1-continued

Oligonucleotides as substrates

| name | Sequence (5'-3') | SEQ ID No.: |
|---|---|---|
| target-02-rs-12C-R | tgtgtttggatttgcagtaggctgaagcgttgtactatgactggagtcca | 52 |
| target-03-rs-R | aaaatagtgcttttttacttttatctgaatgattgaaatgtccttttccca | 53 |
| target-03-rs-12C-R | aaaatagtgcttttttacttttatctgaatgactgaaatgtccttttccca | 54 |
| DNMT1-3-C1A-R | gtcacgccacttgacaggcgagtaacagacatggaccatcagtgaacatt | 55 |
| DNMT1-3-C1T-R | gtcacgccacttgacaggcgagtaacagacatggaccatcagagaacatt | 56 |
| DNMT1-3-C2T-R | gtcacgccacttgacaggcgagtaacagacatggaccatcaaggaacatt | 57 |
| DNMT1-3-C2A-R | gtcacgccacttgacaggcgagtaacagacatggaccatcatggaacatt | 58 |
| DNMT1-3-T3G-R | gtcacgccacttgacaggcgagtaacagacatggaccatccgggaacatt | 59 |
| DNMT1-3-T3C-R | gtcacgccacttgacaggcgagtaacagacatggaccatcggggaacatt | 60 |
| DNMT1-3-G4T-R | gtcacgccacttgacaggcgagtaacagacatggaccataagggaacatt | 61 |
| DNMT1-3-G4A-R | gtcacgccacttgacaggcgagtaacagacatggaccattagggaacatt | 62 |
| DNMT1-3-A5G-R | gtcacgccacttgacaggcgagtaacagacatggaccaccagggaacatt | 63 |
| DNMT1-3-A5C-R | gtcacgccacttgacaggcgagtaacagacatggaccagcagggaacatt | 64 |
| DNMT1-3-T6G-R | gtcacgccacttgacaggcgagtaacagacatggaccctcagggaacatt | 65 |
| DNMT1-3-T6C-R | gtcacgccacttgacaggcgagtaacagacatggaccgtcagggaacatt | 66 |
| DNMT1-3-G7T-R | gtcacgccacttgacaggcgagtaacagacatggacaatcagggaacatt | 67 |
| DNMT1-3-G7A-R | gtcacgccacttgacaggcgagtaacagacatggactatcagggaacatt | 68 |
| DNMT1-3-G8T-R | gtcacgccacttgacaggcgagtaacagacatggaacatcagggaacatt | 69 |
| DNMT1-3-G8A-R | gtcacgccacttgacaggcgagtaacagacatggatcatcagggaacatt | 70 |
| DNMT1-3-T9G-R | gtcacgccacttgacaggcgagtaacagacatggcccatcagggaacatt | 71 |
| DNMT1-3-T9C-R | gtcacgccacttgacaggcgagtaacagacatgggccatcagggaacatt | 72 |
| DNMT1-3-C10T-R | gtcacgccacttgacaggcgagtaacagacatgaaccatcagggaacatt | 73 |
| DNMT1-3-C10A-R | gtcacgccacttgacaggcgagtaacagacatgtaccatcagggaacatt | 74 |
| DNMT1-3-C11T-R | gtcacgccacttgacaggcgagtaacagacatagaccatcagggaacatt | 75 |
| DNMT1-3-C11A-R | gtcacgccacttgacaggcgagtaacagacattgaccatcagggaacatt | 76 |
| DNMT1-3-A12G-R | gtcacgccacttgacaggcgagtaacagacacggaccatcagggaacatt | 77 |
| DNMT1-3-A12C-R | gtcacgccacttgacaggcgagtaacagacagggaccatcagggaacatt | 78 |
| DNMT1-3-T13G-R | gtcacgccacttgacaggcgagtaacagacctggaccatcagggaacatt | 79 |
| DNMT1-3-T13C-R | gtcacgccacttgacaggcgagtaacagacgtggaccatcagggaacatt | 80 |
| DNMT1-3-G14T-R | gtcacgccacttgacaggcgagtaacagaaatggaccatcagggaacatt | 81 |
| DNMT1-3-G14A-R | gtcacgccacttgacaggcgagtaacagatatggaccatcagggaacatt | 82 |
| DNMT1-3-T15G-R | gtcacgccacttgacaggcgagtaacagccatggaccatcagggaacatt | 83 |
| DNMT1-3-T15C-R | gtcacgccacttgacaggcgagtaacaggcatggaccatcagggaacatt | 84 |
| DNMT1-3-C16T-R | gtcacgccacttgacaggcgagtaacaaacatggaccatcagggaacatt | 85 |
| DNMT1-3-C16A-R | gtcacgccacttgacaggcgagtaacatacatggaccatcagggaacatt | 86 |
| target-01rs-C8G-R | agacttagatctgagccctccctcttcccagcacacgcaggggtagaagc | 87 |
| target-01rs-T9A-R | agacttagatctgagccctccctcttcccagcactggcaggggtagaagc | 88 |
| target-01rs-G10C-R | agacttagatctgagccctccctcttcccagcagaggcaggggtagaagc | 89 |

TABLE 1-continued

Oligonucleotides as substrates

| name | Sequence (5'-3') | SEQ ID No.: |
|---|---|---|
| target-01rs-T11A-R | agacttagatctgagccctccctcttcccagctcaggcaggggtagaagc | 90 |
| target-01rs-G12C-R | agacttagatctgagccctccctcttcccaggacaggcaggggtagaagc | 91 |
| target-01rs-C13G-R | agacttagatctgagccctccctcttcccaccacaggcaggggtagaagc | 92 |
| target-01rs-T14A-R | agacttagatctgagccctccctcttccctgcacaggcaggggtagaagc | 93 |
| target-01rs-G15C-R | agacttagatctgagccctccctcttccgagcacaggcaggggtagaagc | 94 |
| target-01rs-G16C-R | agacttagatctgagccctccctcttcgcagcacaggcaggggtagaagc | 95 |
| target-02rs-A8T-R | tgtgtttggatttgcagtaggctgaagcgttatacaatgactggagtcca | 96 |
| target-02rs-G9C-R | tgtgtttggatttgcagtaggctgaagcgttatagtatgactggagtcca | 97 |
| target-02rs-T10A-R | gtgtttggatttgcagtaggctgaagcgttattctatgactggagtcca | 98 |
| target-02rs-A11T-R | tgtgtttggatttgcagtaggctgaagcgttaaactatgactggagtcca | 99 |
| target-02rs-T12A-R | tgtgtttggatttgcagtaggctgaagcgttttactatgactggagtcca | 100 |
| target-02rs-A13T-R | tgtgtttggatttgcagtaggctgaagcgtaatactatgactggagtcca | 101 |
| target-02rs-A14T-R | tgtgtttggatttgcagtaggctgaagcgatatactatgactggagtcca | 102 |
| target-02rs-C15G-R | tgtgtttggatttgcagtaggctgaagccttatactatgactggagtcca | 103 |
| target-02rs-G16C-R | tgtgtttggatttgcagtaggctgaagggttatactatgactggagtcca | 104 |
| target-03rs-T8A-R | aaaatagtgcttttactttttatctgaatgattgatatgtccttttccca | 105 |
| target-03rs-T9A-R | aaaatagtgcttttactttttatctgaatgattgtaatgtccttttccca | 106 |
| target-03rs-C10G-R | aaaatagtgcttttactttttatctgaatgattcaaatgtccttttccca | 107 |
| target-03rs-A11T-R | aaaatagtgcttttactttttatctgaatgatagaaatgtccttttccca | 108 |
| target-03rs-A12T-R | aaaatagtgcttttactttttatctgaatgaatgaaatgtccttttccca | 109 |
| target-03rs-T13A-R | aaaatagtgcttttactttttatctgaatgtttgaaatgtccttttccca | 110 |
| target-03rs-C14G-R | aaaatagtgcttttactttttatctgaatcattgaaatgtccttttccca | 111 |
| target-03rs-A15T-R | aaaatagtgcttttactttttatctgaaagattgaaatgtccttttccca | 112 |
| target-03rs-T16A-R | aaaatagtgcttttactttttatctgattgattgaaatgtccttttccca | 113 |
| target-05rs-R | ggatctcctggcggaggtggtggtagaaggtccaggagcaggggtagccg | 114 |
| target-05rs-G11A-R | ggatctcctggcggaggtggtggtagaaggtctaggagcaggggtagccg | 115 |
| target-41rs-R | agcacatgtttgttgaatgagtcagtggatgacgtagatcagtatcttgt | 116 |
| target-41rs-G11A-R | agcacatgtttgttgaatgagtcagtggatgatgtagatcagtatcttgt | 117 |
| target-01rs-10SNP-F | gcttctttccctgcctgtgctgggaagagggagggctcagatctaagtct | 118 |
| target-01rs-10SNP-R | agacttagatctgagccctccctcttcccagcacaggcagggaaagaagc | 119 |
| target-01rs-10SNP-G10T-F | gcttctttccctgcctgttctgggaagagggagggctcagatctaagtct | 120 |
| target-01rs-10SNP-G10T-R | agacttagatctgagccctccctcttcccagaacaggcagggaaagaagc | 121 |
| target-01rs-12SNP-F | gcttttaccctgcctgtgctgggaagagggagggctcagatctaagtct | 122 |
| target-01rs-12SNP-R | agacttagatctgagccctccctcttcccagcacaggcaggggtaaagc | 123 |

TABLE 1-continued

Oligonucleotides as substrates

| name | Sequence (5'-3') | SEQ ID No.: |
|---|---|---|
| target-01rs-12SNP-G12T-F | gcttttaccccctgcctgttctgggaagagggagggctcagatctaagtct | 124 |
| target-01rs-12SNP-G12T-R | agacttagatctgagccctccctcttcccagaacaggcaggggtaaaagc | 125 |
| HEX-N12-BHQ1 | Hex-nnnnnnnnnnnn-Bhq1 | 126 |
| FAM-N12-Eclipse | Fam-nnnnnnnnnnnn-Eclipse | 126 |

TABLE 2

The template sequences used to transcribe sgRNA

| Oligo name | Sequence (5'-3') | SEQ ID No.: |
|---|---|---|
| T7-sgRNA-F | gaaattaatacgactcactataggg | 128 |
| T7-sgRNA-gyrB | tcgcgcttgtcgcgcagacgaatgatctacaacagtagaaattccctatagtgagtcgtattaatttc | 129 |
| ZLsgRNA-DNMT1-3-R | aacagacatggaccatcagggtg | 130 |
| ZLsgRNA-DNMT1-3-14 | catggaccatcagggtgccac | 131 |
| ZLsgRNA-DNMT1-3-15 | acatggaccatcagggtgccac | 132 |
| ZLsgRNA-DNMT1-3-16 | gacatggaccatcagggtgcc | 133 |
| ZLsgRNA-DNMT1-3-17 | agacatggaccatcagggtgc | 134 |
| ZLsgRNA-DNMT1-3-18 | cagacatggaccatcagggtg | 135 |
| ZLsgRNA-DNMT1-3-19 | acagacatggaccatcagggtg | 136 |
| ZL-01-rs-16-R | ccagcacaggcagggggtgccacttctcagatttgagaag | 137 |
| ZL-02-rs-16-R | cgttatactatgactggtgccacttctcagatttgagaag | 138 |
| ZL-03-rs-16-R | atgattgaaatgtcctgtgccacttctcagatttgagaag | 139 |
| ZL-01rs-16-G12T-R | ccagaacaggcagggggtgccacttctcagatttgagaag | 140 |
| ZL-02rs-16-T12C-R | cgttgtactatgactggtgccacttctcagatttgagaag | 141 |
| ZL-03rs-16-T12C-R | atgactgaaatgtcctgtgccacttctcagatttgagaag | 142 |
| ZL-sgRNA-05rs-16 | aggtccaggagcaggggtgccacttctcagatttgagaag | 143 |
| ZL-sgRNA-05rs--G11A-16 | aggtctaggagcaggggtgccacttctcagatttgagaag | 144 |
| ZL-sgRNA-41rs-16 | gatgacgtagatcagtgtgccacttctcagatttgagaag | 145 |
| ZL-sgRNA-41rs-G11A-16 | gatgatgtagatcagtgtgccacttctcagatttgagaag | 146 |
| ZL-gyrB-crRNA2-R | atatcttctacttctccactgtgccacttctcagatttgagaag | 147 |
| ZL-sry-crRNA3-R | tctagagaatcccagaatgcgtgccacttctcagatttgagaag | 148 |
| ZL-02rs-16-11SNP-R | gcgttatactatgactgtgccacttctcagatttgagaag | 149 |
| ZL-02rs-16-(T12C)11SNP-R | gcgttgtactatgactgtgccacttctcagatttgagaag | 150 |
| ZL-01rs-10SNP-18-R | cttcccagcacaggcagggtgccacttctcagatttgagaag | 151 |
| ZL-01rs-10SNPG10T-18-R | cttcccagaacaggcagggtgccacttctcagatttgagaag | 152 |
| ZL-01rs-12SNP-18-R | tcccagcacaggcaggggtgccacttctcagatttgagaag | 153 |
| ZL-01rs-12SNPG12T-18-R | tcccagaacaggcaggggtgccacttctcagatttgagaag | 154 |
| ZL-sgRNA-JEV-E453-R | tgtgatccaagacattccccgtgccacttctcagatttgagaag | 155 |

TABLE 2-continued

The template sequences used to transcribe sgRNA

| Oligo name | Sequence (5'-3') | SEQ ID No.: |
|---|---|---|
| ZL-sgRNA-JEV-NS170-R | ctcgtcagtgctctcctctcgtgccacttctcagatttgagaag | 156 |
| ZL-01rs-10SNP-19-R | tcttcccagcacaggcagggtgccacttctcagatttgagaag | 157 |
| ZL-01rs-10SNPG10T-19-R | tcttcccagaacaggcagggtgccacttctcagatttgagaag | 158 |
| ZL-01rs-12SNP-19-R | ttcccagcacaggcaggggtgccacttctcagatttgagaag | 159 |
| ZL-01rs-12SNPG12T-19-R | ttcccagaacaggcaggggtgccacttctcagatttgagaag | 160 |

TABLE 3

Oligonucleotides as primers for amplification

| Oligo name | Sequence (5'-3') | SEQ ID No.: |
|---|---|---|
| LAMP-DNM-F3 | gtgaacgttcccttagcact | 161 |
| LAMP-DNM-B3 | gggagggcagaactagtcc | 162 |
| LAMP-DNM-FIP | cgccacttgacaggcgagtaactgccacttattgggtcagc | 163 |
| LAMP-DNM-BIP | gcgtgttccccagagtgacttagcagettcctcctcctt | 164 |
| LAMP-DNM-LoopF | aggaaacattaacgtactgatg | 165 |
| LAMP-DNM-LoopB | ttccttttatttcccttcagc | 166 |
| LAMP-gyrB-F3 | cgacggcaaagaagacca | 167 |
| LAMP-gyrB-B3 | agcctgccaggtgagtac | 168 |
| LAMP-gyrB-FIP | cgggtggatcggcgttttgttcactatgaaggcggcatca | 169 |
| LAMP-gyrB-BIP | gtattggcgtcgaagtggcgttcgctgcggaatgttgttg | 170 |
| LAMP-gyrB-LoopF | ttgttcagatattcaacgaacg | 171 |
| LAMP-gyrB-LoopB | gtggaacgatggcttccagg | 172 |
| LAMP-sry-F3 | tctctgtgcatggcctgta | 173 |
| LAMP-sry-B3 | aacagtaaaggcaacgtcca | 174 |
| LAMP-sry-FIP | gcagctgggataccagtggaagtgcctcctggaagaatgg | 175 |
| LAMP-sry-BIP | tctctagagccatcttgcgcctgaagcgacccatgaacgc | 176 |
| LAMP-sry-LoopF | tgcttactgaagccgaaaaatg | 177 |
| LAMP-sry-LoopB | tgatcgcgagaccacacgatg | 178 |
| ASP-primer | ggtttcggatgttacagcgt | 179 |
| ASP-rs5082-F | caagcaccccaccgctcacccacctcctcctttg | 180 |
| ASP-rs5082-R | ggtttcggatgttacagcgtgtgctggaagacttagatctgag | 181 |
| LAMP-rs5082-F3 | gctggaaaggtcaagggac | 182 |
| LAMP-rs5082-B3 | ggggtttgttgcacagtcc | 183 |
| LAMP-rs5082-FIP | ggtagaagcaaaggcaggaggtttgcccaaggtcacacag | 184 |
| LAMP-rs5082-FIP-10PAM | gaaagaagcaaaggcaggaggtttgcccaaggtcacacag | 185 |
| LAMP-rs5082-BIP | ctgggaagagggagggctcagtgttgccacactttcactgg | 186 |
| LAMP-rs5082-LoopF | gtgagcgggtggggtgct | 187 |

TABLE 3-continued

Oligonucleotides as primers for amplification

| Oligo name | Sequence (5'-3') | SEQ ID No.: |
|---|---|---|
| LAMP-rs5082-LoopB | tctaagtcttccagcacgggatc | 188 |
| LAMP-E453-F3 | tgacacagcctgggactt | 189 |
| LAMP-E453-B3 | cacacctcctgtggctaag | 190 |
| LAMP-E453-FIP | gagtgttctgaaggcaccaccagctccattggagggtct | 191 |
| LAMP-E453-BIP | acacaagggctaatgggtgccgccaaagcaattgatcggtc | 192 |
| LAMP-E453-LoopF | ttggtgaacggcttttcctatg | 193 |
| LAMP-E453-LoopB | tgctctggatgggcgtcaacg | 194 |
| LAMP-NS170-F3 | gagacaaaggaatgccctga | 195 |
| LAMP-NS170-B3 | gccctctcaagtttccatgt | 196 |
| LAMP-NS170-FIP | cgggttgatgtgatgccaaagcgagcacagagcttggaaca | 197 |
| LAMP-NS170-BIP | ggagcgatcataggtacggctggcgactctcaatccagtacg | 198 |
| LAMP-NS170-LoopF | gaagtcttcgatttgcatg | 199 |
| LAMP-NS170-LoopB | acatgtggcagtccatagtgac | 200 |
| GAPDH-LAMP-target3-FIP | agggatctcgctcctggaagatcaccgtcaaggctgagaac | 201 |
| GAPDH-LAMP-target3-BIP | cgatgctggcgctgagtacgaatgagccccagccttct | 202 |
| GAPDH-LAMP-target3-F3 | tccacccatggcaaattcc | 203 |
| GAPDH-LAMP-target3-B3 | aggggcagagatgatgac | 204 |
| GAPDH-LAMP-target3-LoopF | tccattgatgacaagcttccc | 205 |
| GAPDH-LAMP-target3-LoopB | tcgtggagtccactggcgtc | 206 |
| CDR1as-LAMP-FIP | ccagatcttccaggaaaatccacatctgtatttgatggaagaccttt | 207 |
| CDR1as-LAMP-BIP | agaccagtaattgctggaagacttgtcttccaagaagctcc | 208 |
| CDR1as-LAMP-F3 | agattttctggaagacatgg | 209 |
| CDR1as-LAMP-B3 | atgtcttccggacaatcc | 210 |
| CDR1as-LAMP-LoopB | tgctggaagacttgatttactgg | 211 |
| COL1A2-F | ggaggcaccctagggccagggaaa | 212 |
| COL1A2-R | gttactgcaagcagcaacaaagtcc | 213 |
| COL1A2(BSP)-F | ggaggtattttagggttagggaaa | 214 |
| COL1A2(BSP)-R | attactacaaacaacaacaaaatcc | 215 |

TABLE 3-continued

Oligonucleotides as primers for amplification

| Oligo name | Sequence (5'-3') | SEQ ID No.: |
|---|---|---|
| sgRNA-GAPDH-target3-7 | ggcgtcttcaccaccatggagtgccacttctcagatttgagaag | 216 |
| sgRNA-CDR1as-target1-3 | ctccaagtcttccagtaaatgtgccacttctcagatttgagaag | 217 |
| sgRNA-COL1A2m3-C12-17 | ctaccgtaatactaaaagtgccacttctcagatttgagaag | 127 |

All publications mentioned herein are incorporated by reference as if each individual document was cited as a reference in the present application. It should be understood that, after reading the above teachings of the present invention, those skilled in the art can make various modifications and changes. These equivalent forms are also within the scope defined by the claims appended hereto.

The invention claimed is:

1. A method for detecting whether target nucleic acid molecules are present in a sample, which comprises the steps of:
  (i) providing a detection system, comprising:
    (a) a Cas protein, wherein the Cas protein is Cas12b;
    (b) a guiding RNA, wherein the guiding RNA directs the Cas protein to specifically bind to the target nucleic acid molecules;
    (c) a nucleic acid probe, which is a single-stranded DNA;
    wherein, the target nucleic acid molecule is a target DNA;
    (d) buffer;
    (e1) a polymerase, which is used for amplifying target DNA;
    (e2) an optional reverse transcriptase, which is used for reverse transcription;
    (e3) dNTP, which is used for amplification reaction and/or reverse transcription reaction; and
    (f) a sample to be tested;
  (ii) performing a reverse transcription and/or amplification reaction in the detection system, thereby obtaining a detection system reverse transcripted and/or amplified; and
  (iii) detecting whether the nucleic acid probe in the detection system obtained in the previous step is cleaved by the Cas protein, wherein the cleavage is a trans-cleavage of a bypass single-stranded DNA;
  wherein, if the nucleic acid probe is cleaved by the Cas protein, it indicates that the target nucleic acid molecule is present in the sample; and if the nucleic acid probe is not cleaved by the Cas protein, it indicates that the target nucleic acid molecule is not present in the sample;
  wherein in the detection, a nucleic acid amplification reaction and a collateral cleavage reaction are included, and the nucleic acid amplification reaction and the collateral cleavage reaction are performed simultaneously, and the detection system is a one-step reaction system and the temperature of the detection system is maintained at 50-70° C.

2. The method of claim 1, wherein the detection is quantitative detection.

3. The method of claim 1, wherein the nucleic acid amplification is selected from the group consisting of: Loop-mediated isothermal amplification(LAMP), Recombinase Polymerase Amplification(RPA), branched DNA amplification(bDNA), Nuclear acid sequence-based amplification(NASBA), Strand Displacement Amplification (SDA), transcription-mediated amplification(TMA), rolling circle amplification(RCA), helicase-dependent amplification(HDA), Single primer isothermal amplification(SPIA), Nicking enzyme amplification reaction(NEAR), Transcription Mediated Amplification(TMA) and Smart amplification process version 2(SmartAmp2).

4. The method of claim 1, wherein the target nucleic acid molecule is a methylated nucleic acid sequence, or the methylated nucleic acid sequence is a nucleic acid sequence obtained after an conversion of unmethylated C to uracil.

5. The method of claim 2, wherein the quantitative detection is an absolute quantitative detection.

6. The method of claim 1, wherein the detection is quantitative detection and the quantitative detection is a quantitative detection measured in a digital PCR instrument.

7. The method of claim 1, wherein when the target nucleic acid molecule is ssDNA, a detection site of the target nucleic acid molecule is located at position 9 or positions 10-16 downstream of the PAM sequence of the guiding RNA.

8. The method of claim 7, wherein when the detection site is located at position 9 downstream of the PAM sequence of the guiding RNA, the detection site is G.

9. The method of claim 7, wherein a detection site of the target nucleic acid molecule is located at positions 10-14 downstream of the PAM sequence of the guiding RNA.

10. The method of claim 9, wherein a detection site of the target nucleic acid molecule is located at positions 10-12 downstream of the PAM sequence of the guiding RNA.

* * * * *